United States Patent
Jung et al.

(10) Patent No.: US 11,370,782 B2
(45) Date of Patent: Jun. 28, 2022

(54) COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Dong Hoon Lee, Daejeon (KR); Boon Jae Jang, Daejeon (KR); Jungha Lee, Daejeon (KR); Su Jin Han, Daejeon (KR); Seulchan Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 374 days.

(21) Appl. No.: 16/645,770

(22) PCT Filed: Mar. 6, 2019

(86) PCT No.: PCT/KR2019/002608
§ 371 (c)(1),
(2) Date: Mar. 9, 2020

(87) PCT Pub. No.: WO2019/172652
PCT Pub. Date: Sep. 12, 2019

(65) Prior Publication Data
US 2020/0317650 A1    Oct. 8, 2020

(30) Foreign Application Priority Data
Mar. 6, 2018    (KR) .................. 10-2018-0026388

(51) Int. Cl.
| | | |
|---|---|---|
| *C07D 405/14* | (2006.01) | |
| *C07D 405/04* | (2006.01) | |
| *C07D 409/04* | (2006.01) | |
| *C07D 409/14* | (2006.01) | |
| *H01L 51/00* | (2006.01) | |

(52) U.S. Cl.
CPC ......... *C07D 405/14* (2013.01); *C07D 405/04* (2013.01); *C07D 409/04* (2013.01); *C07D 409/14* (2013.01); *H01L 51/0067* (2013.01); *H01L 51/0072* (2013.01); *H01L 51/0073* (2013.01); *H01L 51/0074* (2013.01)

(58) Field of Classification Search
CPC .. C07D 405/14; C07D 405/04; C07D 409/04; C07D 409/14; H01L 51/0067; H01L 51/0072; H01L 51/0073; H01L 51/0074
See application file for complete search history.

(56) References Cited

U.S. PATENT DOCUMENTS

| | | |
|---|---|---|
| 2004/0251816 A1 | 12/2004 | Leo et al. |
| 2016/0028021 A1 | 1/2016 | Zeng et al. |
| 2016/0093808 A1 | 3/2016 | Adamovich et al. |
| 2016/0197285 A1 | 7/2016 | Zeng et al. |
| 2017/0054087 A1 | 2/2017 | Zeng et al. |
| 2017/0186965 A1 | 6/2017 | Parham et al. |
| 2017/0213983 A1 | 7/2017 | Hayama et al. |
| 2018/0337348 A1 | 11/2018 | Jung et al. |

FOREIGN PATENT DOCUMENTS

| | | |
|---|---|---|
| KR | 10-20000051826 | 8/2000 |
| KR | 10-20160006633 | 1/2016 |
| KR | 10-20160028524 | 3/2016 |
| KR | 10-20170086211 | 7/2017 |
| KR | 10-20170089599 | 8/2017 |
| KR | 10-20180010130 | 1/2018 |
| WO | 2003012890 | 2/2003 |
| WO | 2016084962 | 6/2016 |

*Primary Examiner* — Rebecca L Anderson
(74) *Attorney, Agent, or Firm* — Dentons US LLP

(57) ABSTRACT

Provided is a compound of Chemical Formula 1:

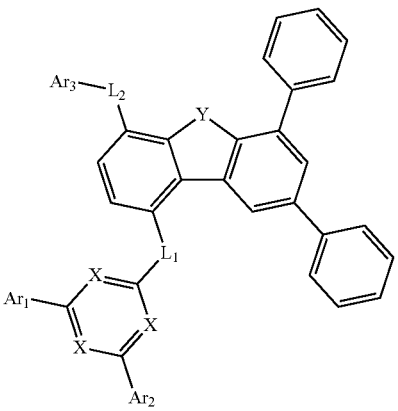

[Chemical Formula 1]

wherein:
each X is independently N or CH, with the proviso that at least one X is N;
Y is O or S;
$L_1$ and $L_2$ are each independently a single bond, a substituted or unsubstituted $C_{6-60}$ arylene, or a substituted or unsubstituted $C_{2-60}$ heteroarylene containing at least one heteroatom selected from the group consisting of N, O, and S;
$Ar_1$ and $Ar_2$ are each independently a substituted or unsubstituted $C_{6-60}$ aryl, or a substituted or unsubstituted $C_{2-60}$ heteroaryl containing at least one heteroatom selected from the group consisting of N, O, and S; and
$Ar_3$ is a substituted or unsubstituted $C_{6-60}$ aryl, or a substituted or unsubstituted $C_{2-60}$ heteroaryl containing at least one heteroatom selected from the group consisting of N, O, and S;
and to an organic light emitting device including the same.

9 Claims, 1 Drawing Sheet

[FIG. 1]
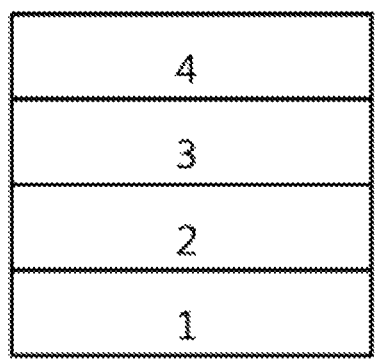
[FIG. 2]
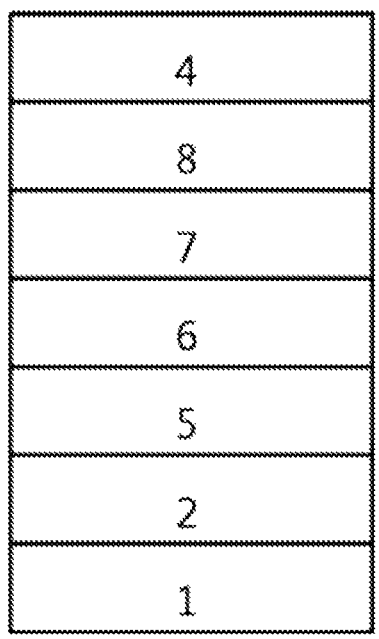

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/002608 filed on Mar. 6, 2019, which claims the benefit of the filing date of Korean Patent Application No. 10-2018-0026388 filed with Korean Intellectual Property Office on Mar. 6, 2018, the entire content of which is incorporated herein by reference.

TECHNICAL FIELD

The present disclosure relates to a novel compound and to an organic light emitting device including the same.

BACKGROUND

In general, an organic light emitting phenomenon is a phenomenon where electrical energy is converted into light energy by using an organic material. The organic light emitting device using the organic light emitting phenomenon has characteristics such as a wide viewing angle, excellent contrast, a fast response time, an excellent luminance, driving voltage, and response speed, and thus many studies have proceeded thereon.

The organic light emitting device generally has a structure that includes an anode, a cathode, and an organic material layer interposed between the anode and the cathode. The organic material layer frequently has a multilayered structure that includes different materials in order to enhance efficiency and stability of the organic light emitting device, and for example, the organic material layer can be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

PRIOR ART LITERATURE

Patent Literature

Korean Patent Laid-open Publication No. 10-2000-0051826

BRIEF DESCRIPTION

Technical Problem

It is an object of the present disclosure to provide a novel compound and an organic light emitting device including the same.

Technical Solution

The present disclosure provides a compound of Chemical Formula 1:

[Chemical Formula 1]

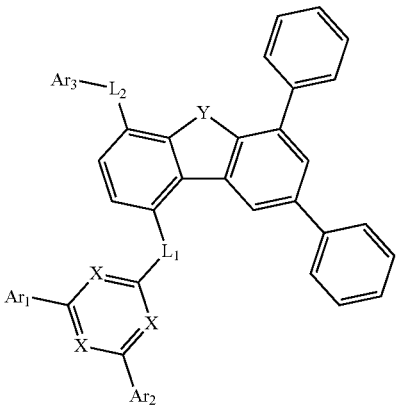

wherein, in Chemical Formula 1:
each X is independently N or CH, with the proviso that at least one X is N;
Y is O or S;
$L_1$ and $L_2$ are each independently a single bond, a substituted or unsubstituted $C_{6-60}$ arylene, or a substituted or unsubstituted $C_{2-60}$ heteroarylene containing at least one heteroatom selected from the group consisting of N, O, and S;
$Ar_1$ and $Ar_2$ are each independently a substituted or unsubstituted $C_{6-60}$ aryl, or a substituted or unsubstituted $C_{2-60}$ heteroaryl containing at least one heteroatom selected from the group consisting of N, O, and S; and
$Ar_3$ is a substituted or unsubstituted $C_{6-60}$ aryl, or a substituted or unsubstituted $C_{2-60}$ heteroaryl containing at least one heteroatom selected from the group consisting of N, O, and S.

Further, the present disclosure provides an organic light emitting device including a first electrode; a second electrode provided opposite to the first electrode; and one or more organic material layers provided between the first electrode and the second electrode, wherein one or more layers of the organic material layers includes the compound of Chemical Formula 1.

Advantageous Effects

The compound of Chemical Formula 1 can be used as a material of the organic material layer of the organic light emitting device, and can improve efficiency, low driving voltage, and/or lifetime characteristics in the organic light emitting device. In particular, the compound of Chemical Formula 1 can be used as a hole injection, hole transport, hole injection and transport, light emission, electron transport, or electron injection material.

BRIEF DESCRIPTION OF DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, a light emitting layer 7, an electron transport layer 8, and a cathode 4.

DETAILED DESCRIPTION

Hereinafter, the present disclosure will be described in more detail to help understanding of the present disclosure.

The present disclosure provides a compound of Chemical Formula 1.

As used herein, the notation

means a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group containing at least one of N, O, and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group, and can be interpreted as a substituent to which two phenyl groups are linked.

In the present disclosure, the number of carbon atoms of a carbonyl group is not particularly limited, but is preferably 1 to 40. Specifically, the carbonyl group can be a compound having the following structural formulae, but is not limited thereto:

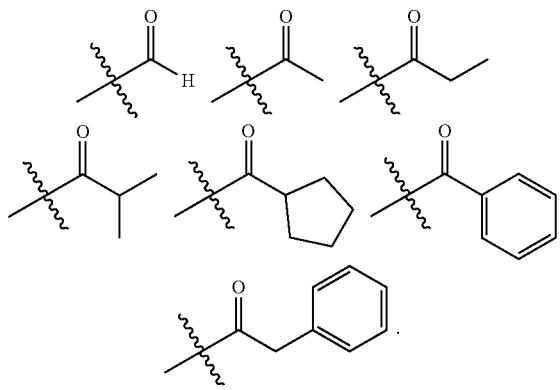

In the present disclosure, for an ester group, the oxygen of the ester group can be substituted with a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto:

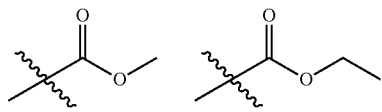

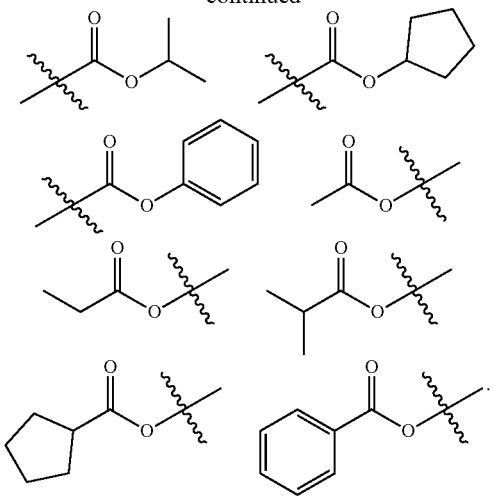

In the present disclosure, the number of carbon atoms of an imide group is not particularly limited, but is preferably 1 to 25. Specifically, the imide group can be a compound having the following structural formulae, but is not limited thereto:

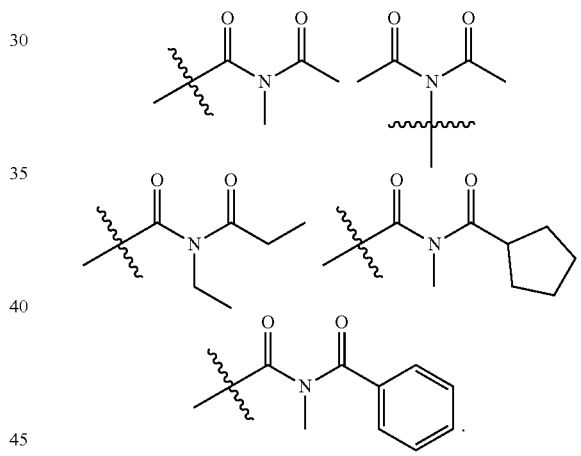

In the present disclosure, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present disclosure, the boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group can be a straight chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 2-methylpentyl, 4-methylhexyl, 5-methylhexyl, and the like, but are not limited thereto.

In the present disclosure, the alkenyl group can be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, the aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, and a fluorenyl group, or the like, but are not limited thereto.

In the present disclosure, a fluorenyl group can be substituted, and two substituent groups can be bonded to each other to form a spiro structure. In the case where the fluorenyl group is substituted,

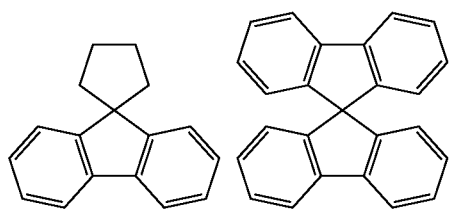

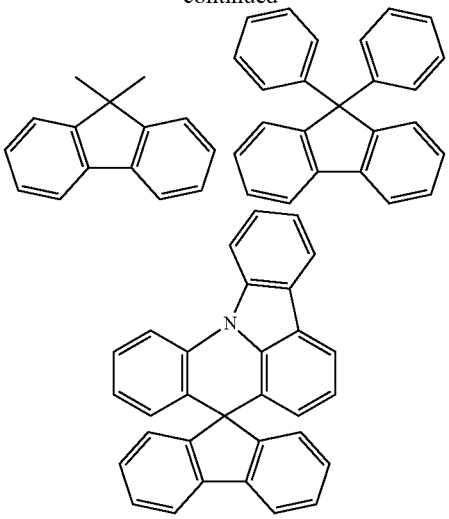

can be formed. However, the structure is not limited thereto.

In the present disclosure, the heterocyclic group is a heterocyclic group including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group, and the arylamine group is the same as the aforementioned examples of the aryl group. In the present disclosure, the alkyl group in the aralkyl group, the alkylaryl group, and the alkylamine group is the same as the aforementioned examples of the alkyl group. In the present disclosure, the heteroaryl in the heteroarylamine can be applied to the aforementioned description of the heterocyclic group. In the present disclosure, the alkenyl group in the aralkenyl group is the same as the aforementioned examples of the alkenyl group. In the present disclosure, the aforementioned description of the aryl group can be applied except that the arylene is a divalent group. In the present disclosure, the aforementioned description of the heterocyclic group can be applied except that the heteroarylene is a divalent group. In the present disclosure, the aforementioned description of the aryl group or cycloalkyl group can be applied except that the hydrocarbon ring is not a monovalent group but is formed by combining two substituent groups. In the present disclosure, the aforementioned description of the heterocyclic group can be applied, except that the heterocycle is not a monovalent group but is formed by combining two substituent groups.

Preferably, each X is N.

Preferably, $L_1$ is a single bond, phenylene, biphenyldiyl, naphthalenediyl, or pyridinediyl.

Preferably, $L_2$ is a single bond, or phenylene.

Preferably, $Ar_1$ and $Ar_2$ are each independently phenyl, biphenylyl, terphenylyl, naphthyl, phenanthrenyl, dibenzofuranyl, dibenzothiophenyl, carbazolyl, or 9-phenyl-9H-carbazolyl. More preferably, $Ar_1$ is phenyl, and $Ar_2$ is phenyl, biphenylyl, terphenylyl, naphthyl, phenanthrenyl, dibenzofuranyl, dibenzothiophenyl, carbazolyl, or 9-phenyl-9H-carbazolyl.

Preferably, $Ar_3$ is unsubstituted, or is substituted with a $C_{1-60}$ alkyl, a halogen, cyano, or tri($C_{1-60}$ alkyl)silyl. More preferably, $Ar_3$ is unsubstituted, or is substituted with tert-butyl, fluoro, cyano, or trimethylsilyl.

Preferably, $Ar_3$ is phenyl, biphenylyl, terphenylyl, naphthyl, phenanthrenyl, triphenylenyl, pyridinyl, quinolinyl, dibenzofuranyl, or dibenzothiophenyl. Here, $Ar_3$ can be unsubstituted, or is substituted with a substituent as described above.

Representative examples of the compound of Chemical Formula 1 are as follows:

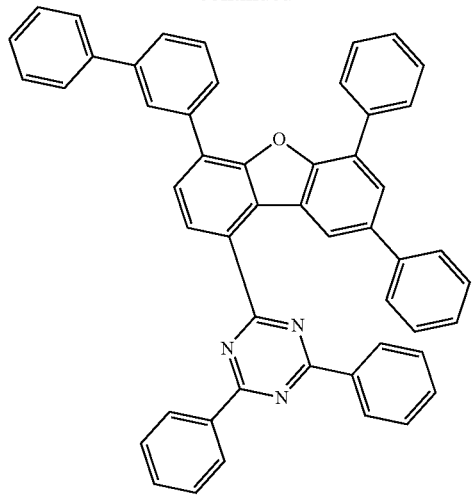

-continued

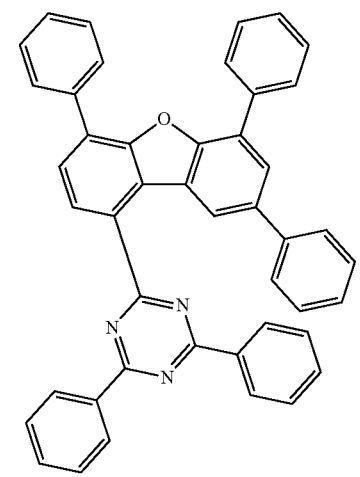

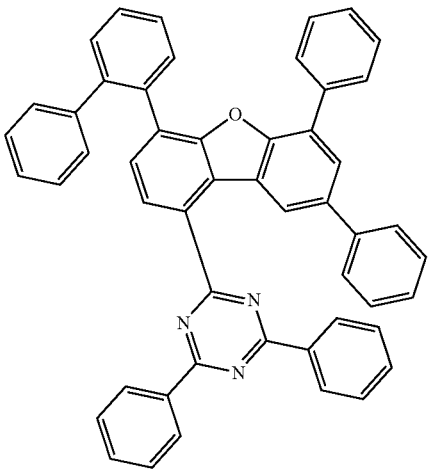

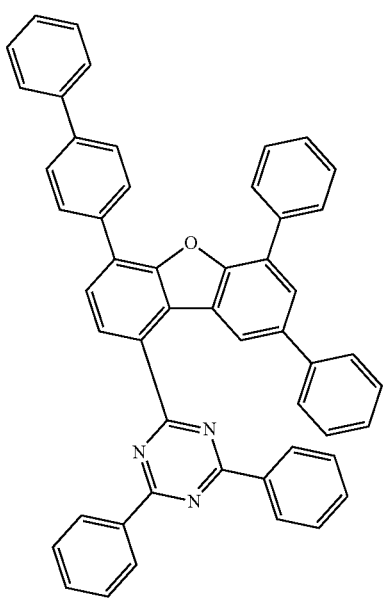

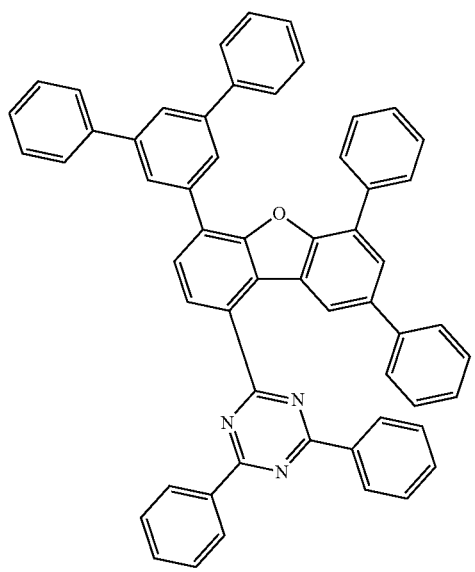

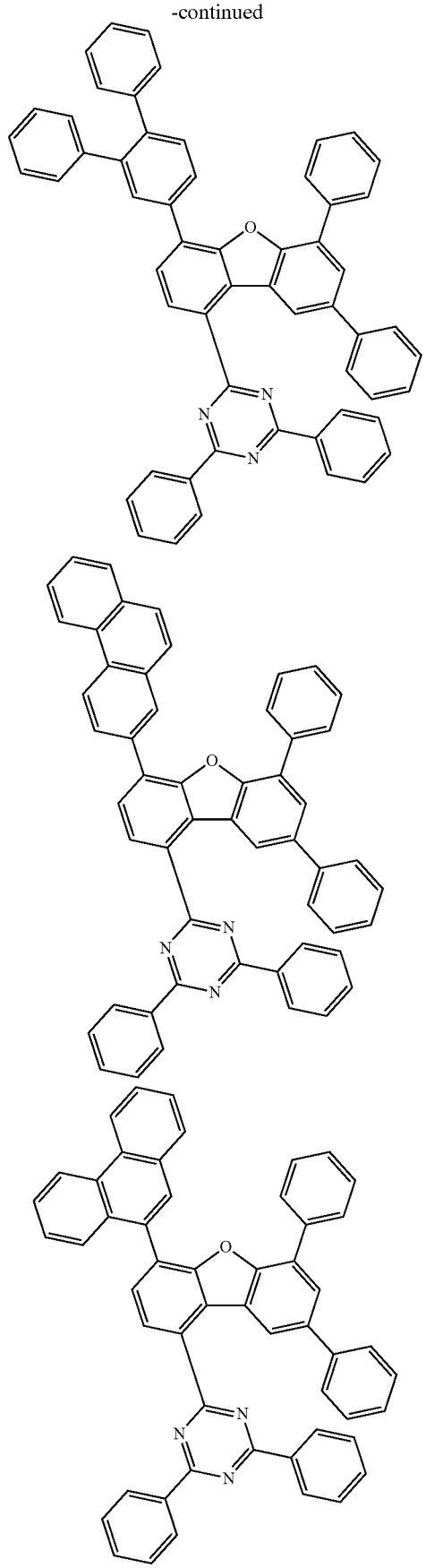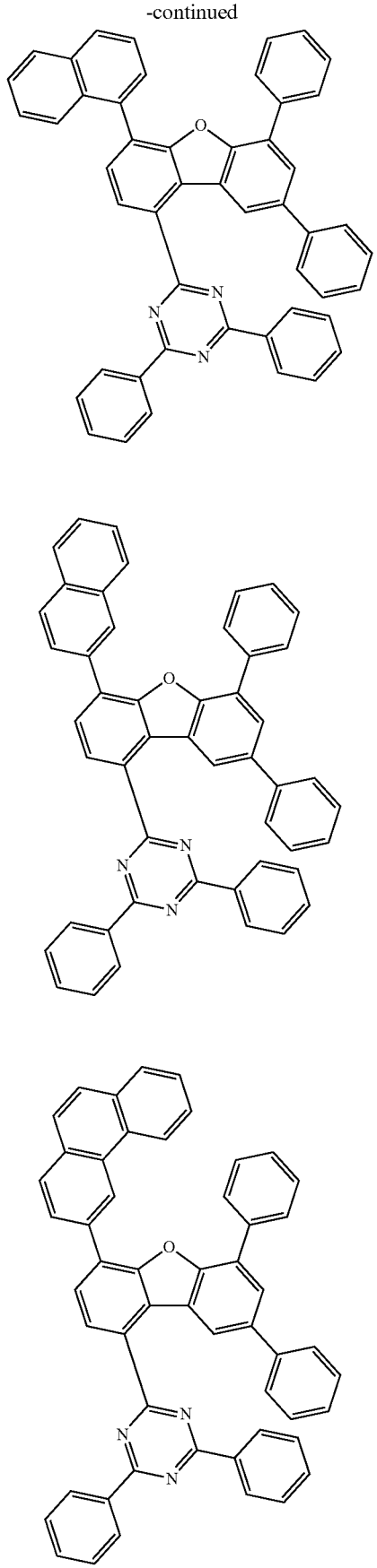

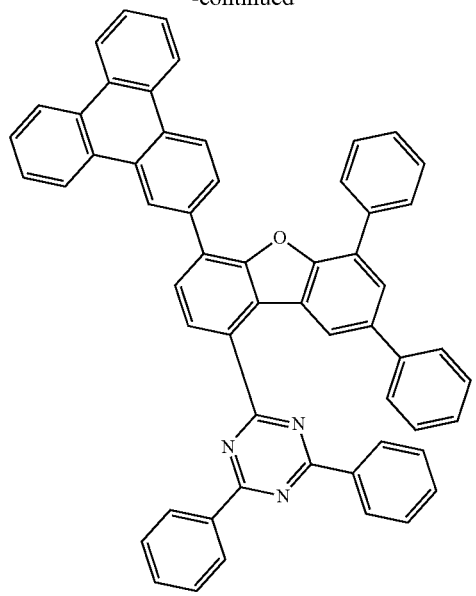
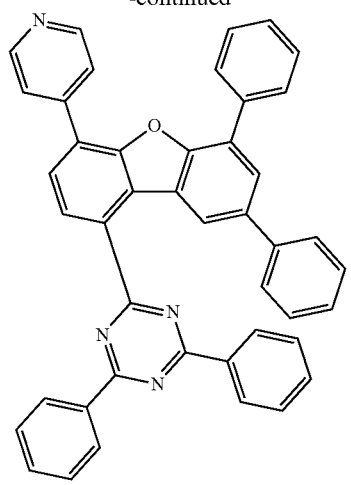
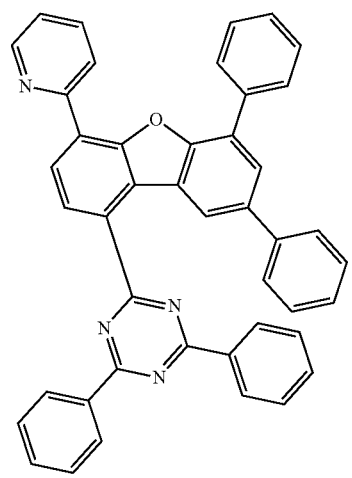
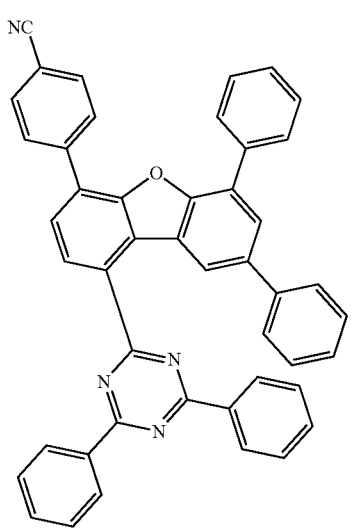
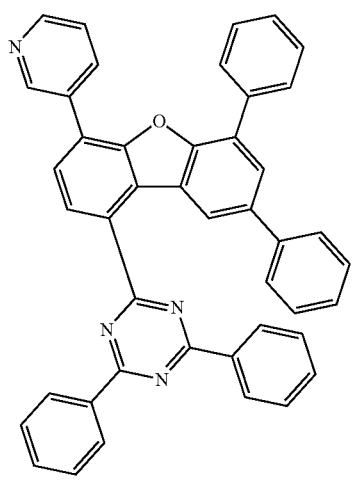
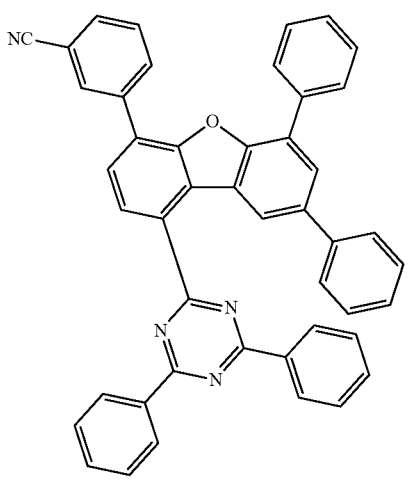

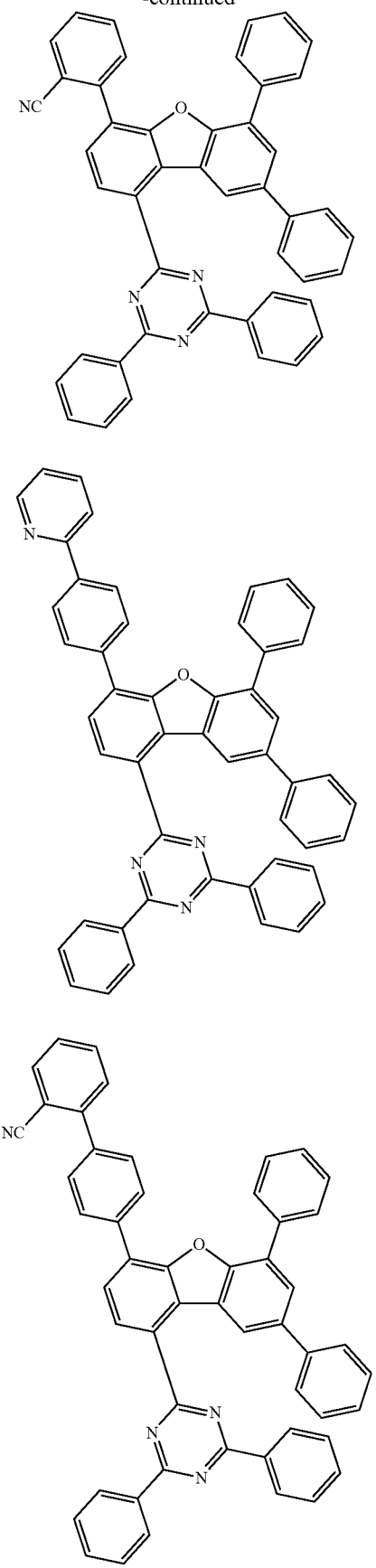
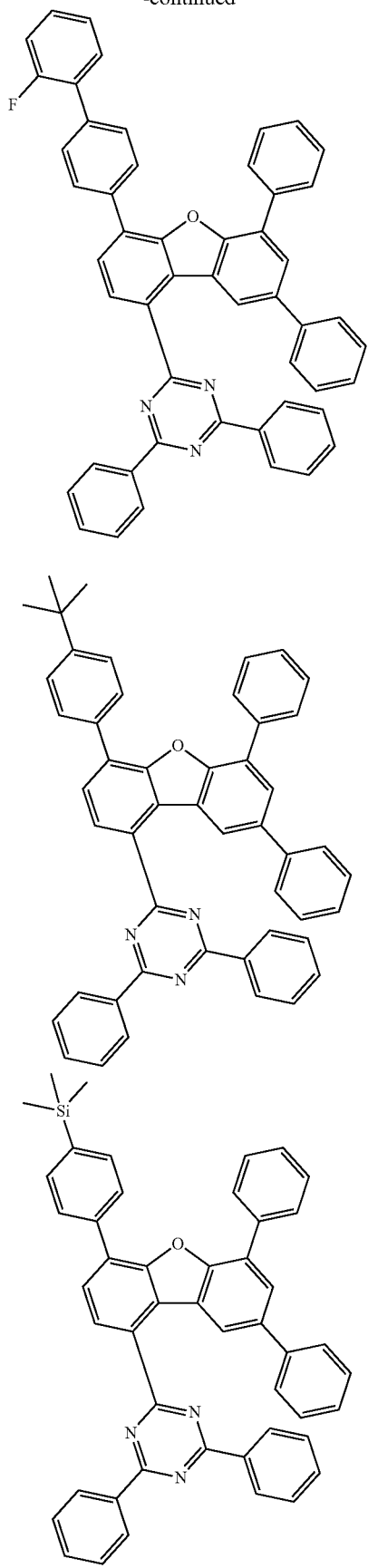

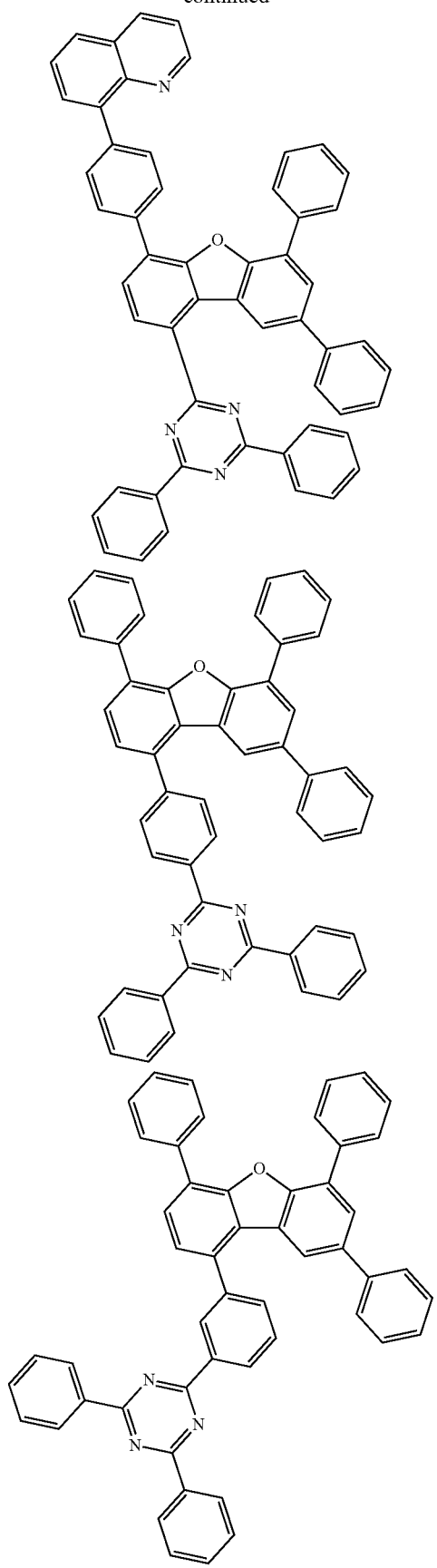
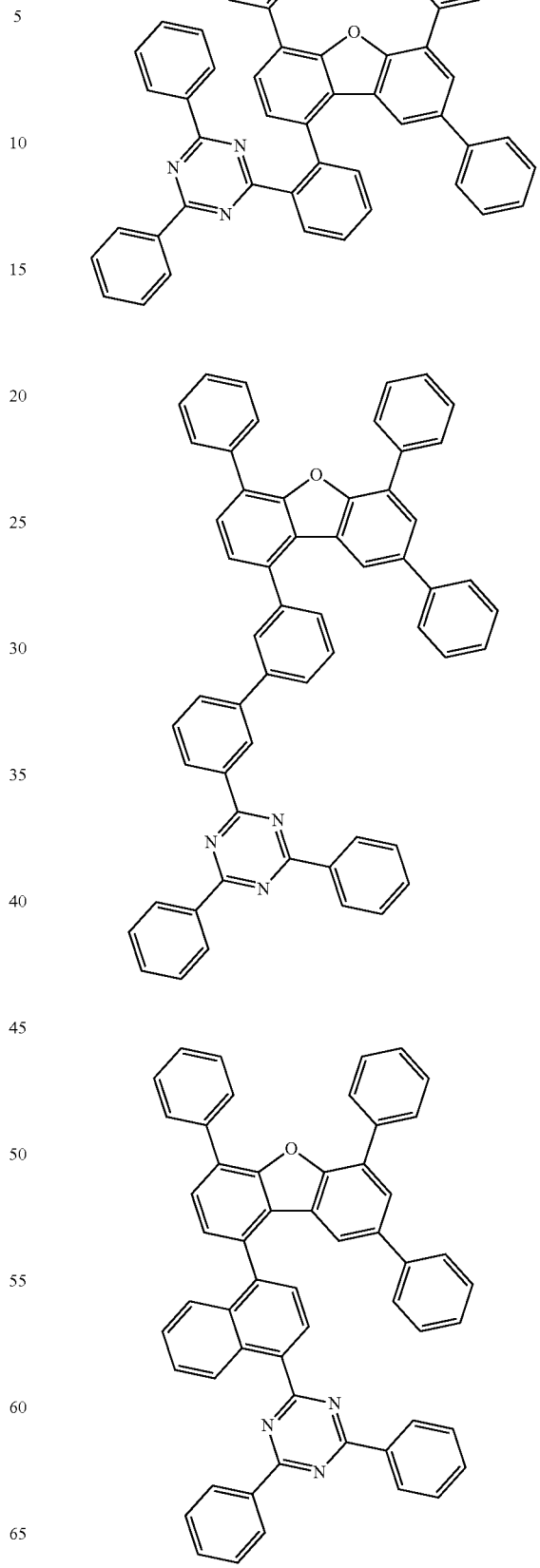

-continued
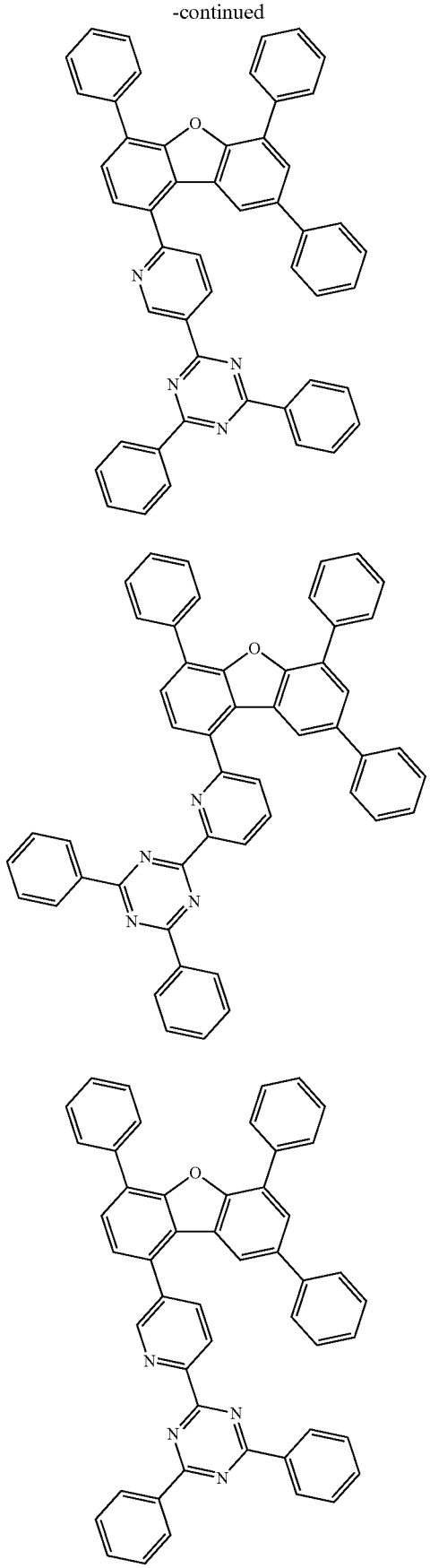
-continued
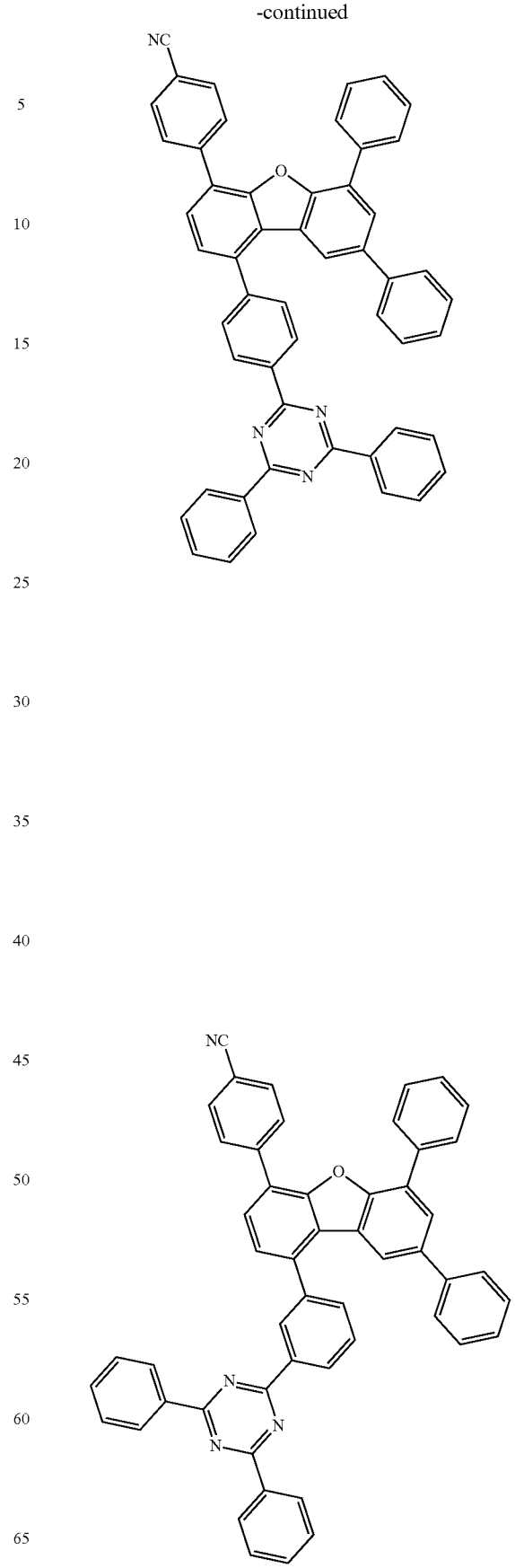

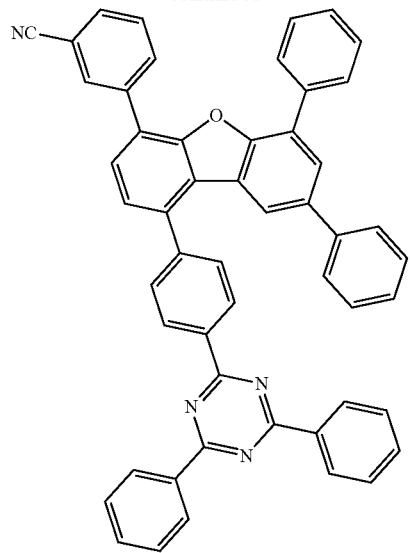
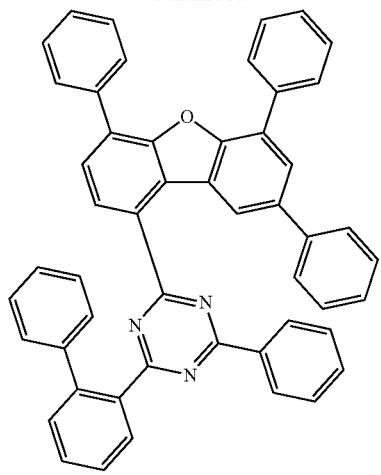
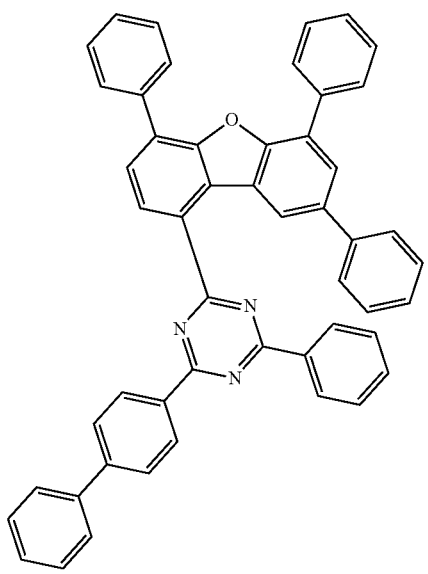
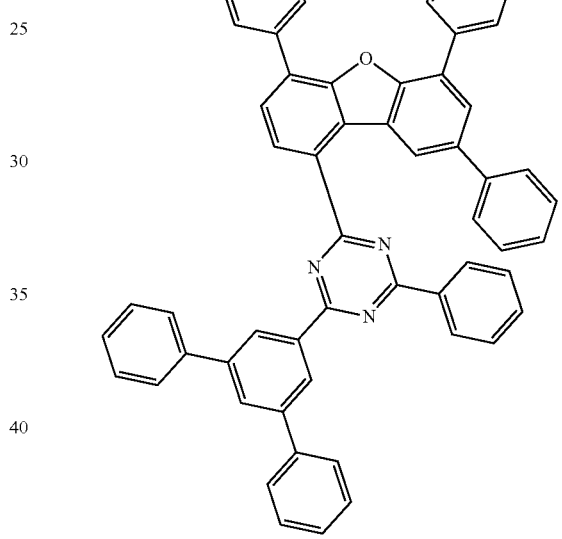
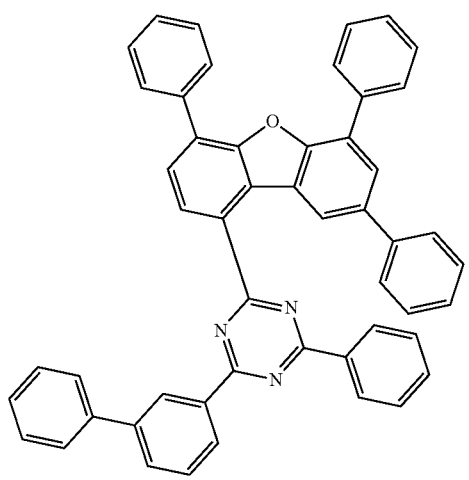
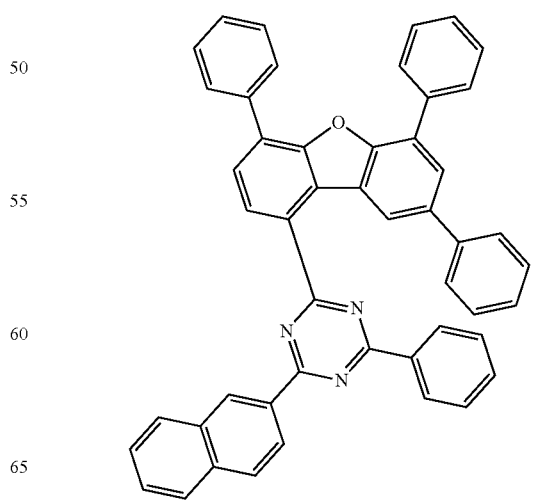

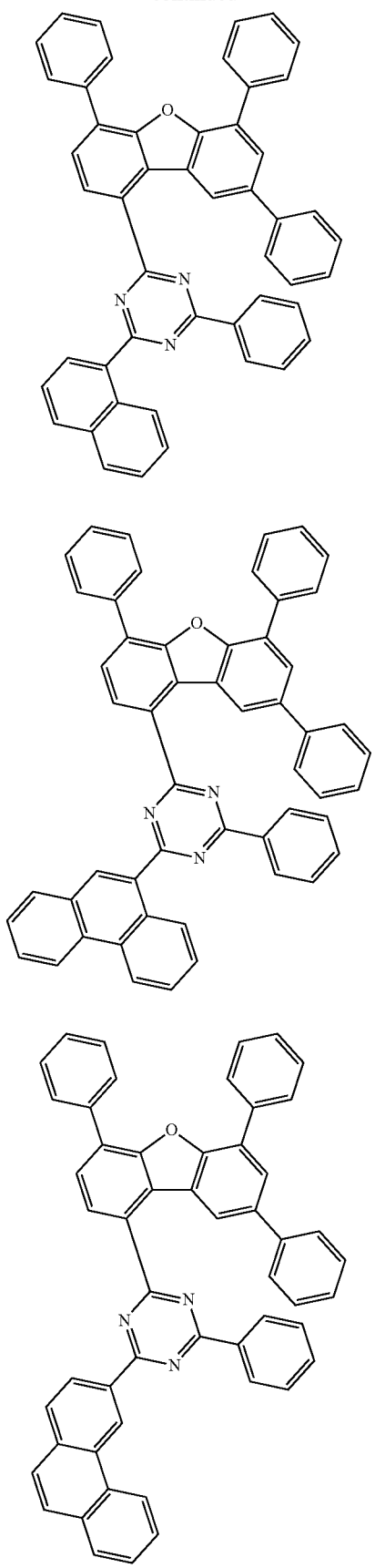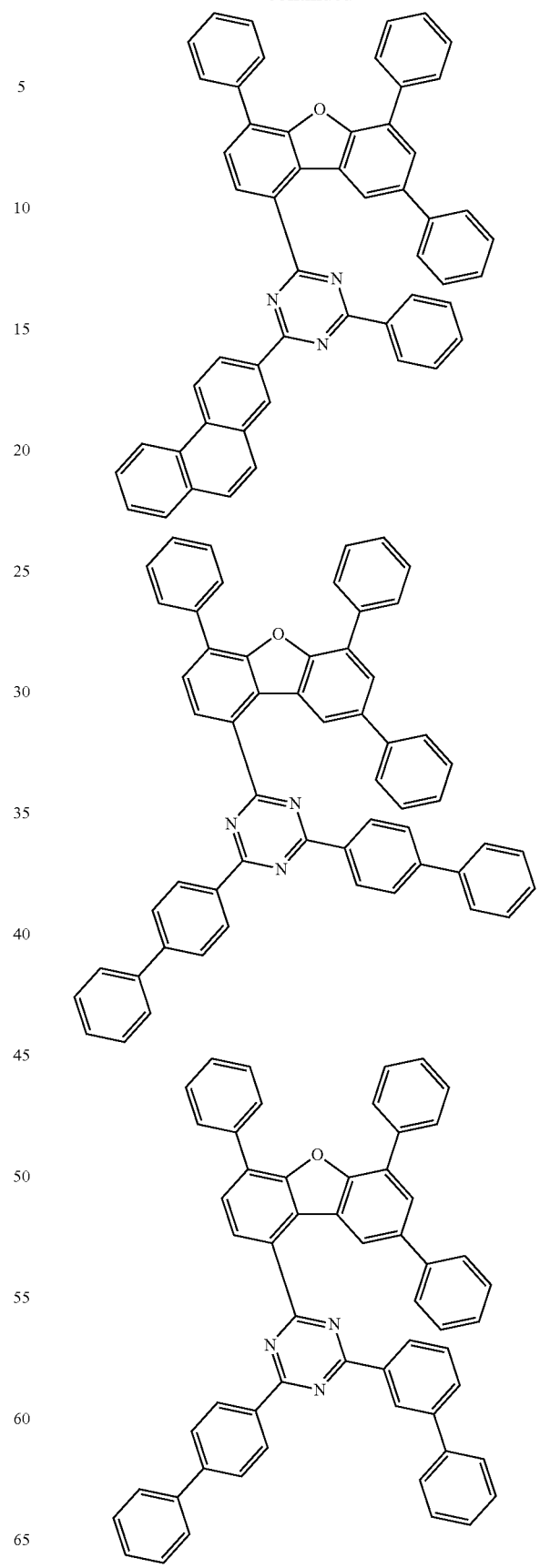

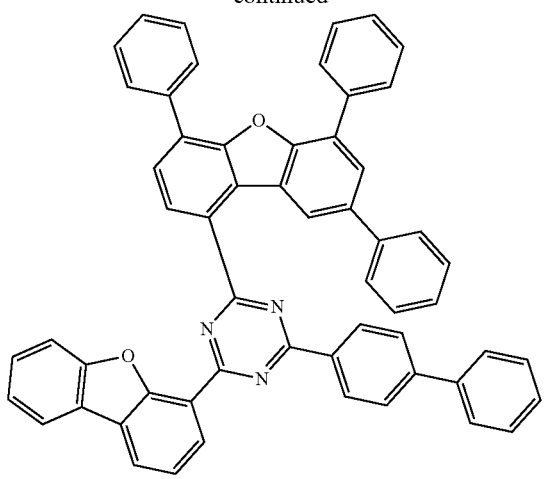
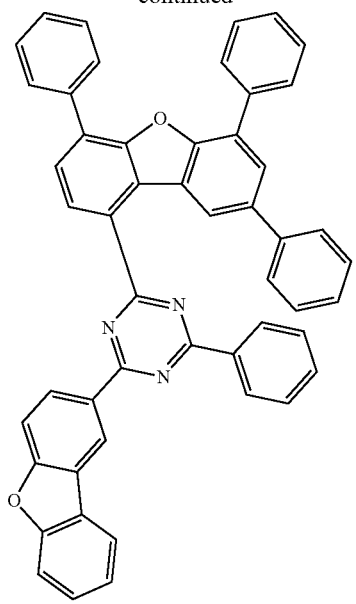
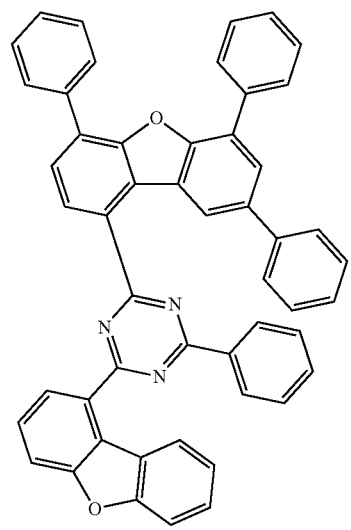
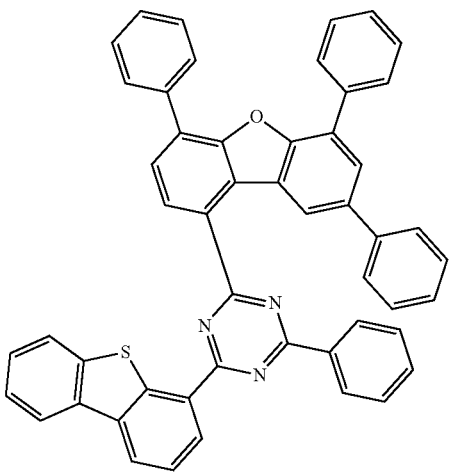

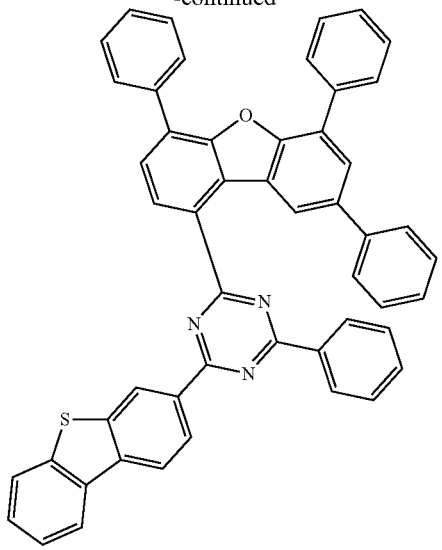
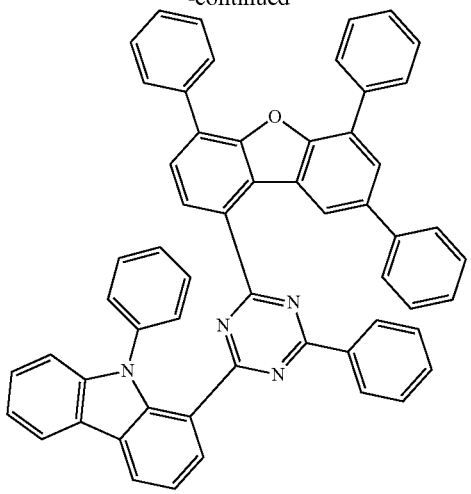

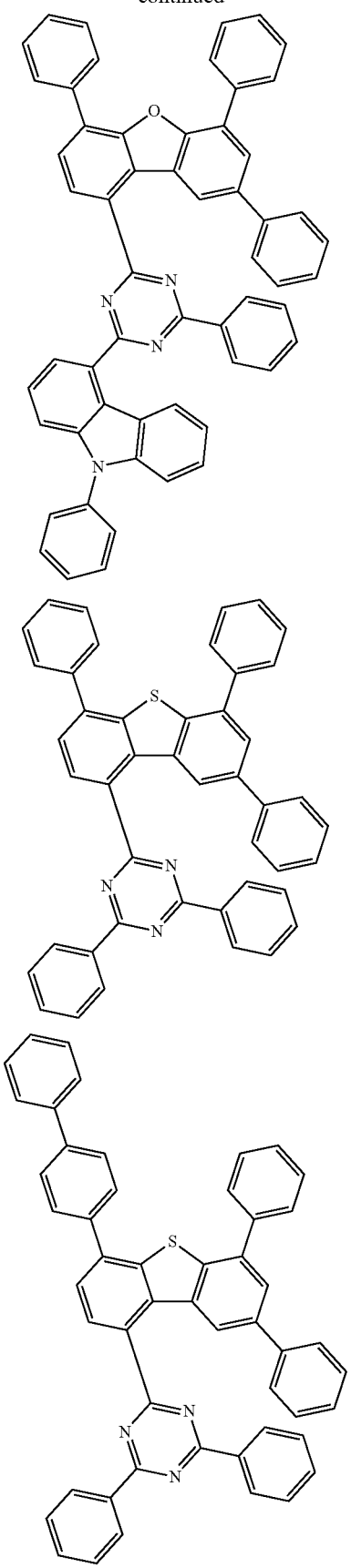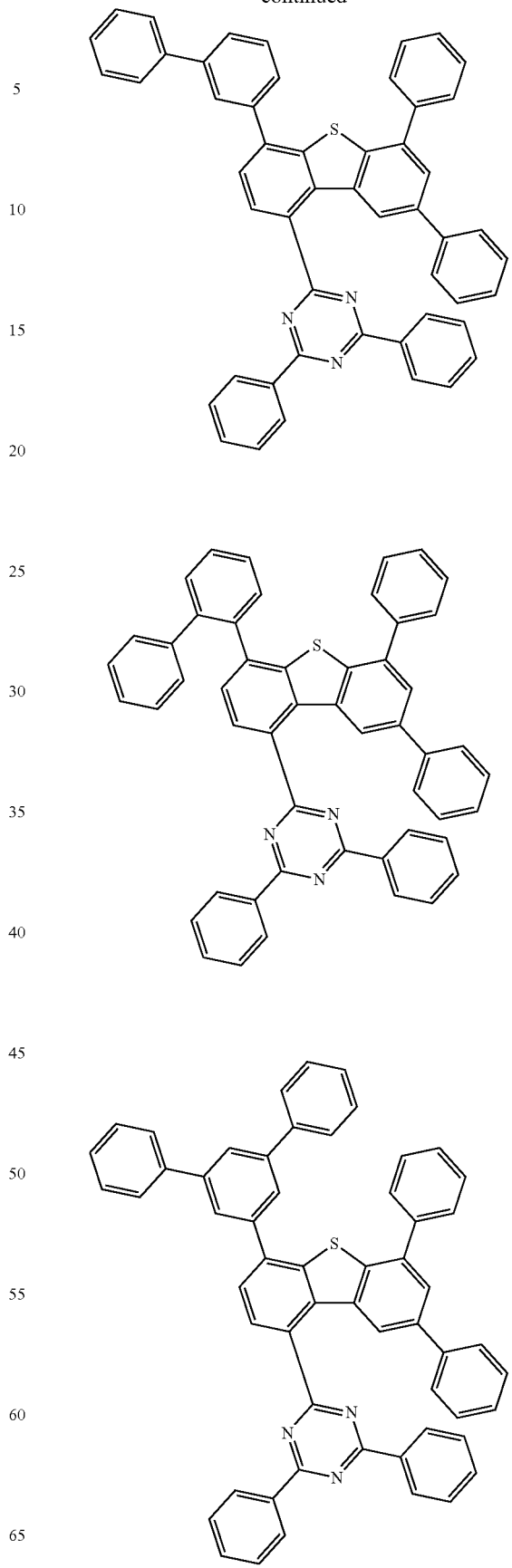

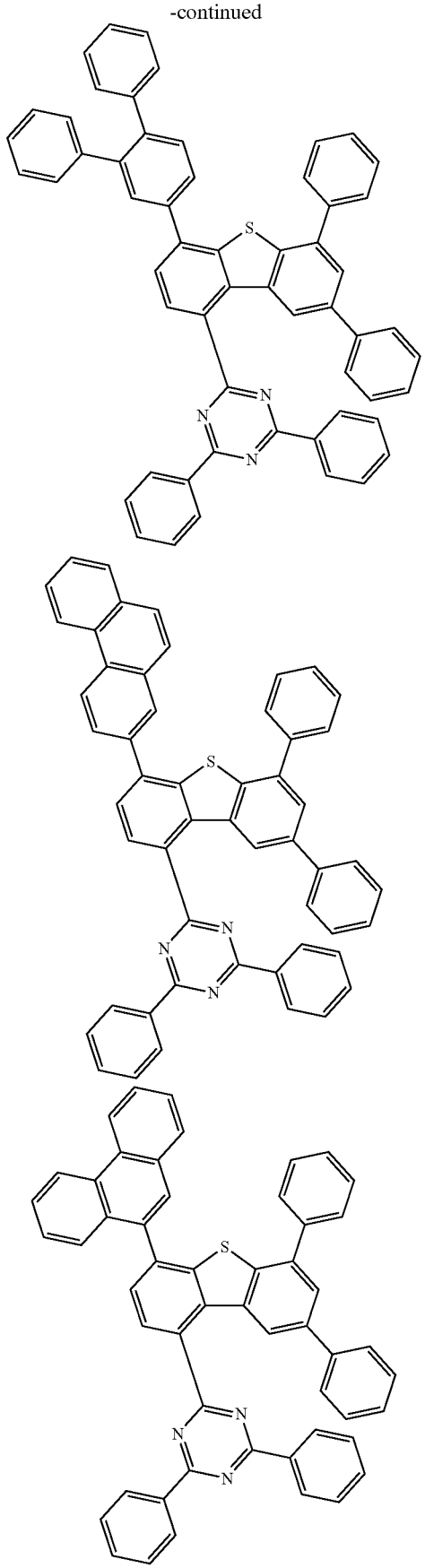
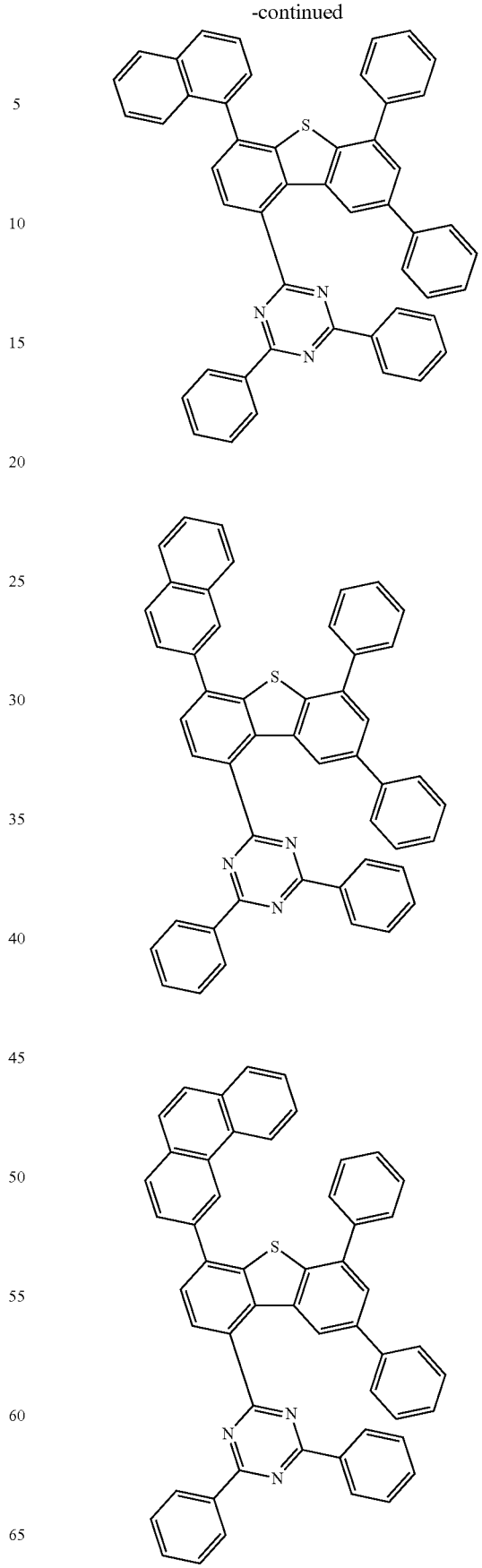

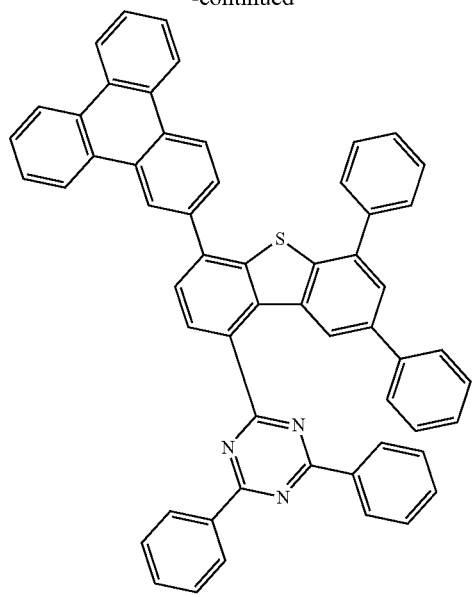
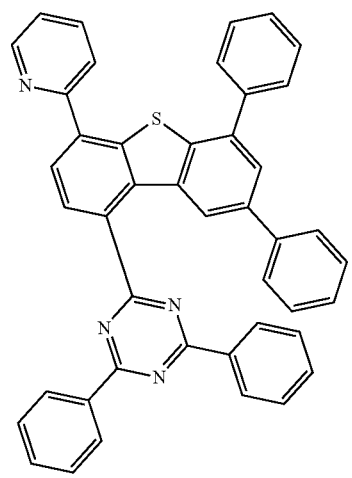
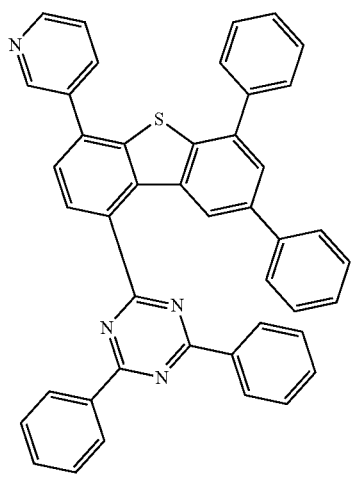
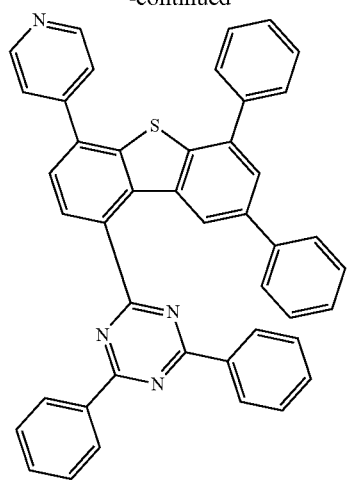
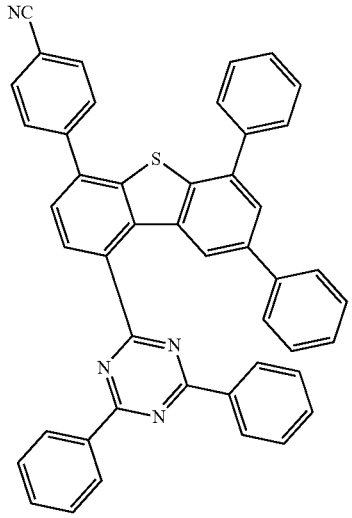
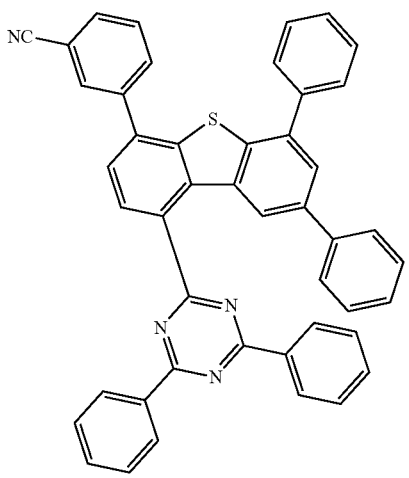

-continued
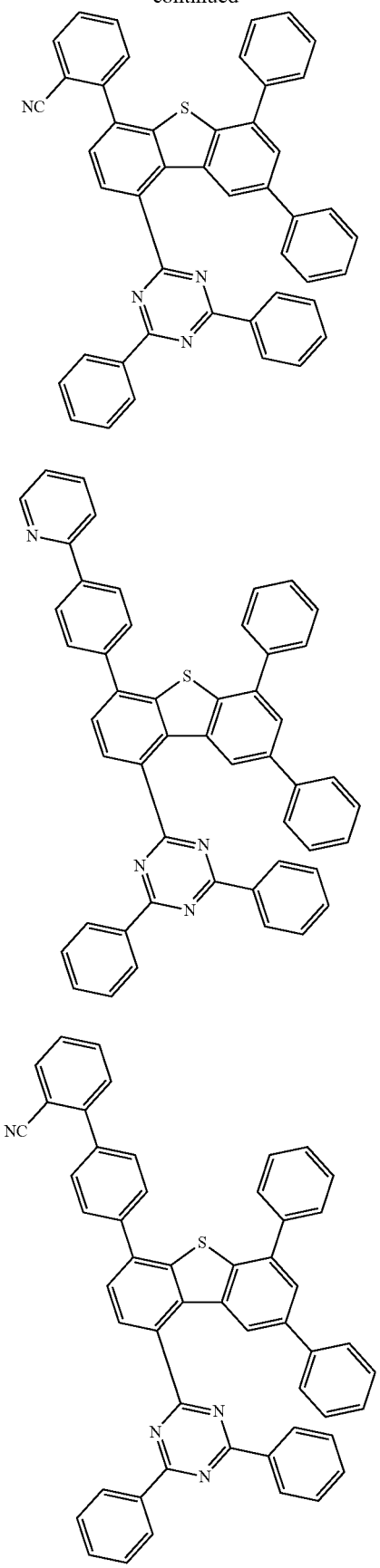
-continued
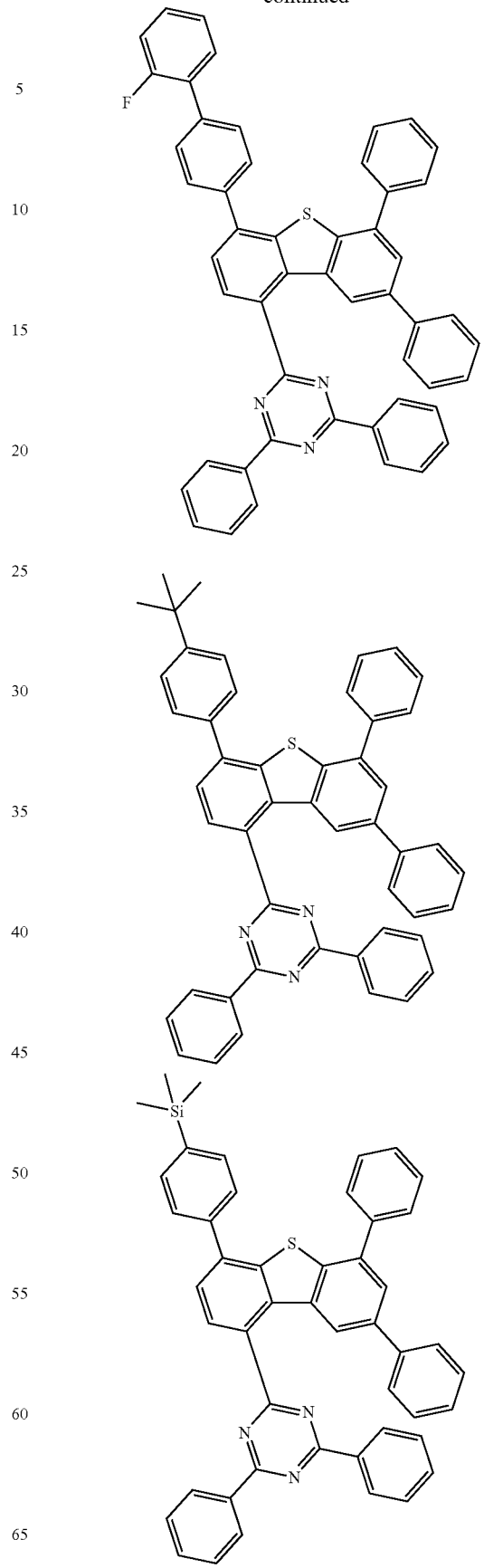

-continued
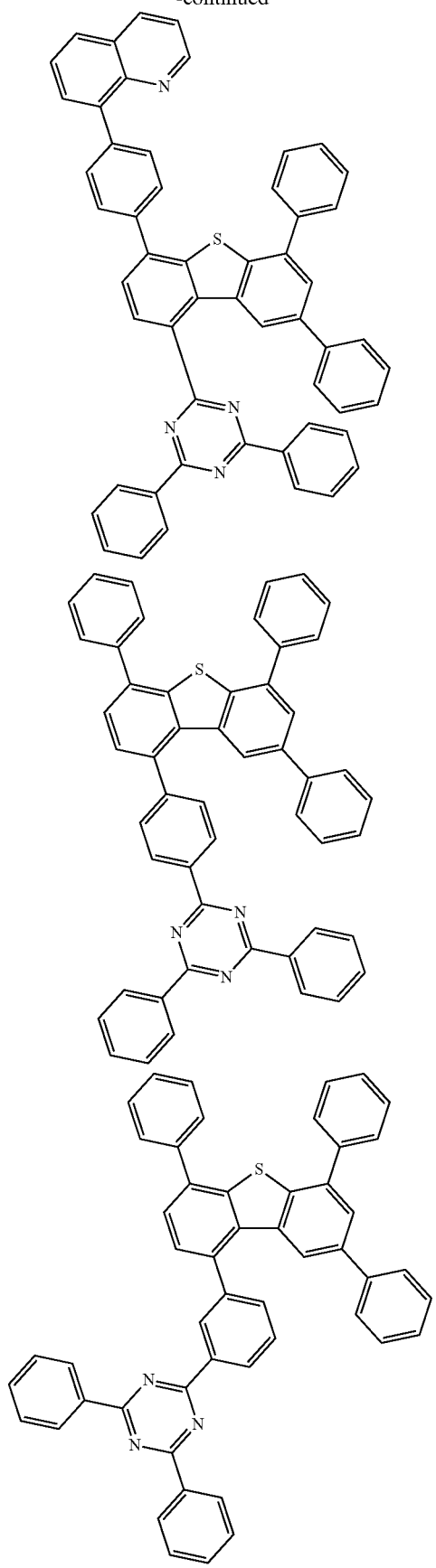
-continued
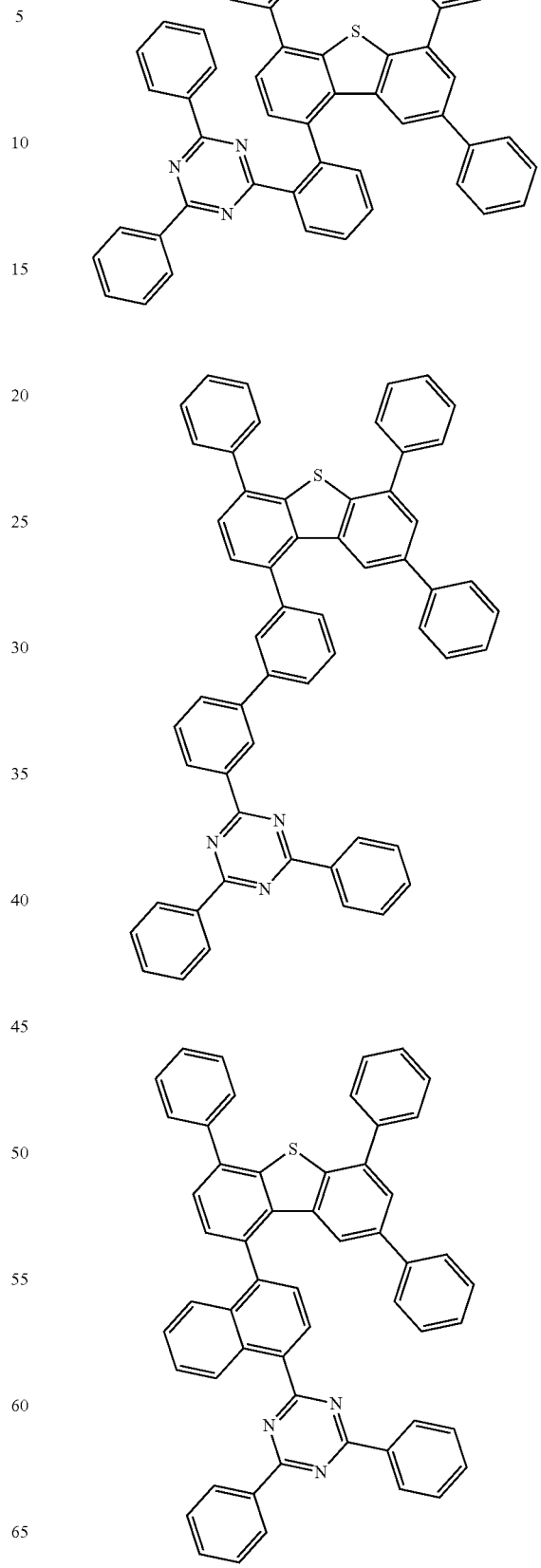

37
-continued
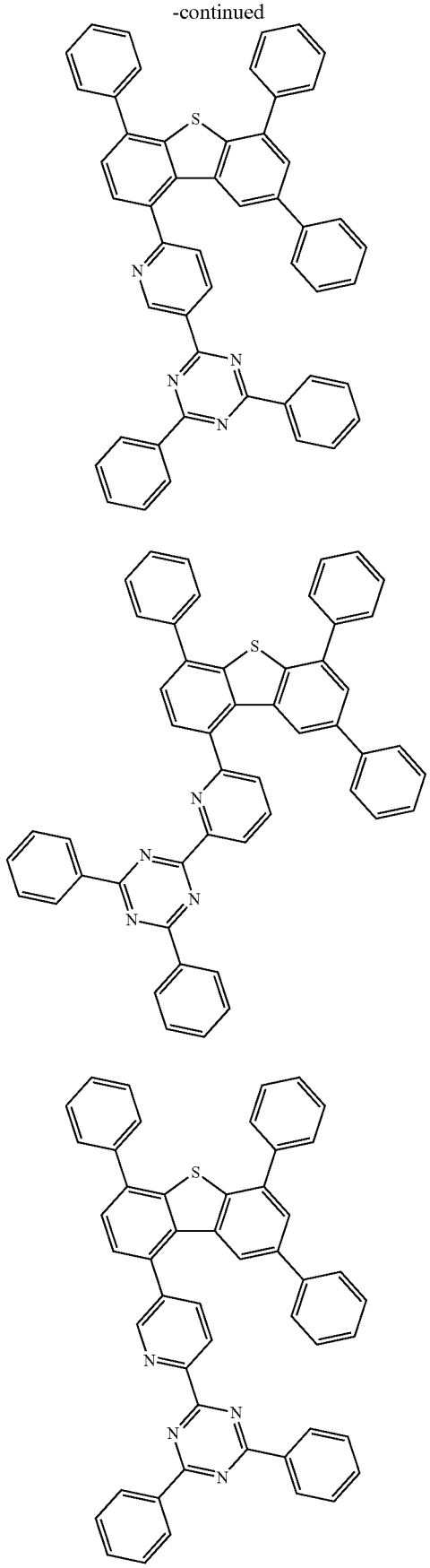
38
-continued
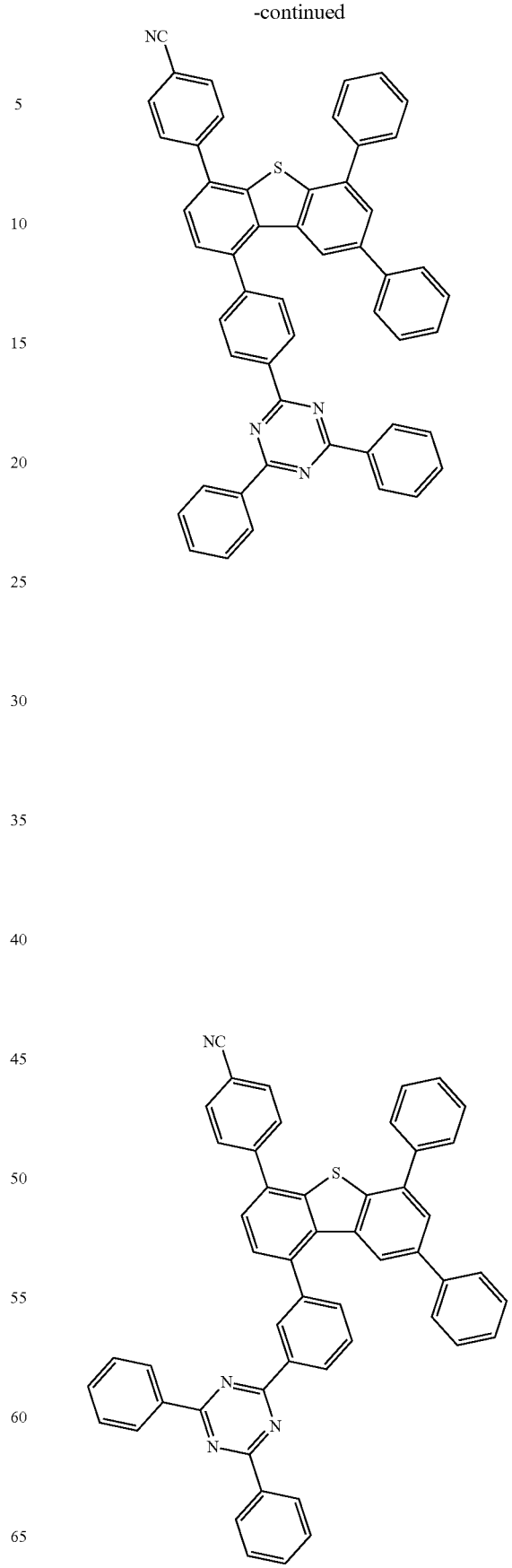

-continued
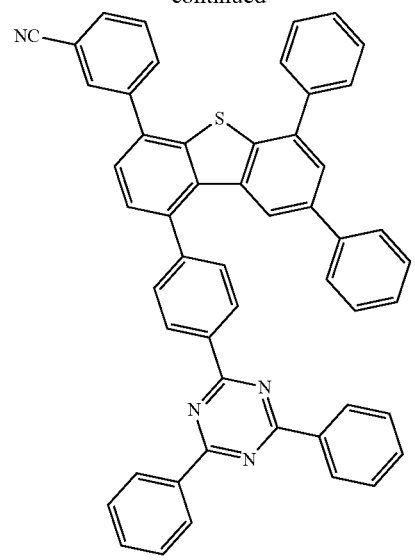
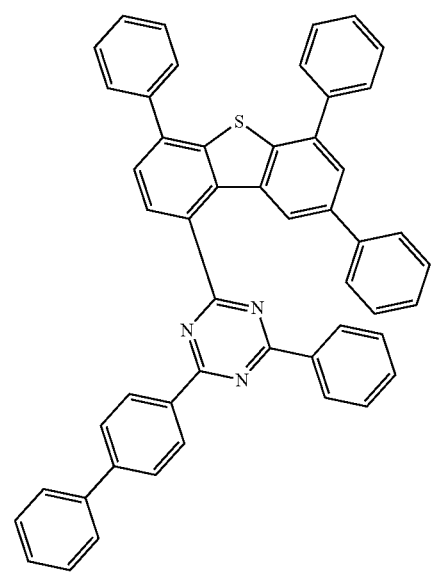
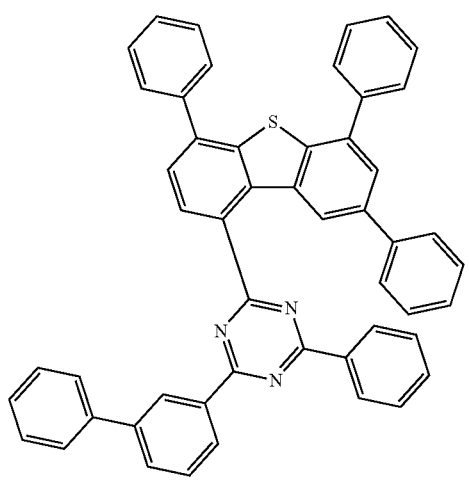
-continued
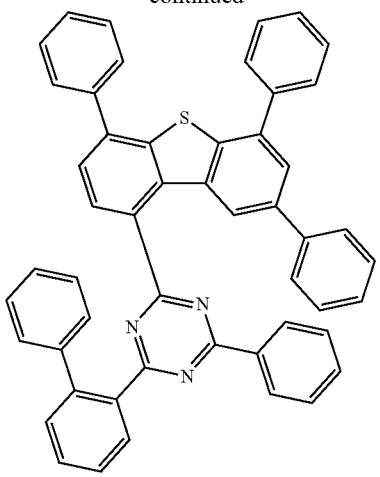
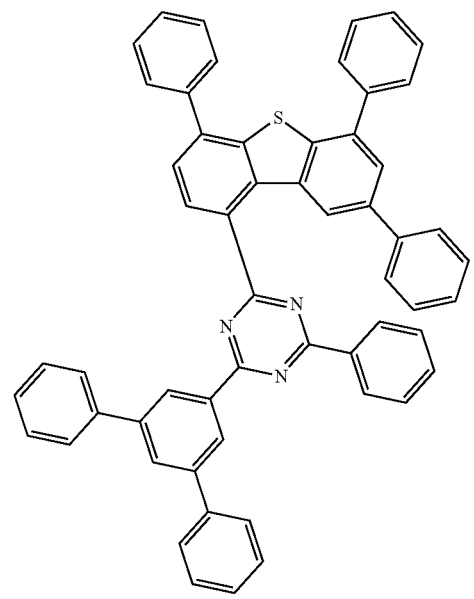
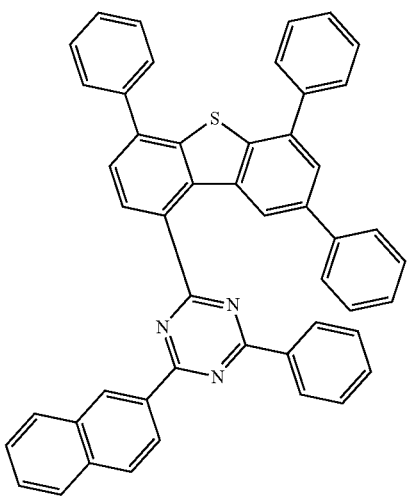

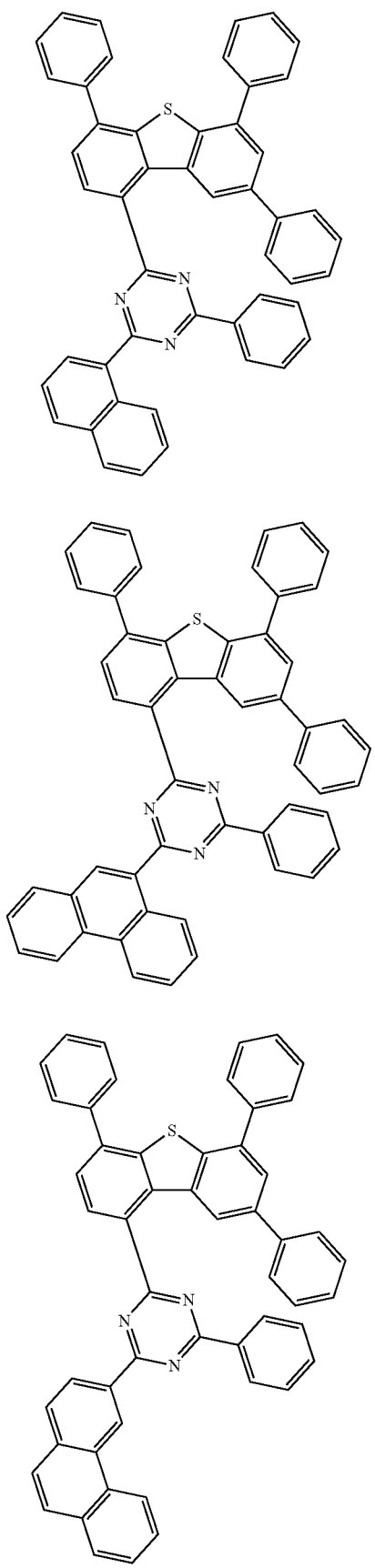
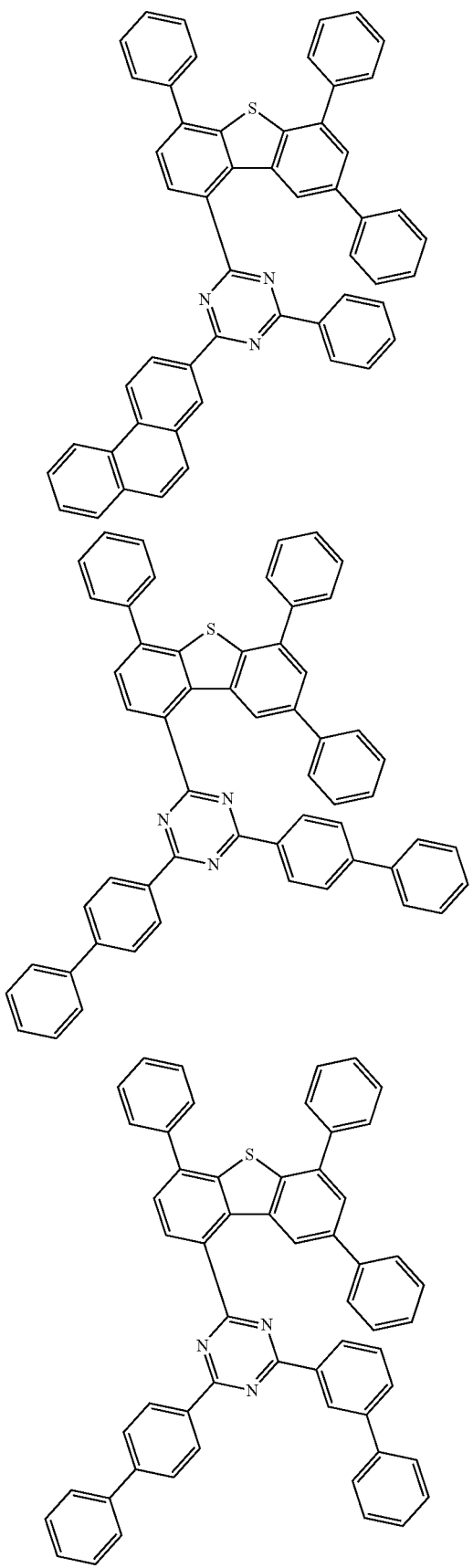

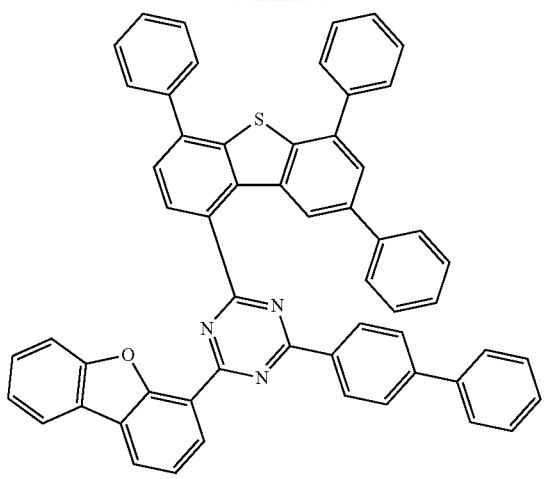
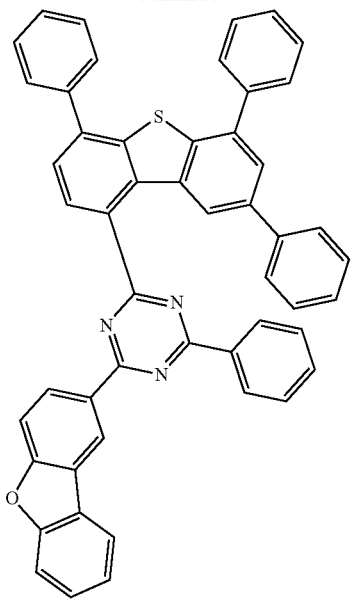

-continued
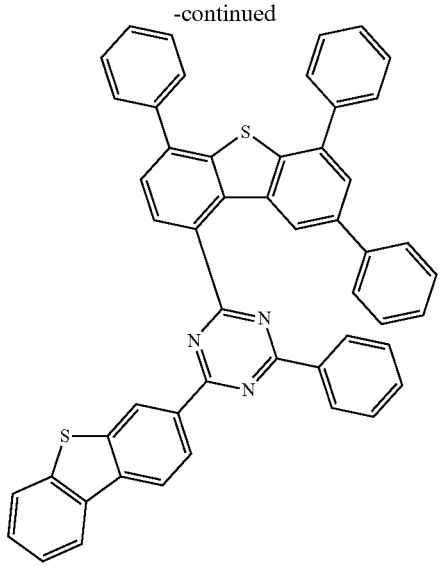
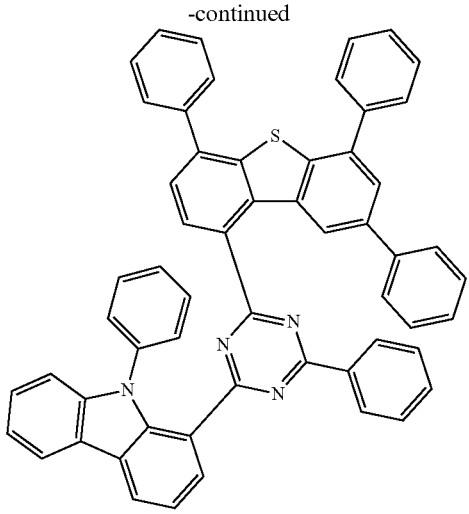
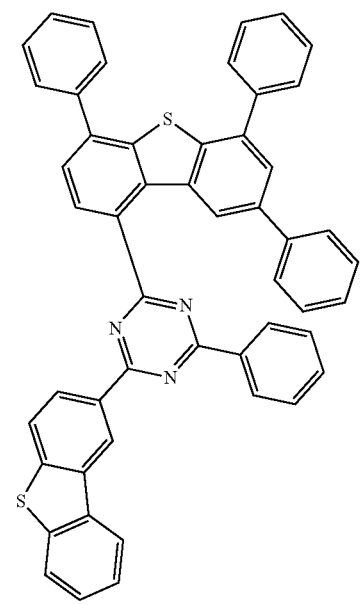
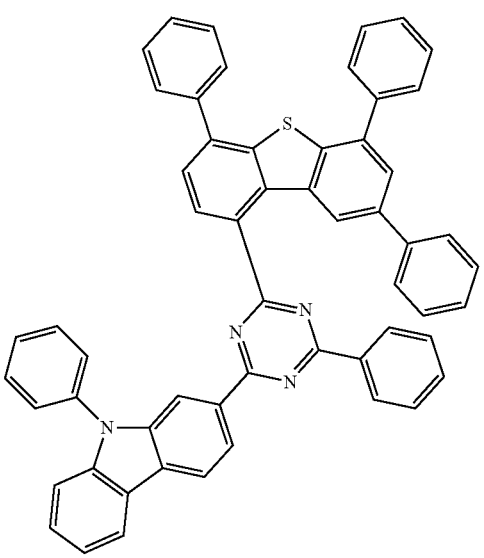
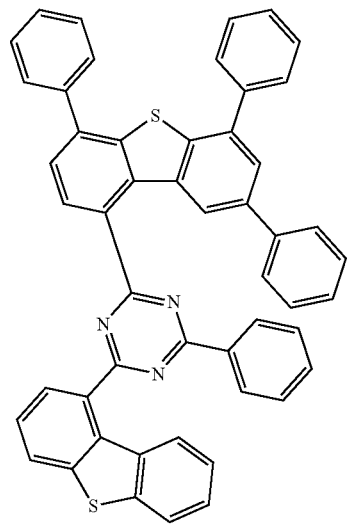
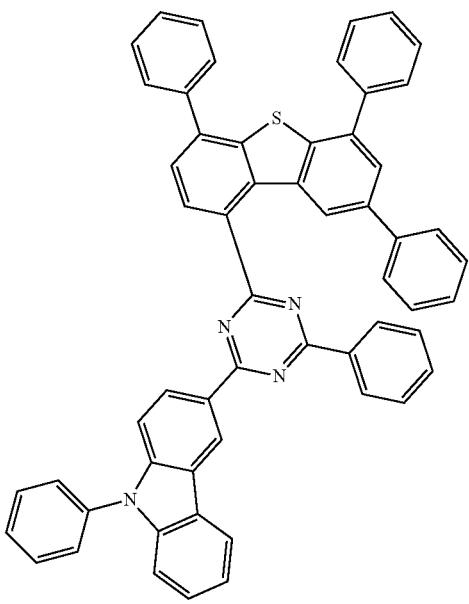

-continued
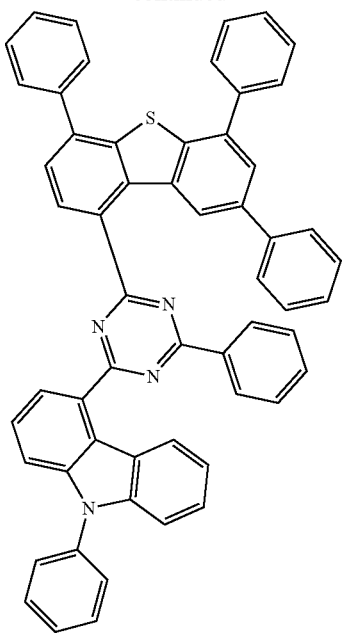
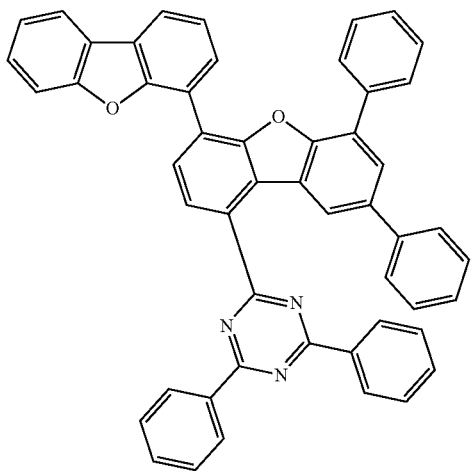
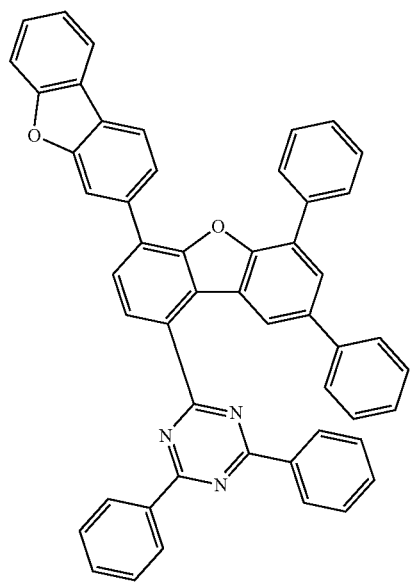
-continued
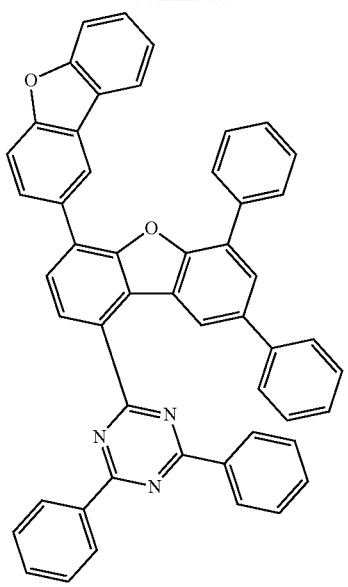
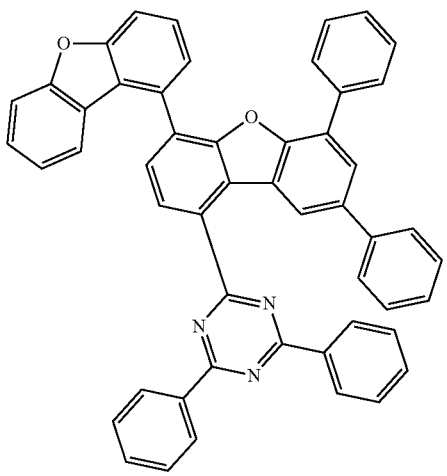
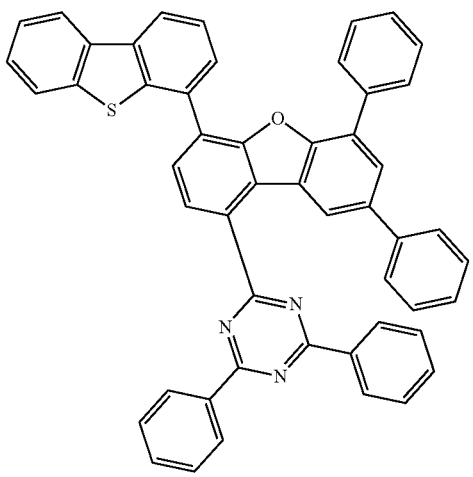

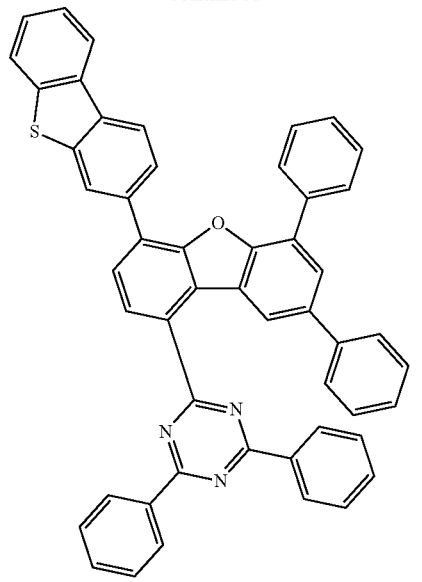
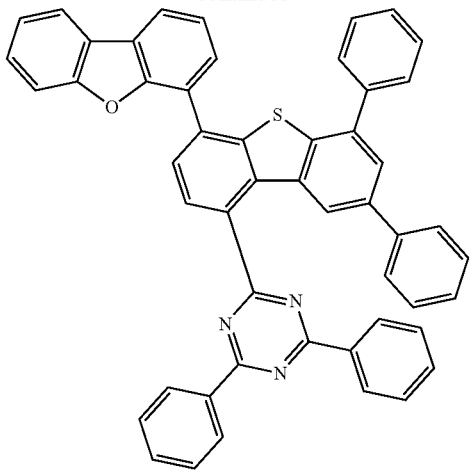
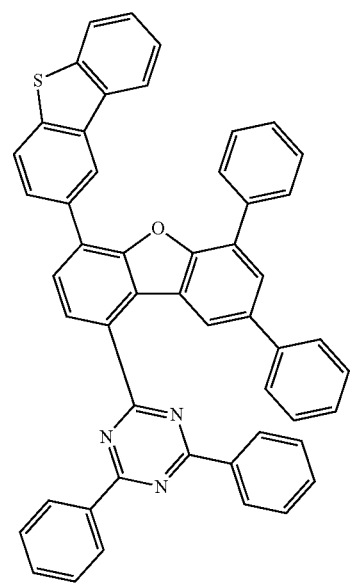
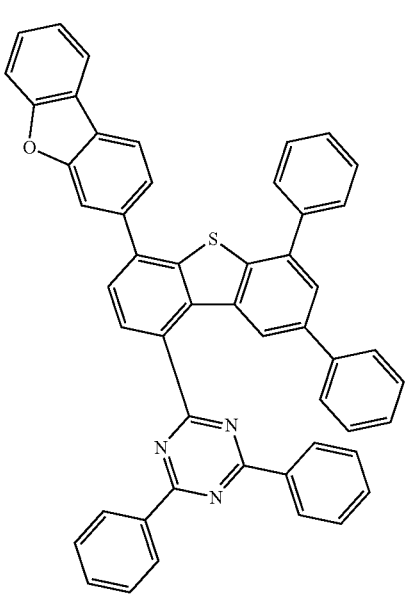
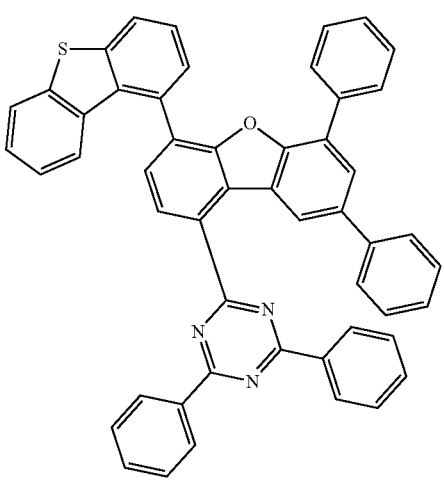
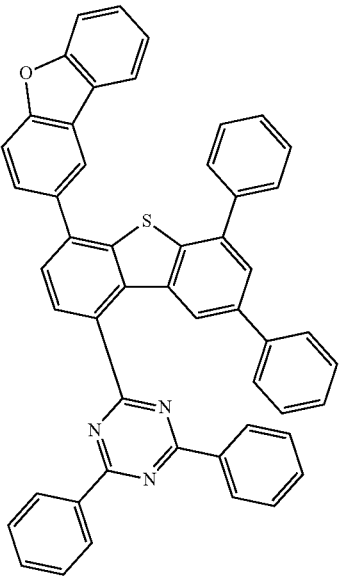

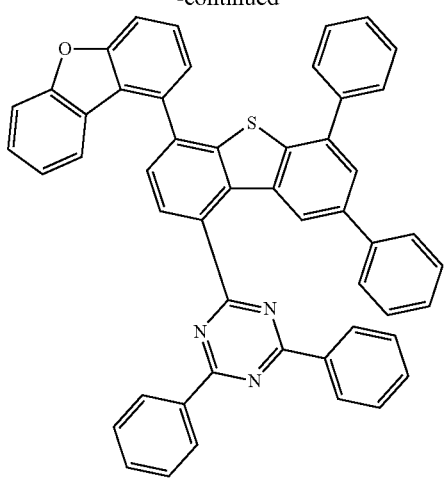
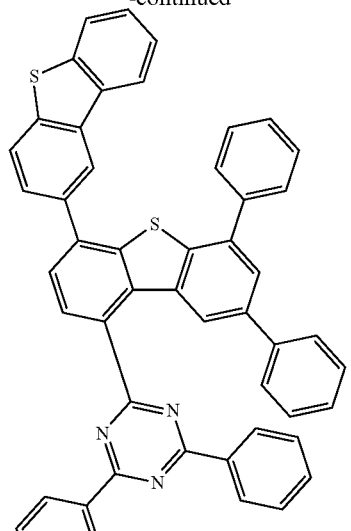
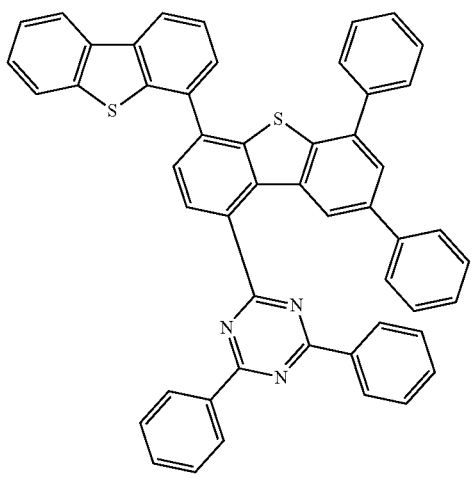
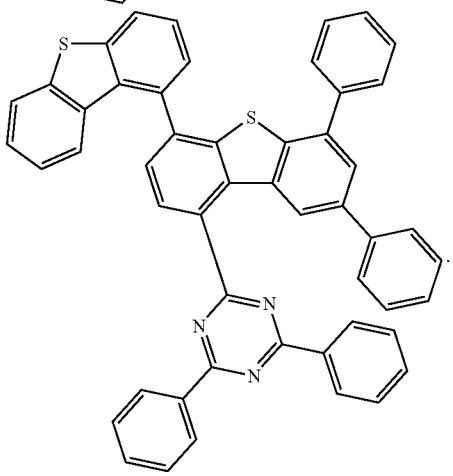
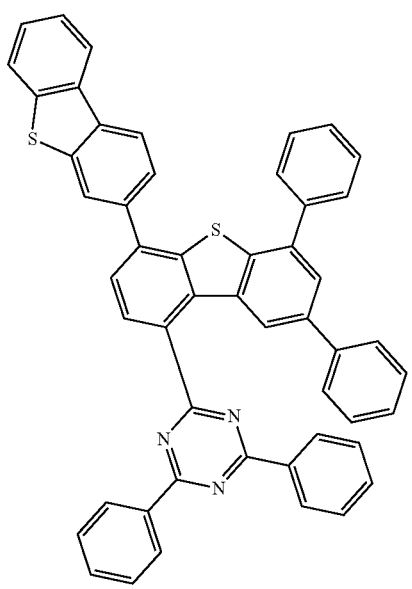
Further, for example, the present disclosure provides a method for preparing the compound of Chemical Formula 1 as shown in the following Reaction Scheme 1:
Reaction Scheme 1
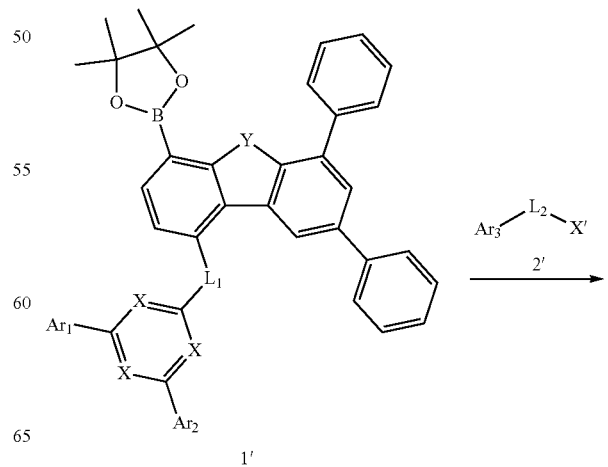

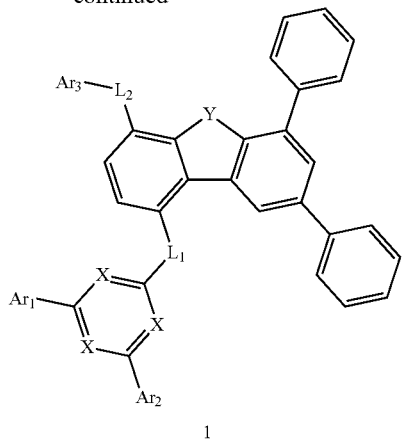

In Reaction Scheme 1, the remaining definitions except X' are as defined above, and X is a halogen, preferably bromo or chloro. The reaction is a Suzuki coupling reaction, which is preferably carried out in the presence of a palladium catalyst and a base, and the reactive group for the Suzuki coupling reaction can be modified as known in the art. The above preparation method can be further specified in preparation examples to be described later.

Further, the present disclosure provides an organic light emitting device including: a first electrode; a second electrode provided opposite to the first electrode; and one or more organic material layers provided between the first electrode and the second electrode, wherein one or more layers of the organic material layers includes the compound of Chemical Formula 1.

The organic material layer of the organic light emitting device of the present disclosure can have a single layer structure, or it can have a multilayered structure in which two or more organic material layers are stacked. For example, the organic light emitting device of the present disclosure can have a structure including a hole injection layer, a hole transport layer, a light emitting layer, an electron transport layer, an electron injection layer, and the like as the organic material layer. However, the structure of the organic light emitting device is not limited thereto, and it can include a smaller number of organic layers.

In addition, the organic layer can include a light emitting layer, and the light emitting layer includes the compound of Chemical Formula 1. In particular, the compound according to the present disclosure can be used as a dopant of the light emitting layer.

In addition, the organic layer can include an electron transport layer or an electron injection layer, and the electron transport layer or the electron injection layer includes the compound of Chemical Formula 1.

In addition, the electron transport layer, the electron injection layer, or a layer for the electron transport and electron injection at the same time includes the compound of Chemical Formula 1.

In addition, the organic material layer can include a light emitting layer and an electron transport layer, and the electron transport layer can include the compound of Chemical Formula 1.

Further, the organic light emitting device according to the present disclosure can be a normal type of organic light emitting device in which an anode, one or more organic material layers, and a cathode are sequentially stacked on a substrate. Further, the organic light emitting device according to the present disclosure can be an inverted type of organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device including a substrate 1, an anode 2, a light emitting layer 3, and a cathode 4. In such a structure, the compound of Chemical Formula 1 can be included in the light emitting layer.

FIG. 2 shows an example of an organic light emitting device including a substrate 1, an anode 2, a hole injection layer 5, a hole transport layer 6, a light emitting layer 7, an electron transport layer 8, and a cathode 4. In such a structure, the compound of Chemical Formula 2 can be included in one or more layers of the hole injection layer, the hole transport layer, the light emitting layer, and the electron transport layer.

The organic light emitting device according to the present disclosure can be manufactured by materials and methods known in the art, except that one or more layers of the organic material layers include the compound of Chemical Formula 1. Further, when the organic light emitting device includes a plurality of organic material layers, the organic material layers can be formed of the same material or different materials.

For example, the organic light emitting device according to the present disclosure can be manufactured by sequentially stacking a first electrode, an organic material layer, and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon. In addition to such a method, the organic light emitting device can be manufactured by sequentially depositing a cathode material, an organic material layer, and an anode material on a substrate.

In addition, the compound of Chemical Formula 1 can be formed into an organic layer by a solution coating method as well as a vacuum deposition method at the time of manufacturing an organic light emitting device. Herein, the solution coating method means spin coating, dip coating, doctor blading, inkjet printing, screen printing, a spray method, roll coating, or the like, but is not limited thereto.

In addition to such a method, the organic light emitting device can be manufactured by sequentially depositing a cathode material, an organic material layer, and an anode material on a substrate (WO 2003/012890). However, the manufacturing method is not limited thereto.

As an example, the first electrode is an anode and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include: metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or SnO$_2$:Sb; conductive polymers such as poly(3-methylthiophene), poly[3,4-(ethylene-1,2-dioxy)thiophene] (PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or LiO$_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, a polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence.

Specific examples of the light emitting material include: an 8-hydroxy-quinoline aluminum complex (Alq3); a carbazole-based compound; a dimerized styryl compound; BAlq; a 10-hydroxybenzoquinoline-metal compound; a benzoxazole, benzothiazole and benzimidazole-based compound; a poly(p-phenylene vinylene) (PPV)-based polymer; a spiro compound; polyfluorene; rubrene; and the like, but are not limited thereto.

The light emitting layer can include a host material and a dopant material. The host material can be a fused aromatic ring derivative, a heterocycle-containing compound, or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene, and the like, which have an arylamino group. The styrylamine compound is a compound where at least one arylvinyl group is substituted in a substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer, and has large mobility for electrons. Specific examples of the electron transport material include: an Al complex of 8-hydroxyquinoline; a complex including Alq3; an organic radical compound; a hydroxyflavone-metal complex; and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxy-benzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)-(2-naphtholato)gallium, and the like, but are not limited thereto.

The organic light emitting device according to the present disclosure can be a front side emission type, a back side emission type, or a double side emission type according to the used material.

Further, the compound of Chemical Formula 1 can be included in an organic solar cell or an organic transistor in addition to an organic light emitting device.

The preparation of the compound of Chemical Formula 1 and the organic light emitting device including the same will be described in detail in the following examples. However, these examples are presented for illustrative purposes only, and the scope of the present disclosure is not limited thereto.

PREPARATION EXAMPLES

Preparation Example 1: Preparation of Compound 1-2

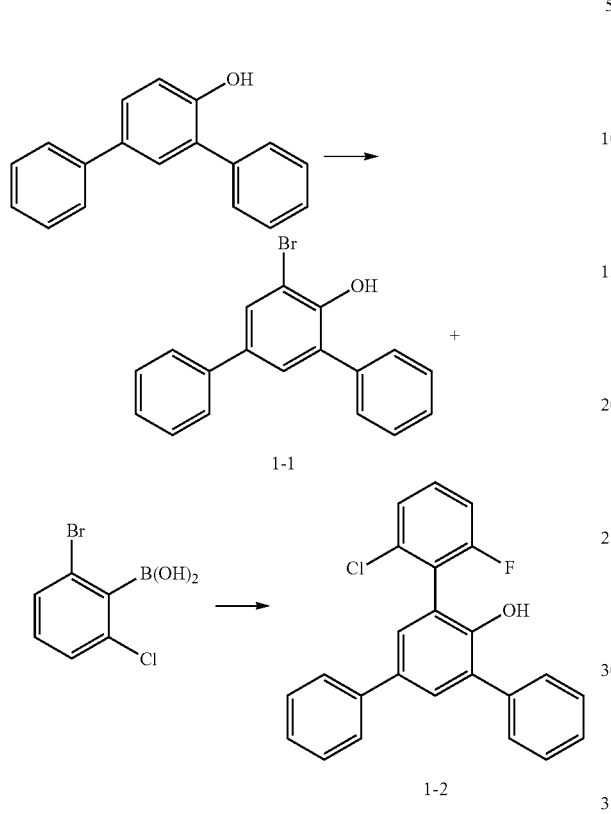

Preparation Example 2: Preparation of Compound 1-4

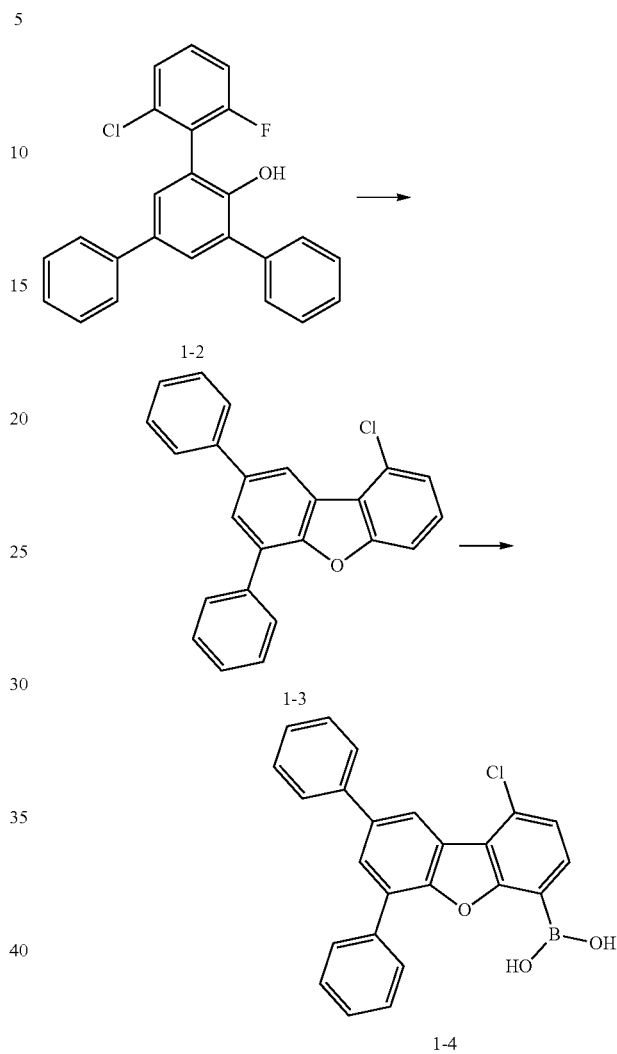

1) Preparation of Compound 1-1

[1,1':3',1''-terphenyl]-4'-ol (50.0 g, 203 mmol) was dissolved in chloroform (500 mL) and cooled to 0° C. Thereafter, N-bromosuccinimide (38.0 g, 213 mmol) was added in portions. After slowly warming it up, it was stirred for 1 hour at room temperature. After completion of the reaction, it was washed once with a sodium thiosulfate solution and once with water, dried over magnesium sulfate, and filtered. The filtrate was distilled under reduced pressure, and purified by column chromatography to give the compound 1-1 (45.4 g, yield 69%).

MS:$[M+H]^+$=323

2) Preparation of Compound 1-2

The previously prepared Compound 1-1 (45.4 g, 140.1 mmol) and (2-chloro-6-fluorophenyl)boronic acid (26.8 g, 154.1 mmol) were dissolved in tetrahydrofuran (400 mL). Sodium carbonate ($Na_2CO_3$) (2 M solution) (120 mL) and tetrakis(triphenylphosphine)palladium(0) [$Pd(PPh_3)_4$] (4.9 g, 4.2 mmol) were added and refluxed for 8 hours. After the reaction was completed, the mixture was cooled to room temperature, and the organic layer was separated and distilled. After distillation, the mixture was extracted three times with toluene and water. The toluene layer was separated, dried over magnesium sulfate, distilled under reduced pressure, and purified by column chromatography using chloroform and ethyl acetate to obtain Compound 1-2 (26.7 g, yield 51%).

MS:$[M+H]^+$=375

1) Preparation of Compound 1-3

The previously prepared Compound 1-2 (26.7 g, 71.5 mmol) was dissolved in distilled dimethylformamide (200 mL). It was then cooled to 0° C., and sodium hydride (2.1 g, 85.7 mmol) was slowly added dropwise thereto. After stirring for 20 minutes, the mixture was stirred at 100° C. for 1 hour. After the reaction was completed, the temperature was cooled to room temperature, and a mixture of ethanol (100 mL) and water (300 mL) was slowly added. The mixture obtained by distillation under reduced pressure was recrystallized with chloroform and ethyl acetate to prepare Compound 1-3 (16.7 g, yield 66%).

MS:$[M+H]^+$=355

2) Preparation of Compound 1-4

The previously prepared Compound 1-3 (16.7 g, 47.2 mmol) was dissolved in tetrahydrofuran (200 mL), the temperature was lowered to −78° C., and 1.7 M n-butyllithium (22.6 mL, 56.6 mmol) was slowly added. After stirring at the same temperature for 1 hour, the temperature was raised to room temperature, followed by stirring for 5 hours, and cooled to −78° C. again. Then, triisopropyl borate (B(OiPr)$_3$) (28.3 mL, 213.1 mmol) was added and stirred for 3 hours while gradually raising the temperature to room temperature. A 2 N aqueous hydrochloric acid solution (200 mL) was added to the reaction mixture, and it was stirred for 1.5 hours at room temperature. The resulting precipitate was filtered off, washed successively with water and ethyl ether, and dried under vacuum. After drying, the mixture was dispersed in ethyl ether, stirred for 2 hours, filtered, and dried to prepare Compound 1-4 (15.2 g, yield 81%).

MS:[M+H]$^+$=399

Preparation Example 3: Preparation of Compound 1-6

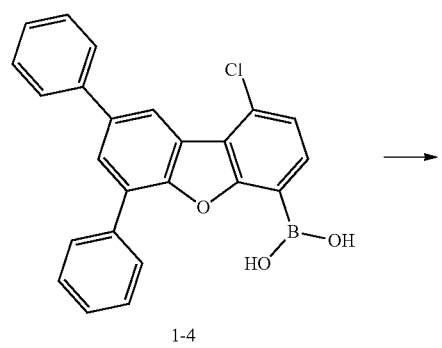

1-4

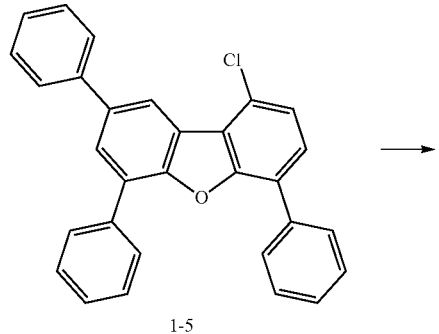

1-5

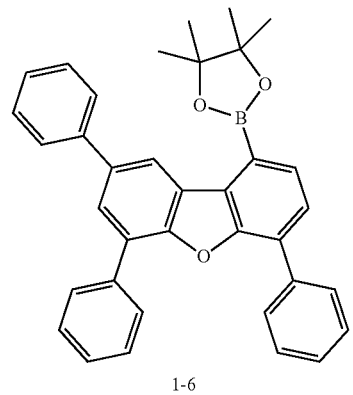

1-6

1) Preparation of Compound 1-5

The previously prepared Compound 1-4 (15.2 g, 38.2 mmol) and bromobenzene (7.1 g, 45.8 mmol) prepared above were dispersed in tetrahydrofuran (150 mL), and a 2 M aqueous potassium carbonate solution (aq. K$_2$CO$_3$) (32 mL) was added. Tetrakis(triphenylphosphine)palladium(0) [Pd(PPh$_3$)$_4$](1.3 g, 3 mol %) was added, and stirred under reflux for 4 hours. The temperature was lowered to room temperature and the resulting solid was filtered. The filtered solid was recrystallized with tetrahydrofuran and ethyl acetate, then filtered and dried to prepare Compound 1-5 (12.6 g, yield 77%).

MS:[M+H]$^+$=431

2) Preparation of Compound 1-6

The previously prepared Compound 1-5 (12.6 g, 52.9 mmol), bis(pinacolato)diboron (14.8 g, 58.2 mmol), potassium acetate (15.6 g, 158.8 mmol), dibenzylideneacetonepalladium (0.9 g, 1.6 mmol) and tricyclohexylphosphine (0.9 g, 3.2 mmol) were added to dioxane (200 mL) and refluxed for 12 hours.

After the reaction was completed, the mixture was cooled to room temperature and then distilled under reduced pressure to remove the solvent. This was dissolved in chloroform and washed three times with water, and then the organic layer was separated and dried over magnesium sulfate. Compound 1-6 (15.4 g, yield 88%) was prepared by distillation under reduced pressure.

MS:[M+H]$^+$=331

EXAMPLES

Example 1: Preparation of Compound 1

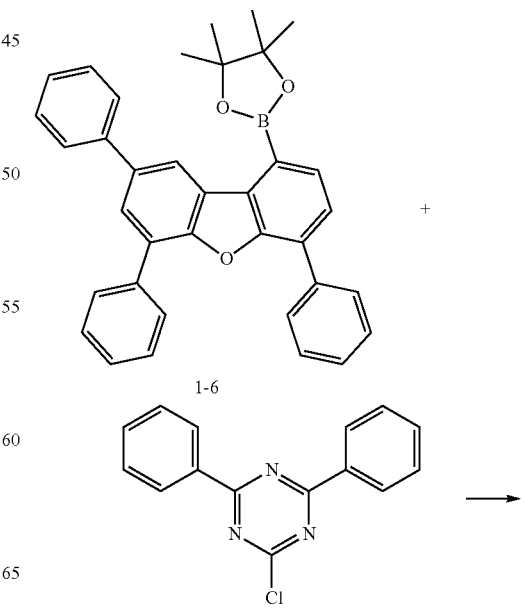

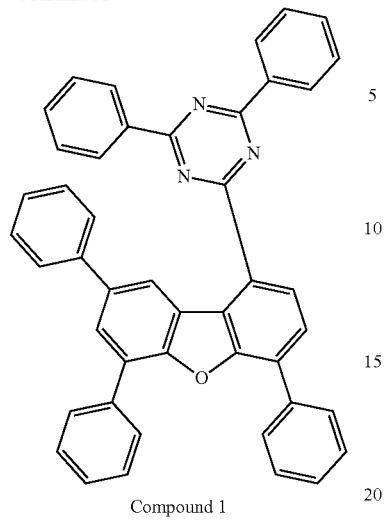

Compound 1

In a nitrogen atmosphere, Compound 1-6 (10.0 g, 19.1 mmol) and 2-chloro-4,6-diphenyl-1,3,5-triazine (5.1 g, 19.1 mmol) were added to dioxane (100 mL), and stirred under reflux. Thereafter, potassium carbonate (7.9 g, 57.5 mmol) dissolved in water (40 mL) was added thereto. After being sufficiently stirred, bis(tri-t-butylphosphine)palladium(0) (0.3 g, 0.6 mmol) was added thereto. After reacting for 2 hours, the temperature was cooled to room temperature, and the resultant product was filtered. The filtrate was extracted with chloroform and water, and the organic layer was dried over magnesium sulfate. Thereafter, the organic layer was distilled under reduced pressure, and then recrystallized using a tetrahydrofuran and ethyl acetate mixed solution. The resultant solid was filtered and dried to prepare Compound 1 (8.4 g, yield 71%).

MS:[M+H]$^+$=621

Example 2: Preparation of Compound 2

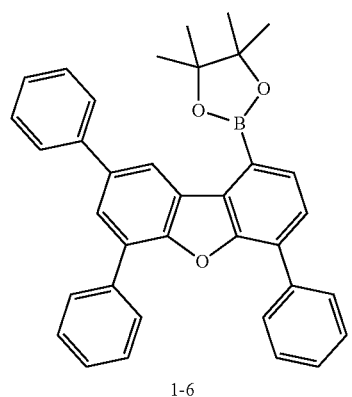

1-6

+

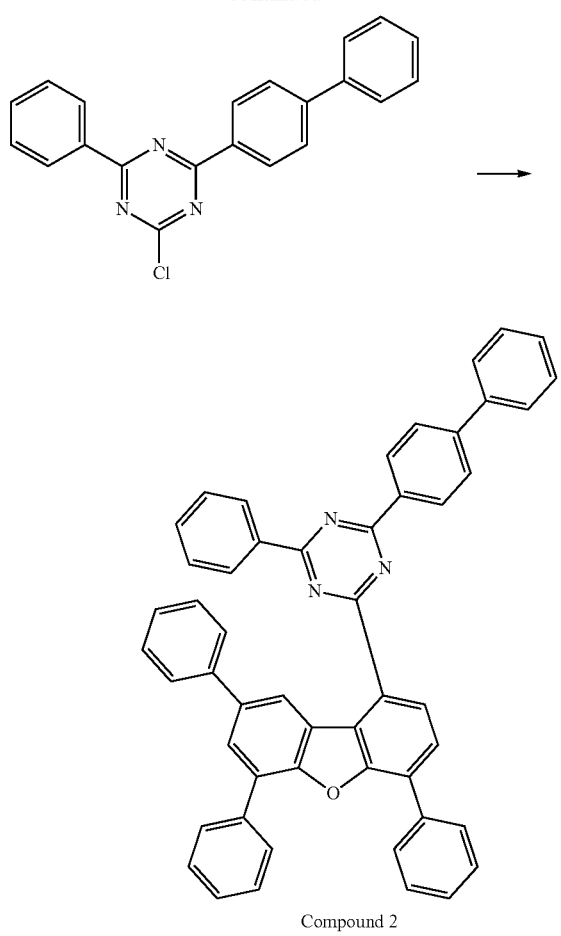

Compound 2

Compound 2 (10.9 g, yield 81%) was prepared in the same manner as in Preparation of Compound 1, except that 2-([1,1'-biphenyl]-4-yl)-4-chloro-6-phenyl-1,3 was used instead of 2-chloro-4,6-diphenyl-1,3,5-triazine.

MS:[M+H]$^+$=704

Example 3: Preparation of Compound 3

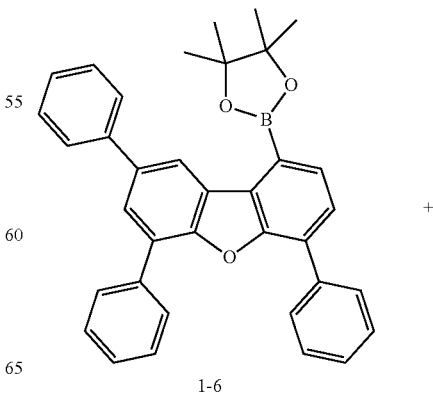

1-6

+

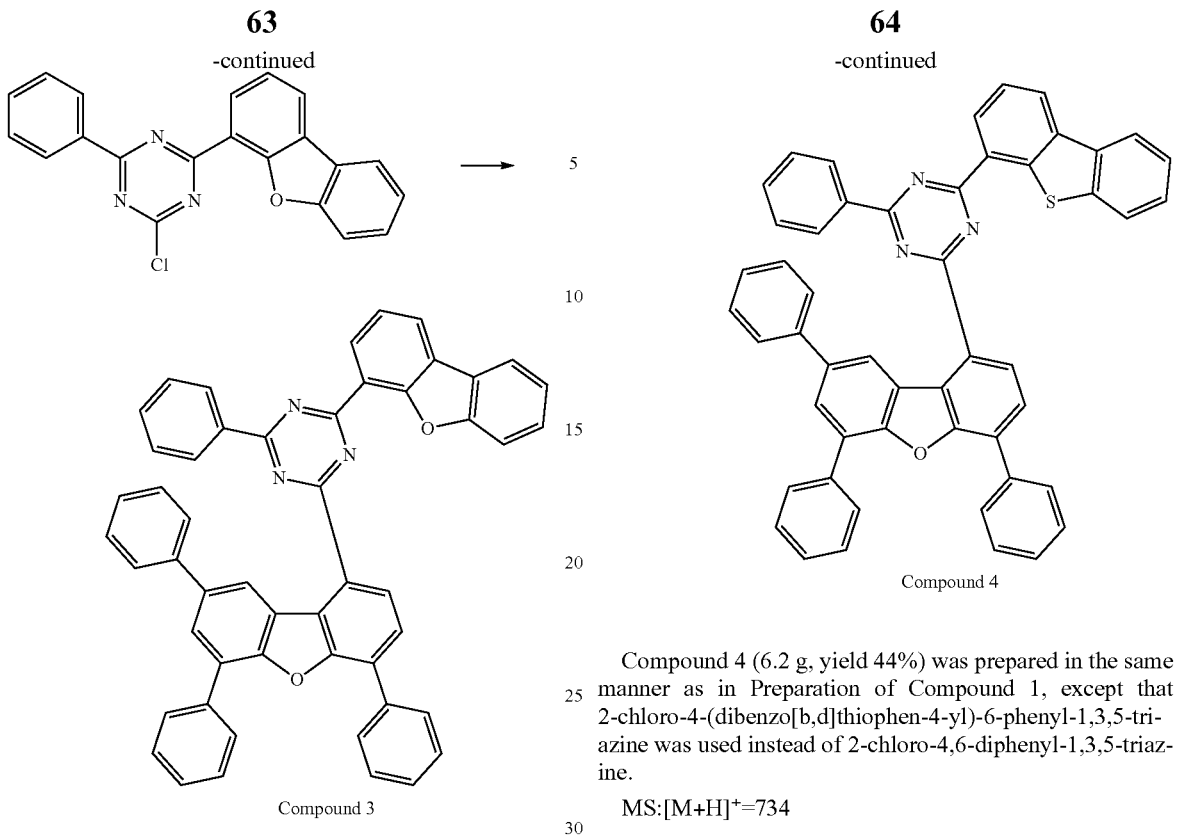

Compound 3

Compound 3 (8.8 g, yield 64%) was prepared in the same manner as in Preparation of Compound 1, except that 2-chloro-4-(dibenzo[b,d]furan-4-yl)-6-phenyl-1,3,5-triazine was used instead of 2-chloro-4,6-diphenyl-1,3,5-triazine.

MS:[M+H]$^+$=718

Example 4: Preparation of Compound 4

Compound 4

Compound 4 (6.2 g, yield 44%) was prepared in the same manner as in Preparation of Compound 1, except that 2-chloro-4-(dibenzo[b,d]thiophen-4-yl)-6-phenyl-1,3,5-triazine was used instead of 2-chloro-4,6-diphenyl-1,3,5-triazine.

MS:[M+H]$^+$=734

Example 5: Preparation of Compound 5

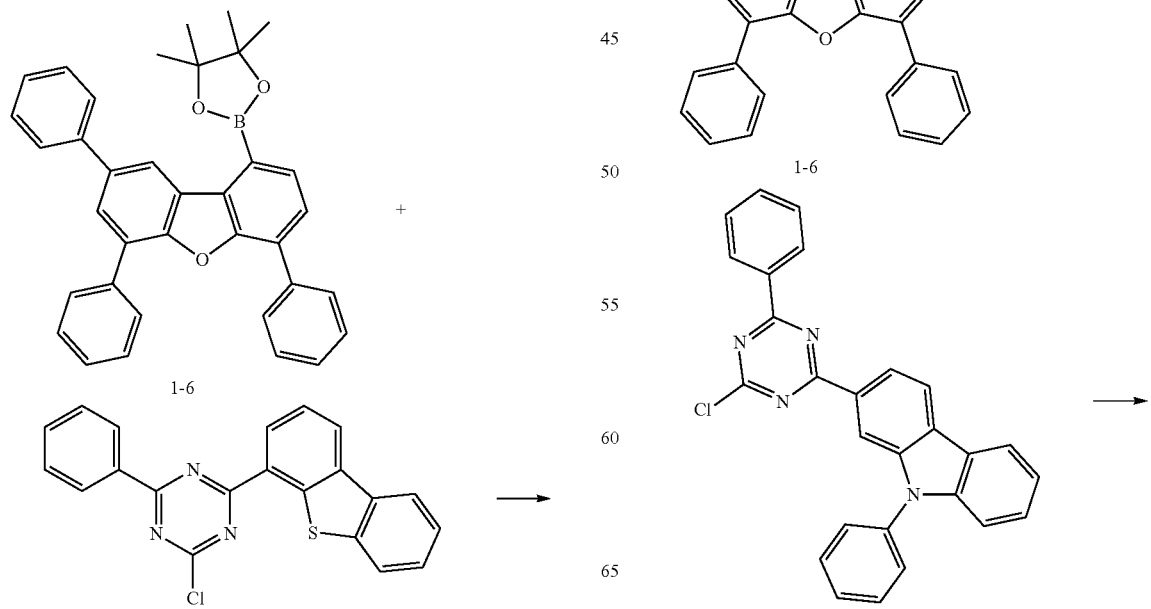

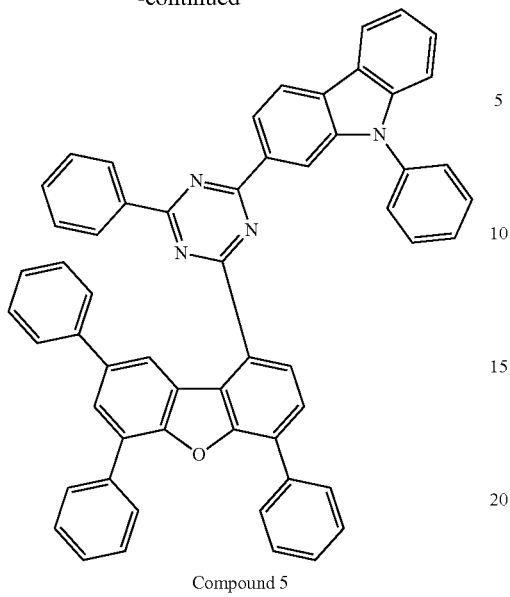

Compound 5

Compound 5 (8.8 g, yield 58%) was prepared in the same manner as in Preparation of Compound 1, except that 2-(4-chloro-6-phenyl-1,3,5-triazin-2-yl)-9-phenyl-9H-carbazole was used instead of 2-chloro-4,6-diphenyl-1,3,5-triazine.

MS:[M+H]$^+$=793

Example 6: Preparation of Compound 6

1) Preparation of Compound 7-2

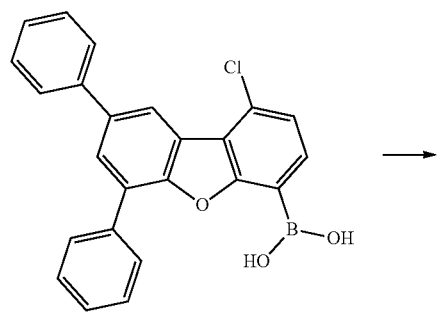

1-4

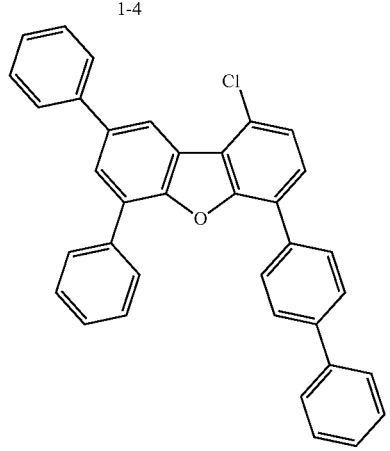

7-1

Compound 1-4 (10.0 g, 32.5 mmol) and 4-bromo-1,1'-biphenyl (7.5 g, 32.5 mmol) were dispersed in tetrahydrofuran (100 mL), a 2 M aqueous potassium carbonate solution (aq. K$_2$CO$_3$) (27 mL) was added thereto, and tetrakis(triphenylphosphine)palladium(0) [Pd(PPh$_3$)$_4$] (0.4 g, 3 mol %) was added thereto, and the mixture was stirred under reflux for 8 hours. The temperature was lowered to room temperature, and the resultant solid was filtered. The filtered solid was recrystallized with tetrahydrofuran and ethyl acetate, filtered, and dried to prepare Compound 7-1 (14.0 g, yield 85%).

MS:[M+H]$^+$=507

The previously prepared Compound 7-1 (14.0 g, 27.7 mmol), bis(pinacolato)diboron (7.7 g, 30.4 mmol), potassium acetate (8.1 g, 82.9 mmol), dibenzylideneacetonepalladium (0.5 g, 0.8 mmol), and tricyclohexylphosphine (0.5 g, 0.8 mmol) were added to dioxane (200 mL) and refluxed for 12 hours. After the reaction was completed, the mixture was cooled to room temperature and then distilled under reduced pressure to remove the solvent. This was dissolved in chloroform and washed three times with water, and then the organic layer was separated and dried over magnesium sulfate. Compound 7-2 (12.7 g, yield 77%) was prepared by distillation under reduced pressure.

MS:[M+H]$^+$=599

2) Preparation of Compound 6

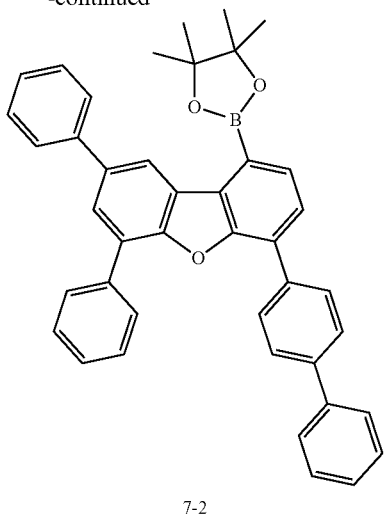

7-2

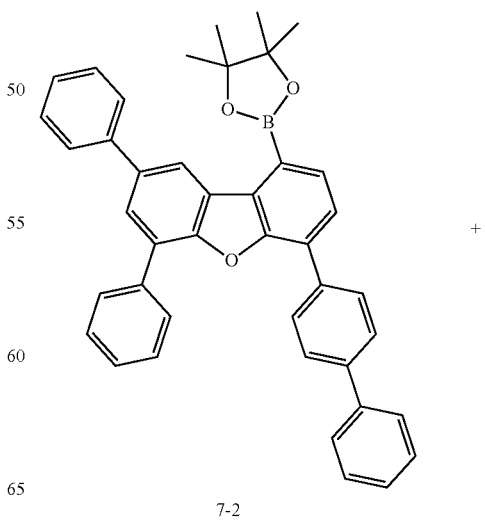

7-2

+

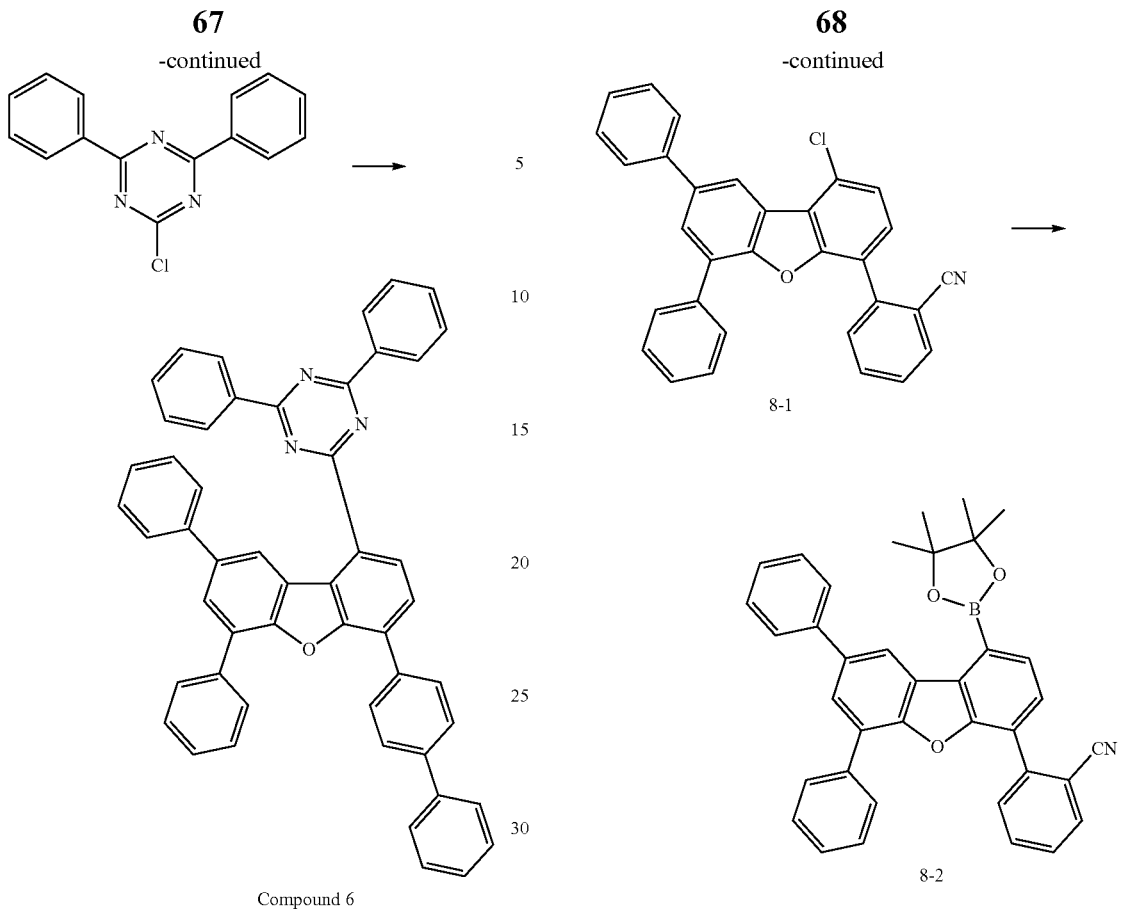

In a nitrogen atmosphere, the previously prepared Compound 7-2 (10.0 g, 16.7 mmol) and 2-chloro-4,6-diphenyl-1,3,5-triazine (4.5 g, 16.7 mmol)) was added to dioxane (100 mL), and the mixture was stirred under reflux. Thereafter, potassium carbonate (6.9 g, 50.1 mmol) dissolved in water (20 mL) was added thereto. After being sufficiently stirred, bis(tri-t-butylphosphine)palladium(0) (0.3 g, 0.5 mmol) was added thereto. After reacting for 2 hours, the temperature was cooled to room temperature, and the resultant product was filtered. The filtrate was extracted with chloroform and water, and then the organic layer was dried using magnesium sulfate. Thereafter, the organic layer was distilled under reduced pressure, and then recrystallized using a tetrahydrofuran and ethyl acetate mixed solution. The resultant solid was filtered and dried to prepare Compound 6 (6.4 g, yield 55%).

MS:[M+H]$^+$=704

Example 7: Preparation of Compound 7

1) Preparation of Compound 8-2

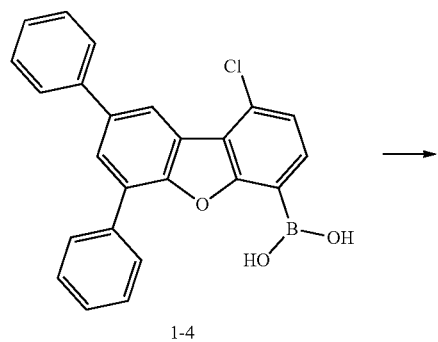

Compound 1-4 (15.0 g, 48.7 mmol) and 2-bromobenzonitrile (8.8 g, 48.7 mmol) were dispersed in tetrahydrofuran (100 mL), a 2 M aqueous potassium carbonate solution (aq. $K_2CO_3$) (73 mL) was added thereto, and tetrakis(triphenylphosphine)palladium(0) [Pd(PPh$_3$)$_4$] (0.6 g, 1 mol %) was added thereto, and the mixture was stirred under reflux for 8 hours. The temperature was cooled to room temperature, and the resultant solid was filtered. The filtered solid was recrystallized with tetrahydrofuran and ethyl acetate, filtered, and dried to prepare Compound 8-1 (15.5 g, yield 70%).

MS:[M+H]$^+$=456

The previously prepared Compound 8-1 (15.5 g, 34.1 mmol), bis(pinacolato)diboron (9.5 g, 37.5 mmol), potassium acetate (10.0 g, 102.2 mmol), dibenzylideneacetonepalladium (0.5 g, 1 mmol), and tricyclohexylphosphine (0.5 g, 2 mmol) were added to dioxane (200 mL), and refluxed for 12 hours. After the reaction was completed, the mixture was cooled to room temperature and then distilled under reduced pressure to remove the solvent. This was dissolved in chloroform and washed three times with water, and then the organic layer was separated and dried over magnesium sulfate. Compound 8-2 (18.7 g, yield 80%) was prepared by distillation under reduced pressure.

MS:[M+H]$^+$=548

2) Preparation of Compound 7

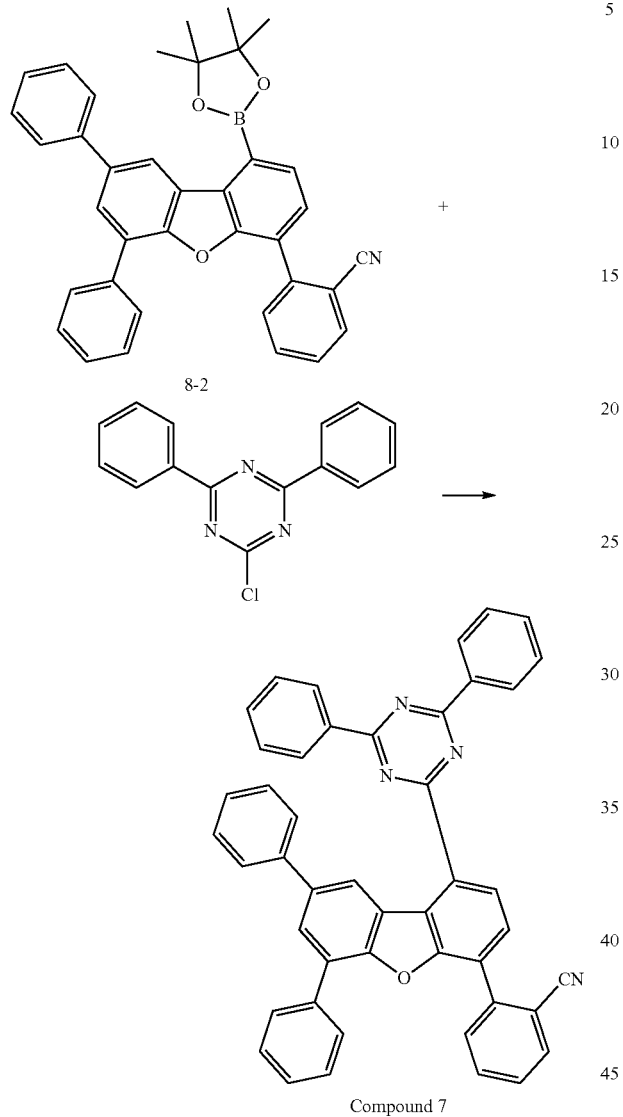

8-2

Compound 7

Example 8: Preparation of Compound 8

1) Preparation of Compound 9-2

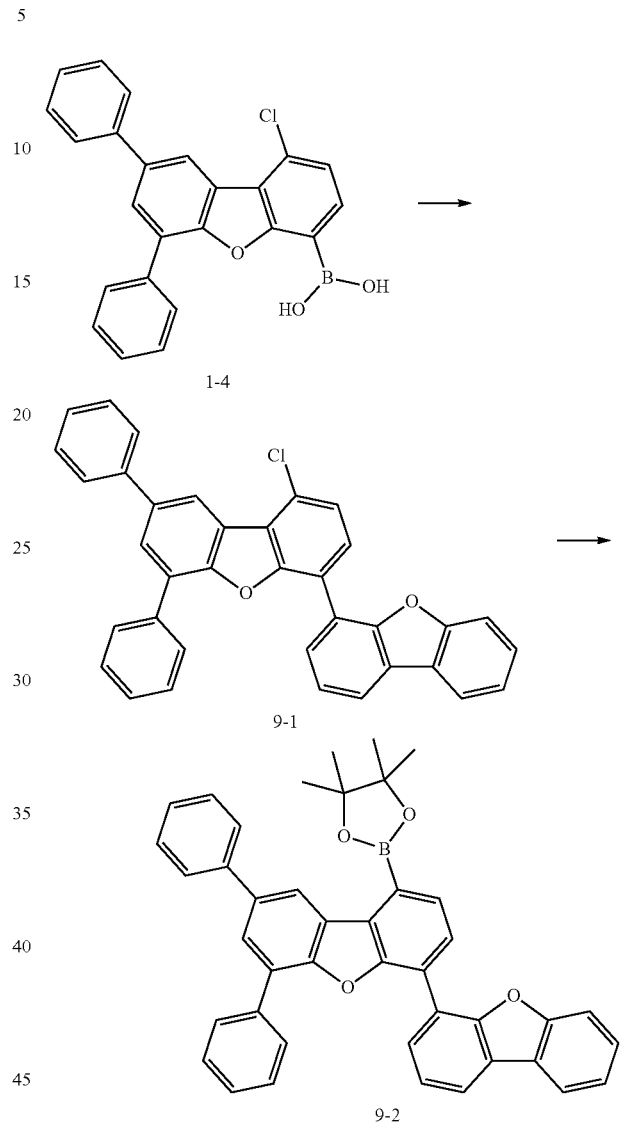

1-4

9-1

9-2

In a nitrogen atmosphere, the previously prepared Compound 8-2 (10.0 g, 16.7 mmol) and 2-chloro-4,6-diphenyl-1,3,5-triazine (4.5 g, 16.7 mmol) were added to dioxane (100 mL), and the mixture was stirred under reflux. Thereafter, potassium carbonate (6.9 g, 50.1 mmol) dissolved in water (20 mL) was added thereto. After being sufficiently stirred, bis(tri-t-butylphosphine)palladium(0) (0.3 g, 0.5 mmol) was added thereto. After reacting for 2 hours, the temperature was cooled to room temperature and filtered. The filtrate was extracted with chloroform and water, and then the organic layer was dried using magnesium sulfate. Thereafter, the organic layer was distilled under reduced pressure, and then recrystallized using a tetrahydrofuran and ethyl acetate mixed solution. The resulting solid was filtered and dried to prepare Compound 7 (6.4 g, yield 55%).

MS:[M+H]$^+$=704

Compound 1-4 (15.0 g, 48.7 mmol) and 4-bromodibenzo[b,d]furan (12.0 g, 48.7 mmol) were dispersed in tetrahydrofuran (100 mL), a 2 M aqueous potassium carbonate solution (aq. K$_2$CO$_3$) (73 mL) was added thereto, and tetrakis(triphenylphosphine)palladium(0) [Pd(PPh$_3$)$_4$] (0.6 g, 1 mol %) was added thereto, and the mixture was stirred under reflux for 8 hours. The temperature was cooled to room temperature and the resulting solid was filtered. The filtered solid was recrystallized with tetrahydrofuran and ethyl acetate, filtered, and dried to prepare Compound 9-1 (16.5 g, yield 65%).

MS:[M+H]$^+$=521

The previously prepared Compound 9-1 (16.5 g, 31.7 mmol), bis(pinacolato)diboron (8.8 g, 34.8 mmol), potassium acetate (9.3 g, 94.9 mmol), dibenzylideneacetonepalladium (0.5 g, 1 mmol), and tricyclohexylphosphine (0.5 g, 2 mmol) were added to dioxane (200 mL), and the mixture was refluxed for 12 hours. After the reaction was completed, the mixture was cooled to room temperature and then distilled under reduced pressure to remove the solvent. This was dissolved in chloroform and washed three times with water, and then the organic layer was separated and dried over magnesium sulfate. Compound 9-2 (13.8 g, yield 71%) was prepared by distillation under reduced pressure.

MS:[M+H]$^+$=613

2) Preparation of Compound 8

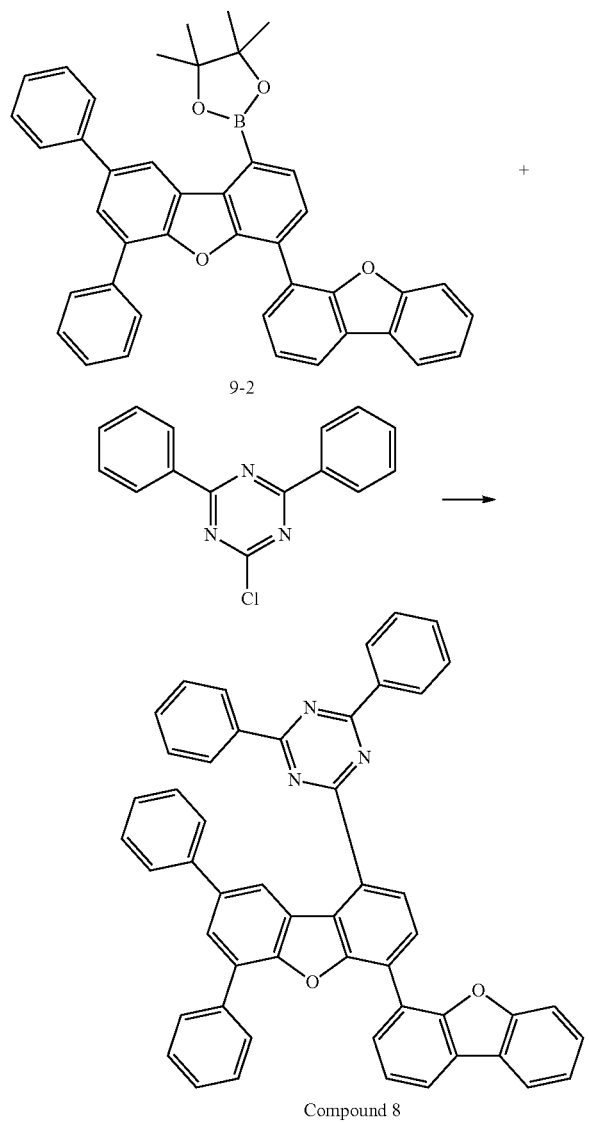

Compound 8

In a nitrogen atmosphere, the previously prepared Compound 9-2 (10.0 g, 16.3 mmol) and 2-chloro-4,6-diphenyl-1,3,5-triazine (4.4 g, 16.3 mmol) were added to dioxane (100 mL), and the mixture was stirred under reflux. Thereafter, potassium carbonate (6.8 g, 49.0 mmol) dissolved in water (20 mL) was added thereto. After being sufficiently stirred, bis(tri-t-butylphosphine)palladium(0) (0.3 g, 0.5 mmol) was added thereto. After reacting for 2 hours, the temperature was cooled to room temperature and filtered. The filtrate was extracted with chloroform and water, and then the organic layer was dried using magnesium sulfate. Thereafter, the organic layer was distilled under reduced pressure and then recrystallized using a tetrahydrofuran and ethyl acetate mixed solution. The resulting solid was filtered and dried to prepare Compound 8 (5.2 g, yield 44%).

MS:[M+H]$^+$=718

EXPERIMENTAL EXAMPLES

Experimental Example 1

A glass substrate on which ITO (indium tin oxide) was coated as a thin film to a thickness of 1300 Å was put into distilled water in which a detergent was dissolved, and ultrasonically cleaned. In this case, a product manufactured by Fischer Co., was used as the detergent, and as the distilled water, distilled water filtered twice using a filter manufactured by Millipore Co., was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, then dried, and then transferred to a plasma cleaner. In addition, the substrate was cleaned for 5 minutes using oxygen plasma, and then transferred to a vacuum depositor.

On the transparent ITO electrode prepared as above, the following compound HI-1 was thermally vacuum-deposited to a thickness of 50 Å to form a hole injection layer. On the hole injection layer, the following compound HT-1 was thermally vacuum-deposited to a thickness of 250 Å to form a hole transport layer. On the hole transport layer, the following compound HT-2 was vacuum-deposited to a thickness of 50 Å to form an electron blocking layer. On the electron blocking layer, the previously prepared Compound 1, the following compound YGH-1, and the following compound YGD-1 were co-deposited in a weight ratio of 44:44:12 to a thickness of 400 Å to form a light emitting layer. On the light emitting layer, the following compound ET-1 was vacuum-deposited to a thickness of 250 Å to form an electron transport layer. On the electron transport layer, the following compounds ET-2 and Li (lithium) were vacuum-deposited at a weight ratio of 98:2 to a thickness of 100 Å to form an electron injection layer. On the electron injection layer, aluminum was deposited to a thickness of 1000 Å to form a cathode.

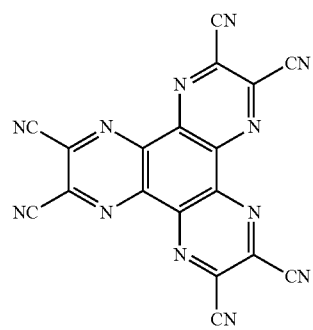

HI-1

HT-1

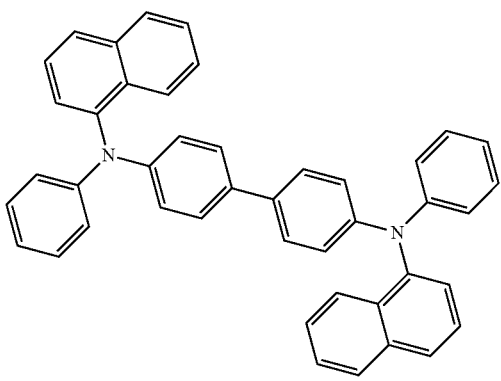

YGD-1

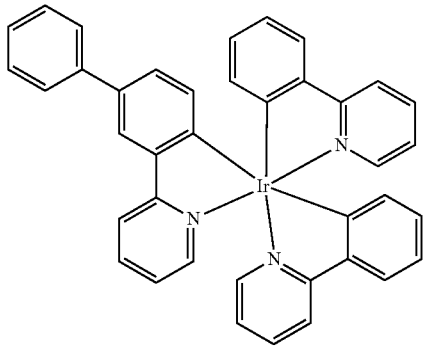

HT-2

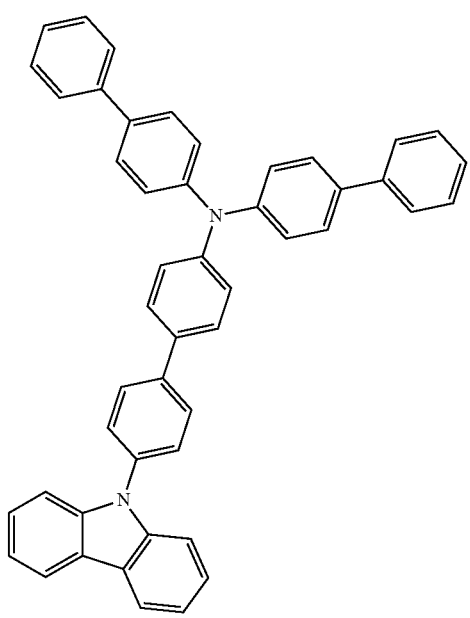

ET-1

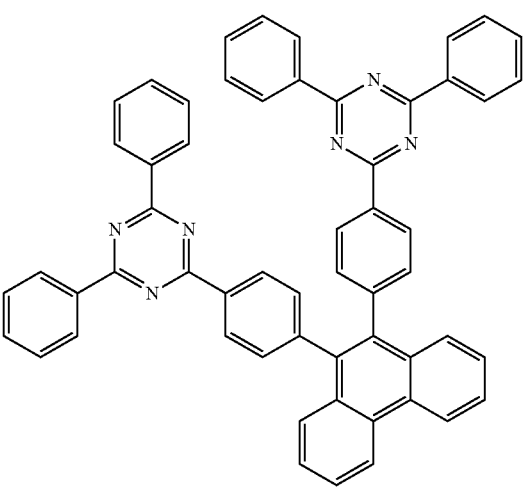

YGH-1

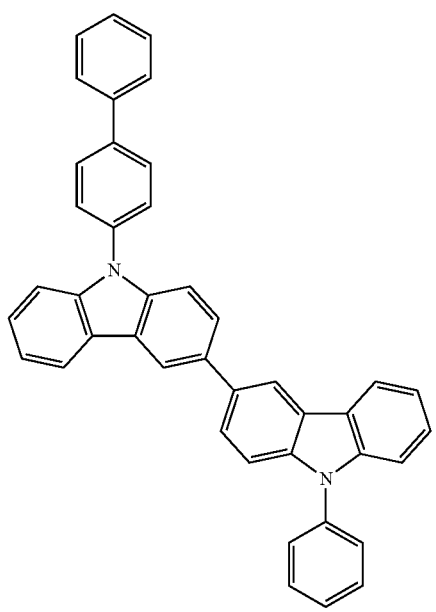

ET-2

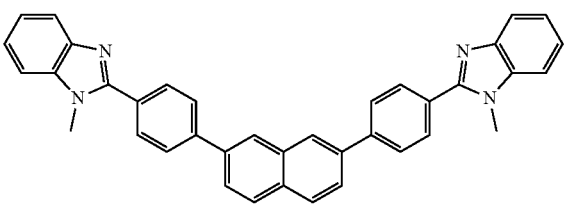

In the above process, the deposition rate of the organic material was maintained at 0.4~0.7 Å/s, the deposition rate of the aluminum was maintained at 2 Å/s, and the degree of vacuum during deposition was maintained at $1 \times 10^{-7}$ to $5 \times 10^{-8}$ torr.

Experimental Examples 2 to 8

An organic light emitting device was prepared in the same manner as in Experimental Example 1, except that the compound described in Table 1 below was used instead of Compound 1 in Experimental Example 1.

Comparative Experimental Examples 1 and 2

An organic light emitting device was prepared in the same manner as in Experimental Example 1, except that the compound described in Table 1 below was used instead of Compound 1 in Experimental Example 1. The Compounds CE1 and CE2 in Table 1 are as follows:

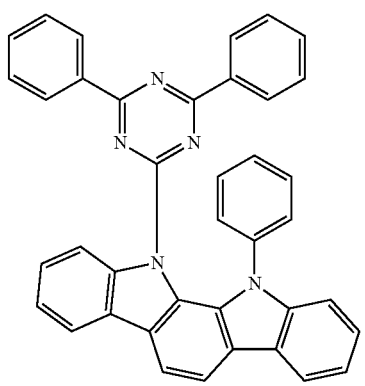

CE1

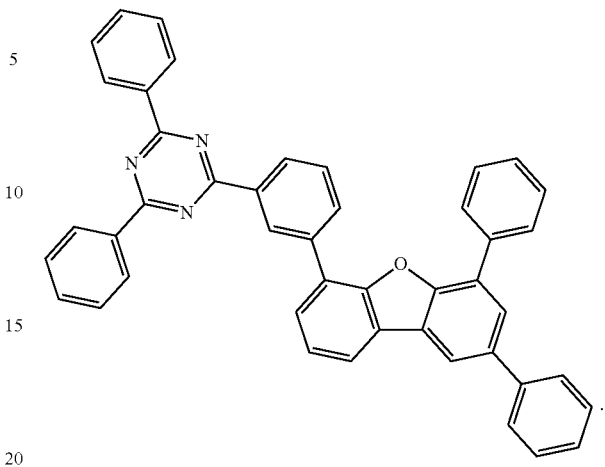

CE2

The voltage, efficiency, color coordinates, and lifetime were measured by applying a current to the organic light emitting devices manufactured in the experimental examples and comparative experimental examples, and the results are shown in Table 1 below. As used herein, T95 means the time required for the luminance to be reduced to 95% when the initial luminance at the current density of 20 mA/cm² is taken as 100%.

For the organic light emitting devices manufactured in the experimental examples and comparative experimental examples, the driving voltage, the current efficiency, and the color coordinates were measured at current density of 10 mA/cm², and the lifetime (LT95) was measured at a current density of 50 mA/cm². The results are shown in Table 1 below.

TABLE 1

| | Compound | Voltage (V) (@10 mA/cm²) | Efficiency (Cd/A) (@10 mA/cm²) | color coordinates (x, y) | Lifetime(LT95, h) (@50 mA/cm²) |
|---|---|---|---|---|---|
| Experimental Ex. 1 | Compound 1 | 4.0 | 79 | 0.46, 0.54 | 130 |
| Experimental Ex. 2 | Compound 2 | 3.9 | 79 | 0.46, 0.54 | 155 |
| Experimental Ex. 3 | Compound 3 | 3.9 | 77 | 0.46, 0.53 | 195 |
| Experimental Ex. 4 | Compound 4 | 3.8 | 79 | 0.46, 0.54 | 120 |
| Experimental Ex. 5 | Compound 5 | 3.9 | 81 | 0.46, 0.54 | 110 |
| Experimental Ex. 6 | Compound 6 | 4.1 | 83 | 0.46, 0.53 | 115 |
| Experimental Ex. 7 | Compound 7 | 4.2 | 80 | 0.46, 0.54 | 135 |
| Experimental Ex. 8 | Compound 8 | 4.1 | 80 | 0.46, 0.54 | 145 |
| Comparative Experimental Ex. 1 | Compound CE1 | 4.5 | 70 | 0.46, 0.53 | 100 |
| Comparative Experimental Ex 2 | Compound CE2 | 4.3 | 77 | 0.44, 0.55 | 40 |

As shown in Table 1, when using the compound of Chemical Formula 1 of the present disclosure as a light emitting layer material, it was confirmed that the driving voltage is lower than the comparative experimental examples and exhibits excellent light emission efficiency and lifetime. This is because the more the substitution in the substituent site of the dibenzofuran, the better the stability of the material, and the efficiency and lifespan of the organic light emitting device are improved.

| Explanation of Signs | |
|---|---|
| 1: substrate | 2: anode |
| 3: light emitting layer | 4: cathode |
| 5: hole injection layer | 6: hole transport layer |
| 7: light emitting layer | 8: electron transport layer |

The invention claimed is:

1. A compound Chemical Formula 1:

[Chemical Formula 1]

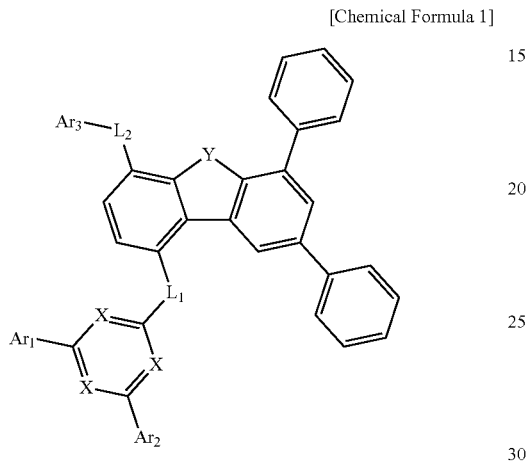

wherein, in Chemical Formula 1:
each X is independently N or CH, with the proviso that at least one X is N;
Y is O or S;
$L_1$ and $L_2$ are each independently a single bond, a substituted or unsubstituted $C_{6-60}$ arylene, or a substituted or unsubstituted $C_{2-60}$ heteroarylene containing at least one heteroatom selected from the group consisting of N, O, and S;
$Ar_1$ and $Ar_2$ are each independently a substituted or unsubstituted $C_{6-60}$ aryl, or a substituted or unsubstituted $C_{2-60}$ heteroaryl containing at least one heteroatom selected from the group consisting of N, O, and S; and
$Ar_3$ is a substituted or unsubstituted $C_{6-60}$ aryl, or a substituted or unsubstituted $C_{2-60}$ heteroaryl containing at least one heteroatom selected from the group consisting of N, O, and S.

2. The compound of claim 1, wherein:
$L_1$ is single bond, phenylene, biphenyldiyl, naphthalenediyl, or pyridinediyl.

3. The compound of claim 1, wherein:
$L_2$ is a single bond or phenylene.

4. The compound of claim 1, wherein:
$Ar_1$ and $Ar_2$ are each independently phenyl, biphenylyl, terphenylyl, naphthyl, phenanthrenyl, dibenzofuranyl, dibenzothiophenyl, carbazolyl, or 9-phenyl-9H-carbazolyl.

5. The compound of claim 1, wherein:
$Ar_1$ is phenyl; and
$Ar_2$ is phenyl, biphenylyl, terphenylyl, naphthyl, phenanthrenyl, dibenzofuranyl, dibenzothiophenyl, carbazolyl, or 9-phenyl-9H-carbazolyl.

6. The compound of claim 1, wherein:
$Ar_3$ is unsubstituted, or is substituted with a $C_{1-60}$ alkyl, a halogen, a cyano, or a tri($C_{1-60}$ alkyl)silyl.

7. The compound of claim 6, wherein:
$Ar_3$ is phenyl, biphenylyl, terphenylyl, naphthyl, phenanthrenyl, triphenylenyl, pyridinyl, quinolinyl, dibenzofuranyl, or dibenzothiophenyl.

8. The compound of claim 1, wherein:
the compound of Chemical Formula 1 is any one compound selected from the group consisting of the following:

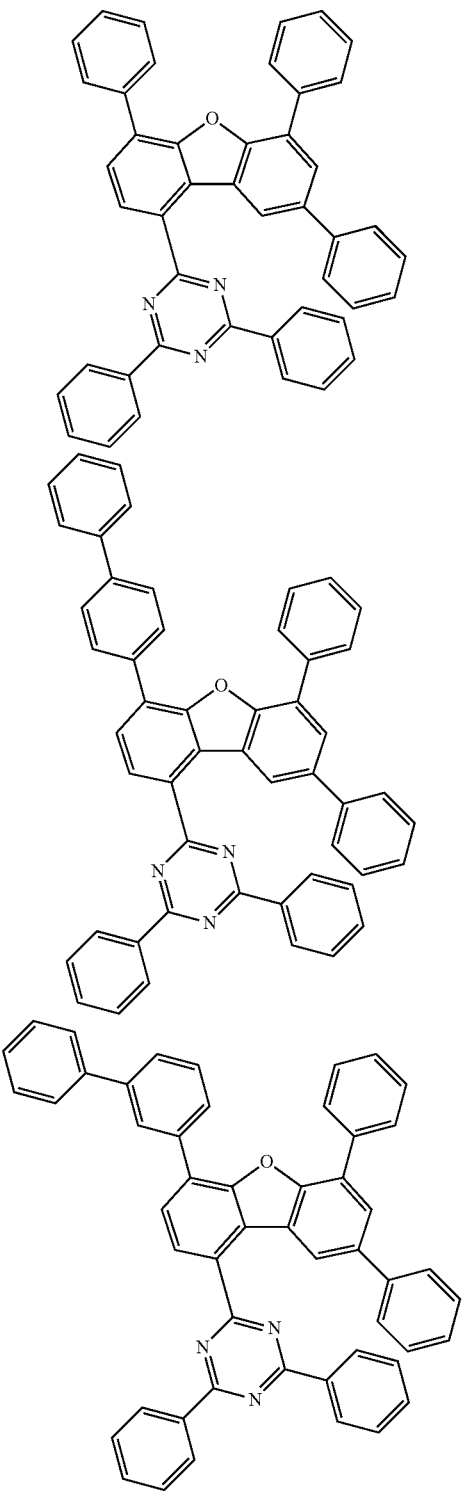

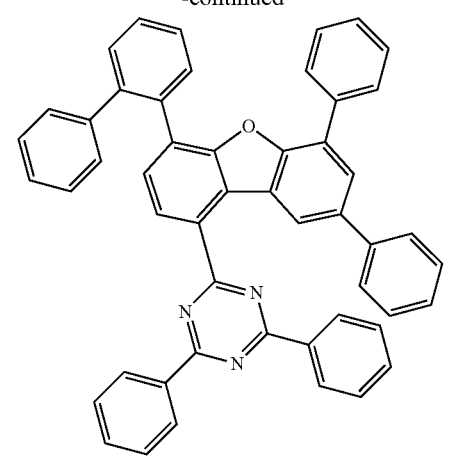
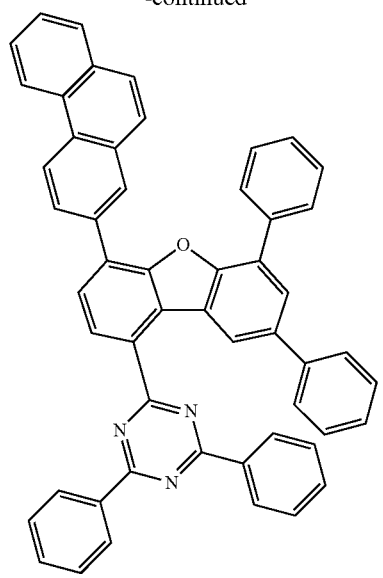
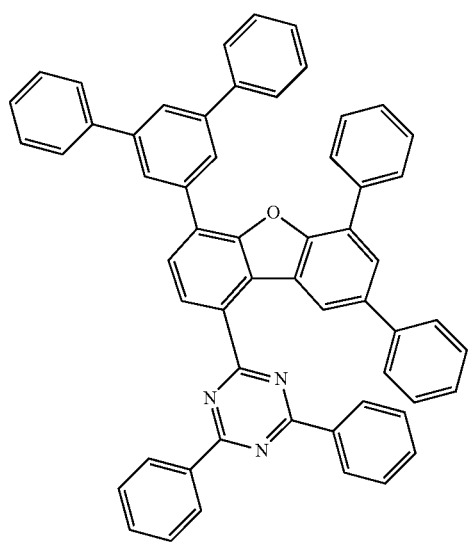
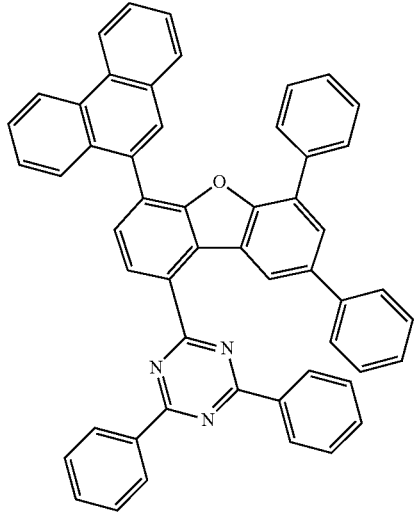
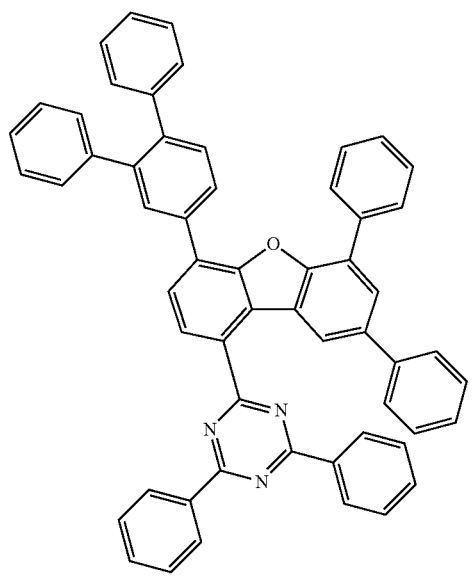
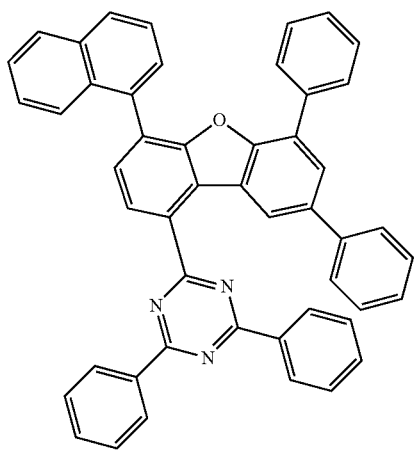

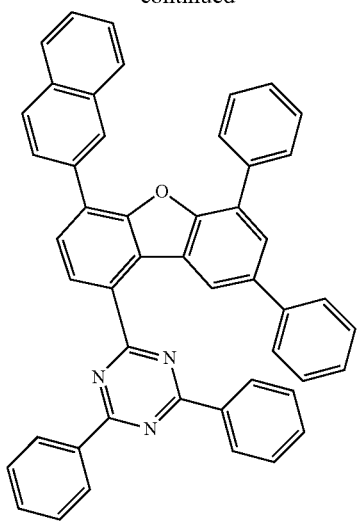
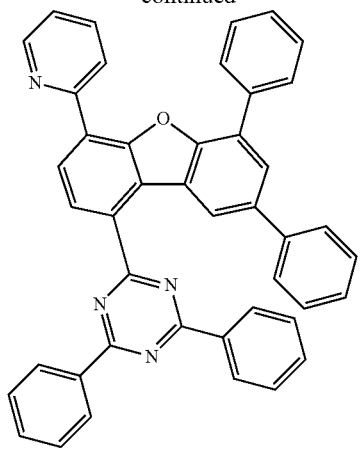
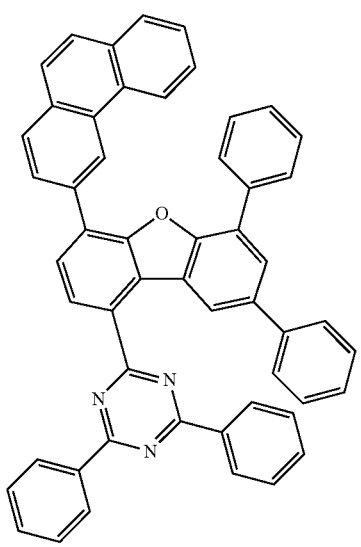
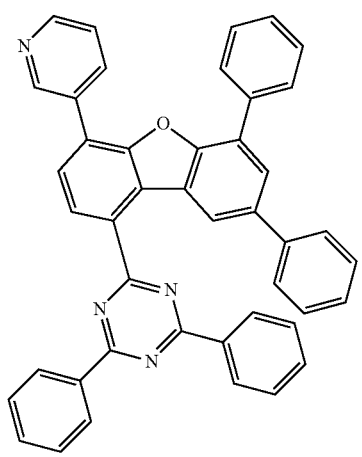
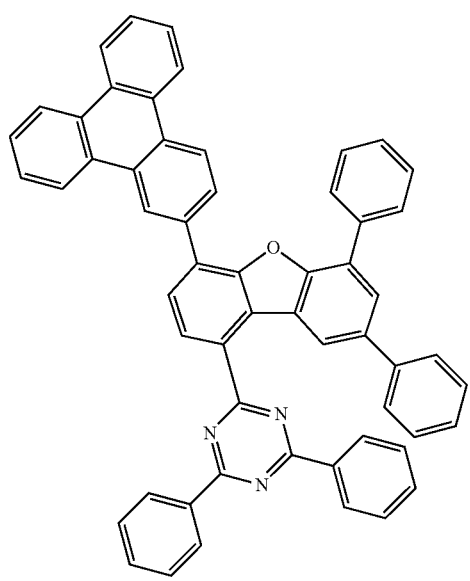
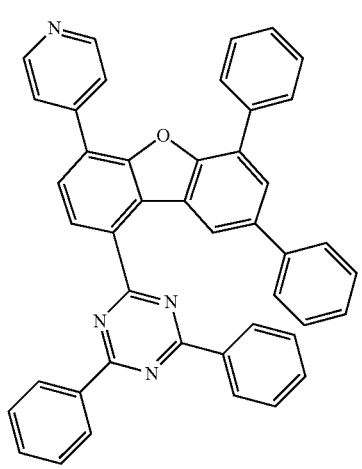

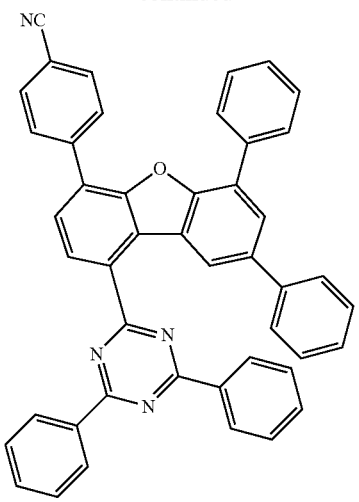
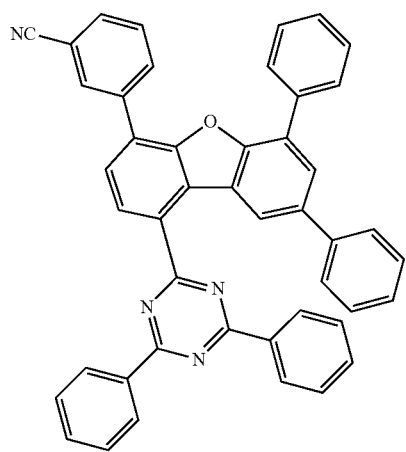
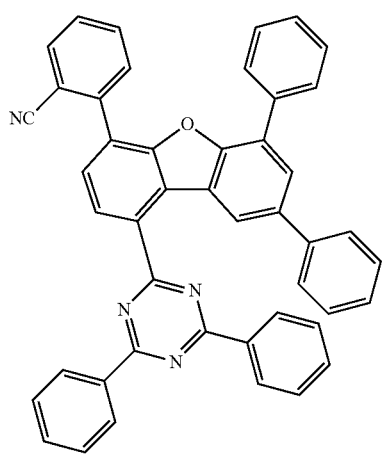
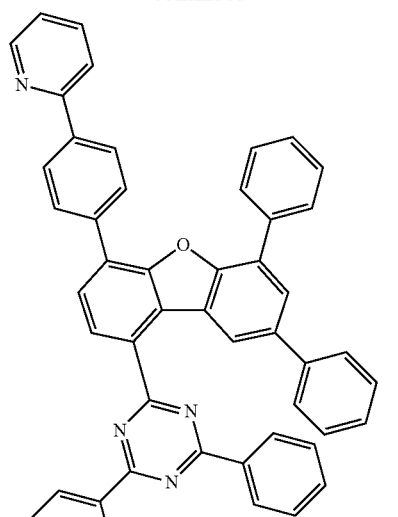
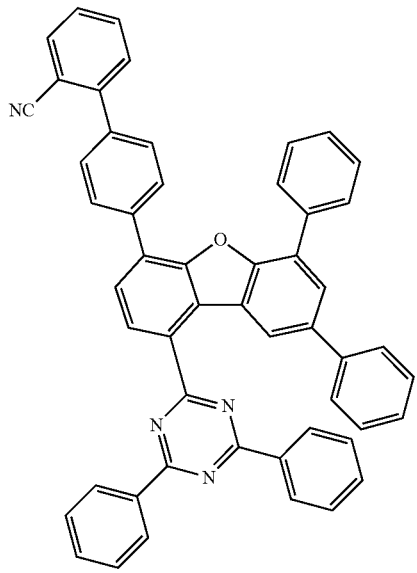
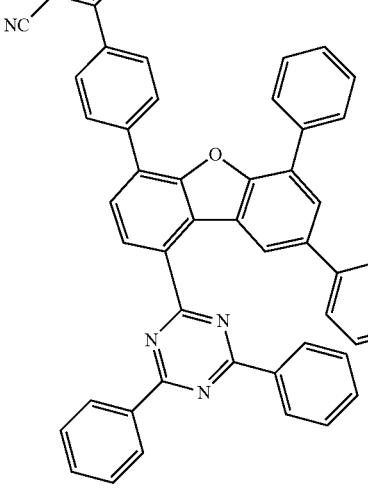

85
-continued
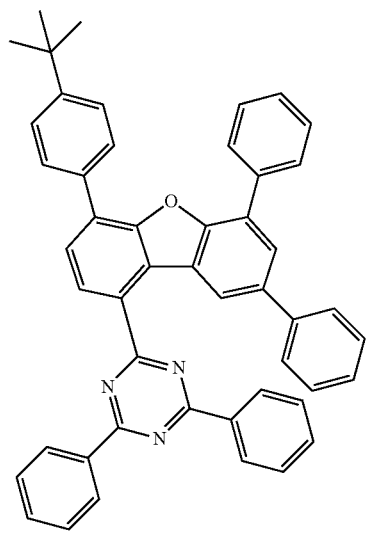
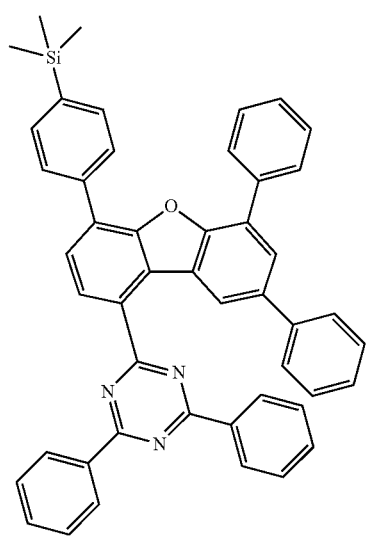
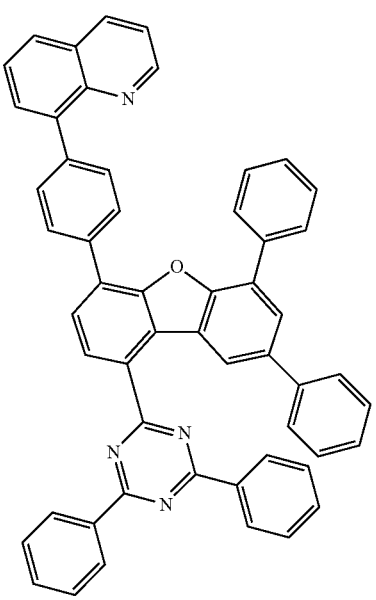
86
-continued
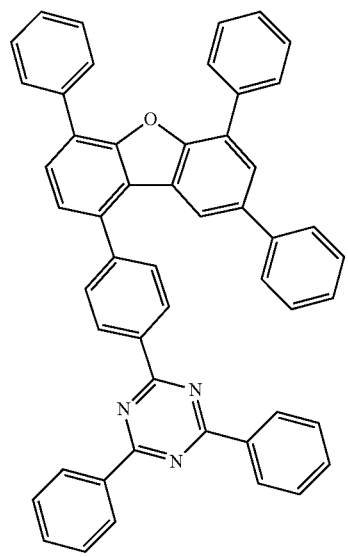
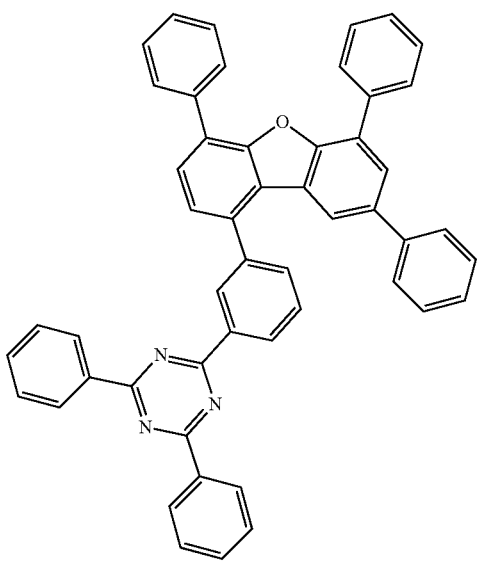
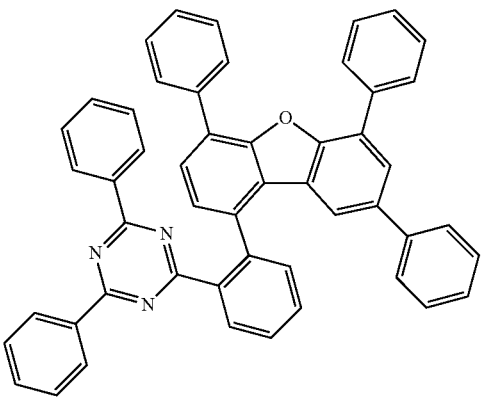

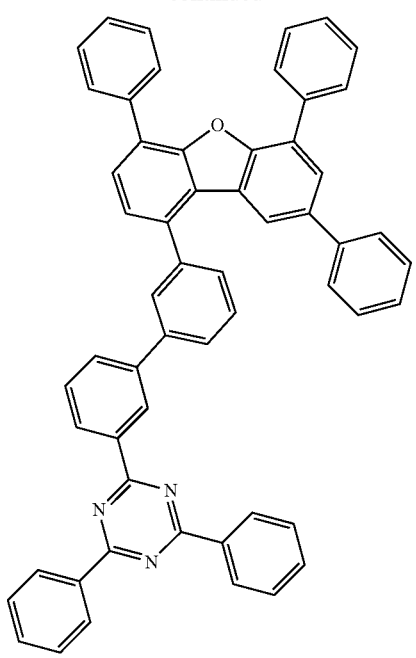
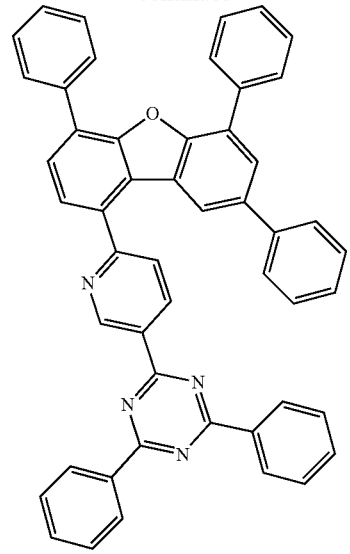
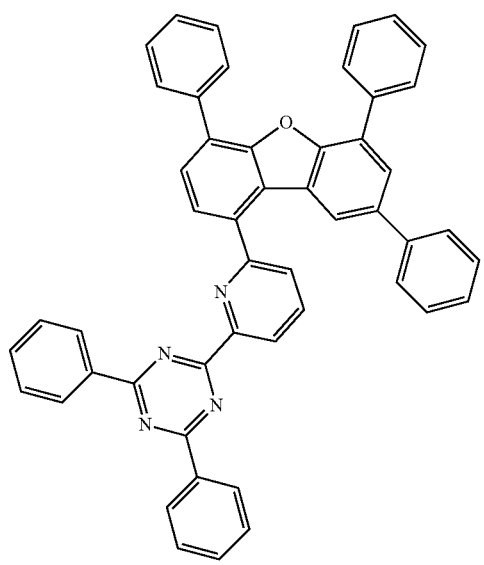
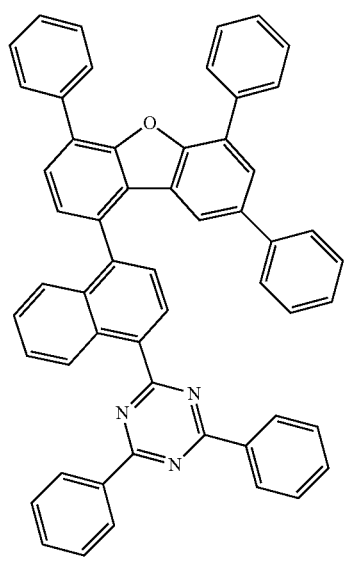
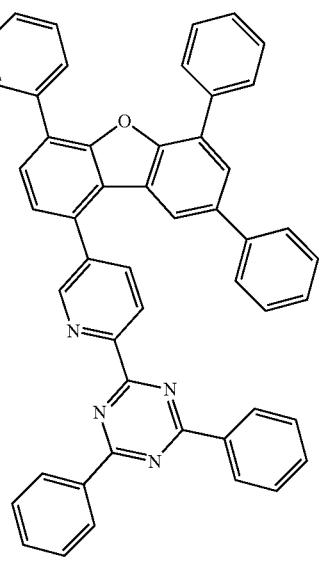

89
-continued
90
-continued
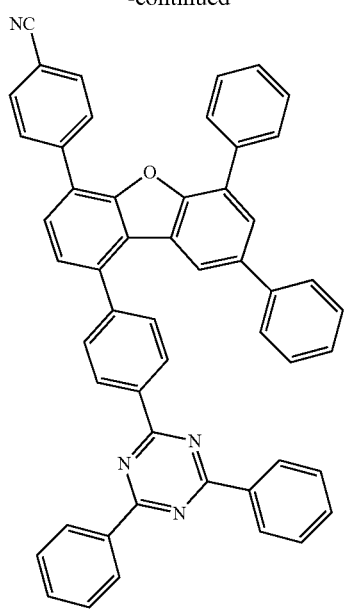
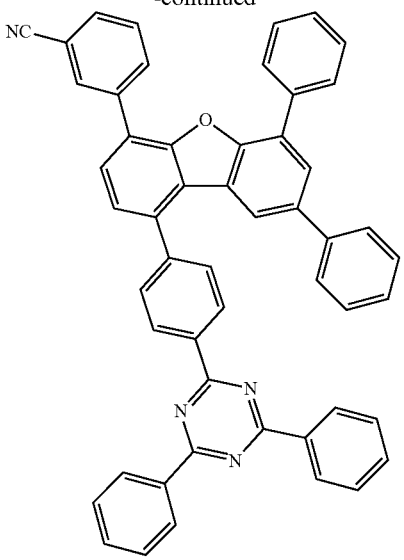

91
-continued
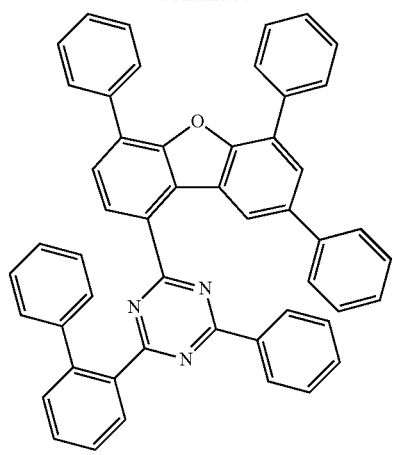
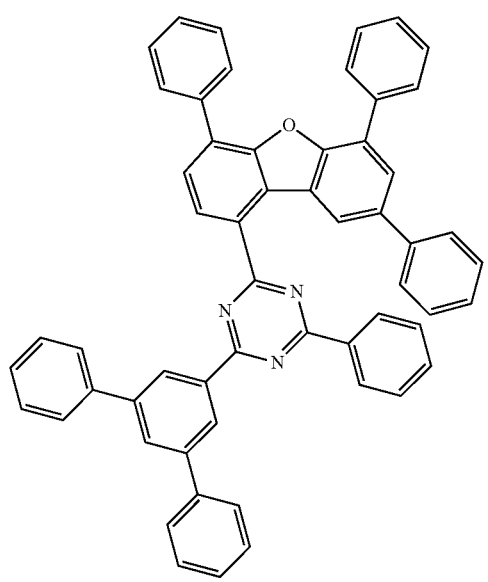
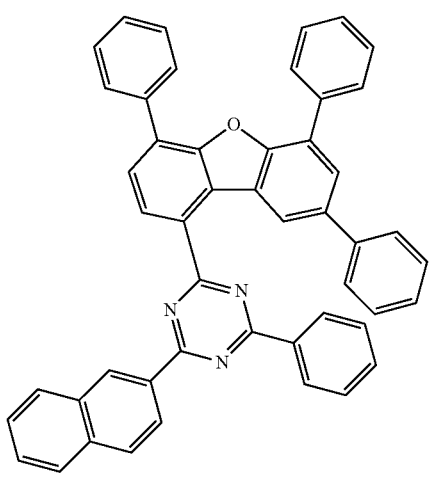
92
-continued
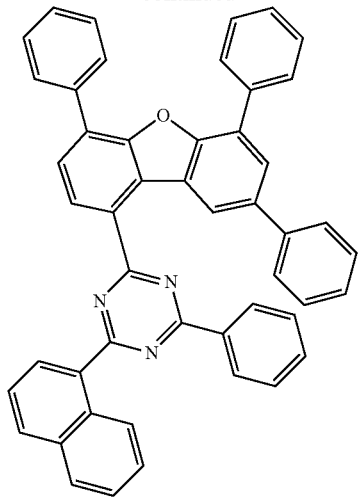
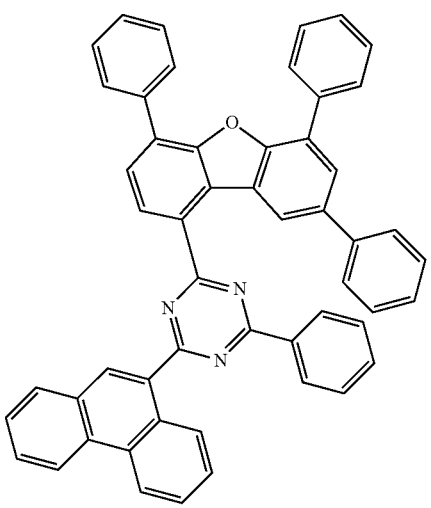
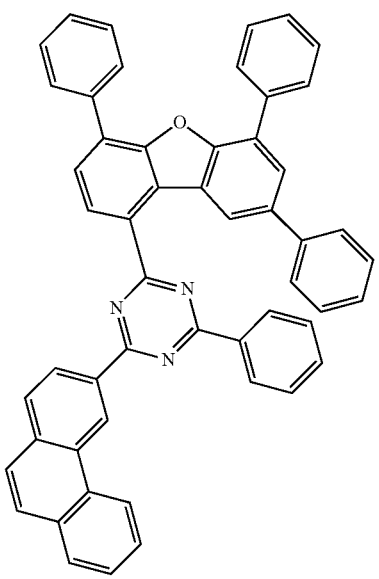

93
-continued
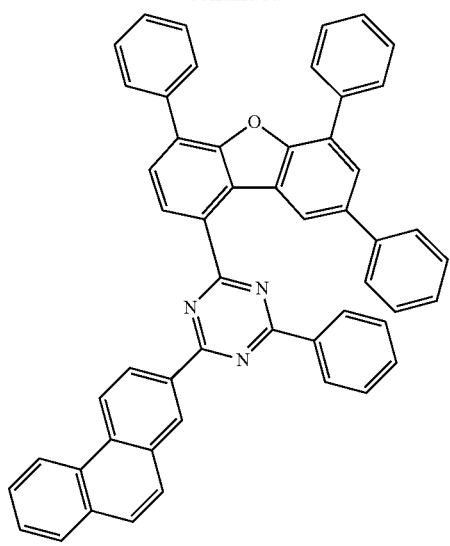
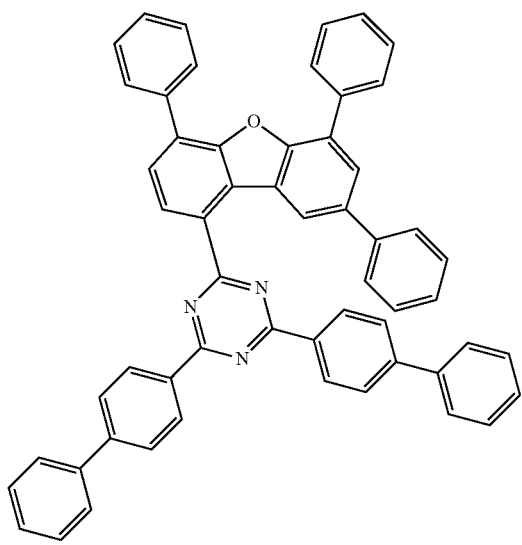
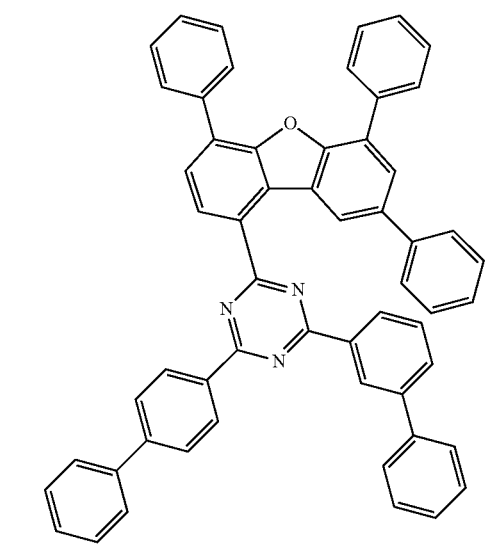
94
-continued
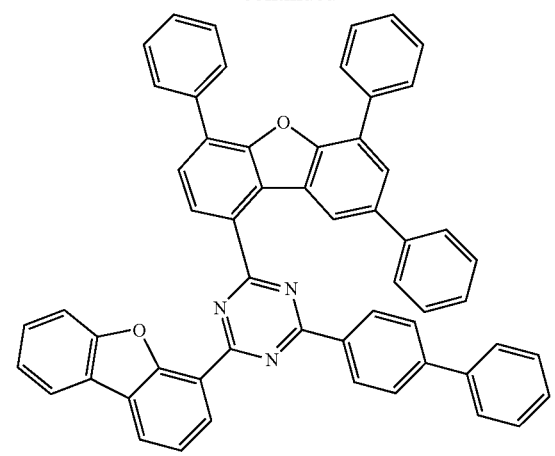
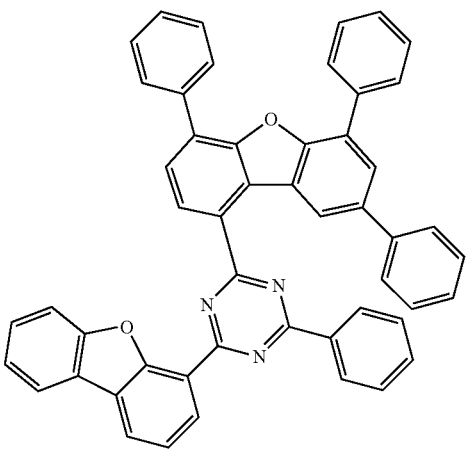
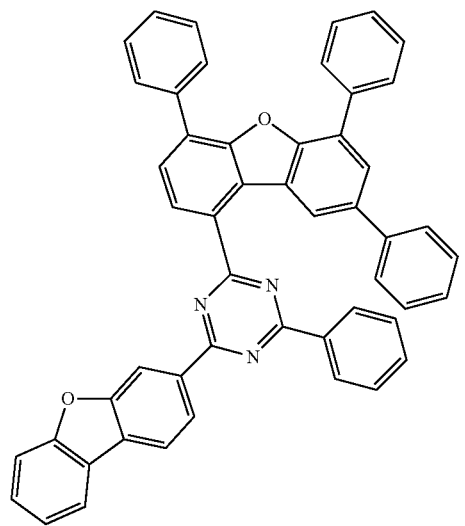

95
-continued
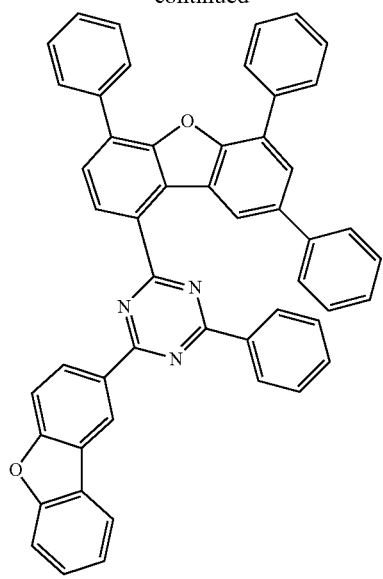
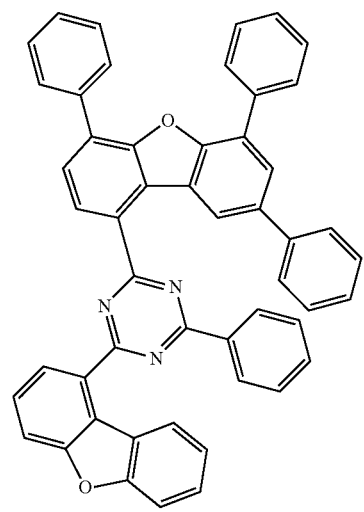
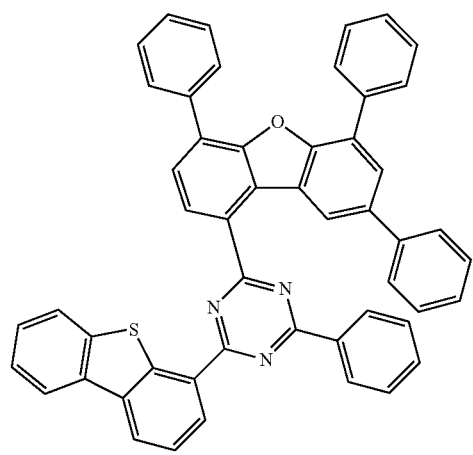
96
-continued
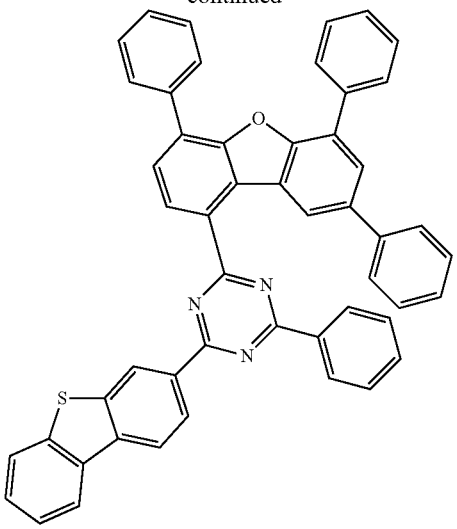
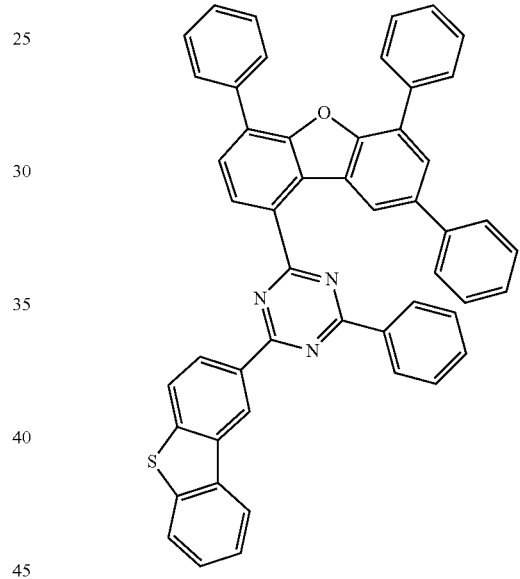
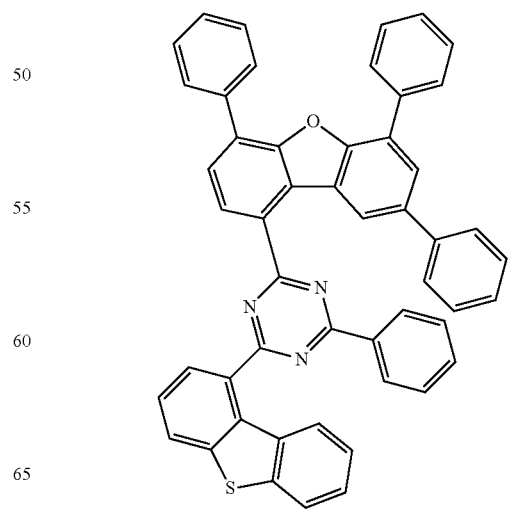

97
-continued
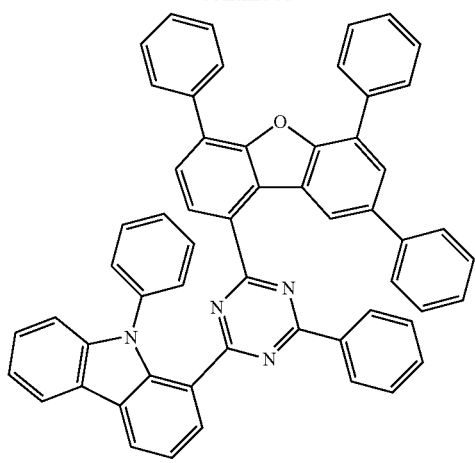
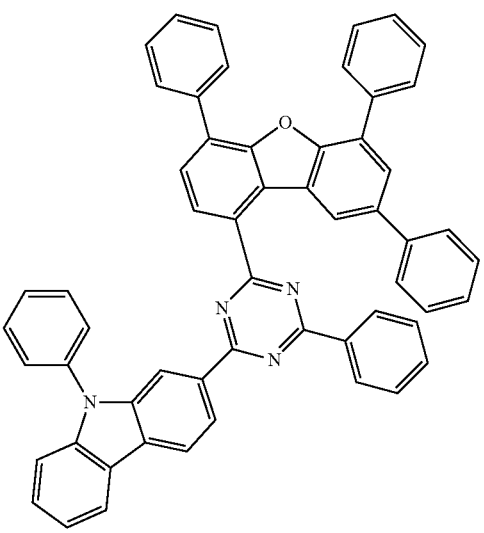
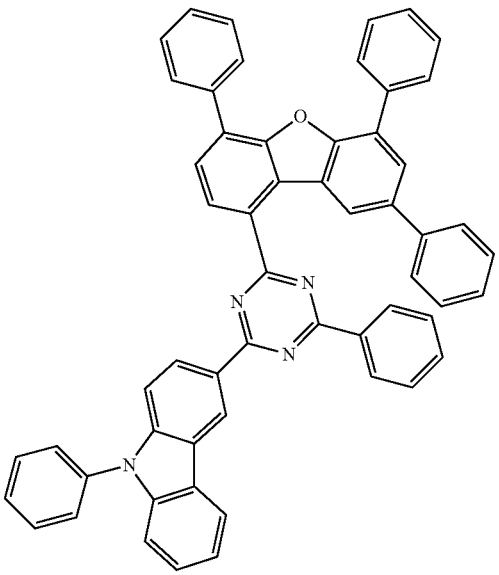
98
-continued
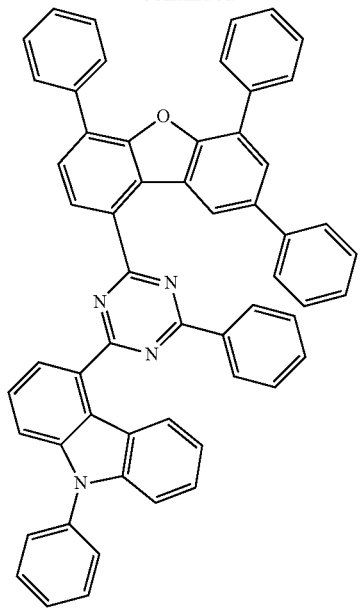
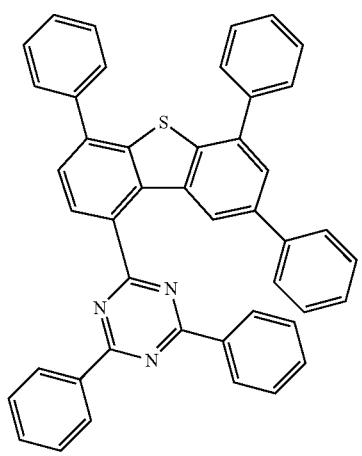
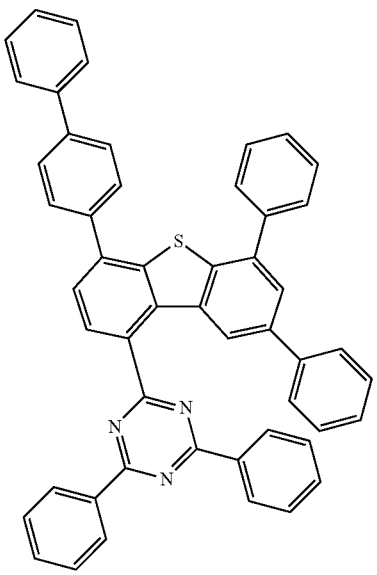

99
-continued
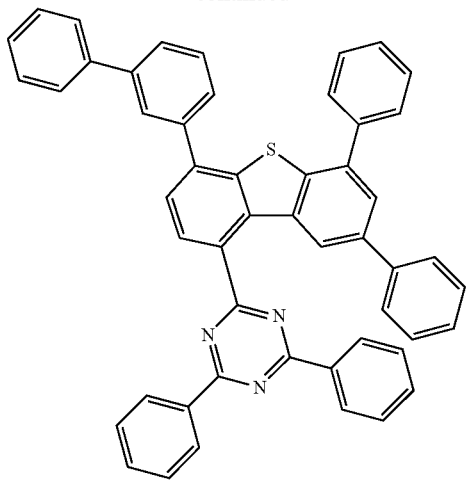
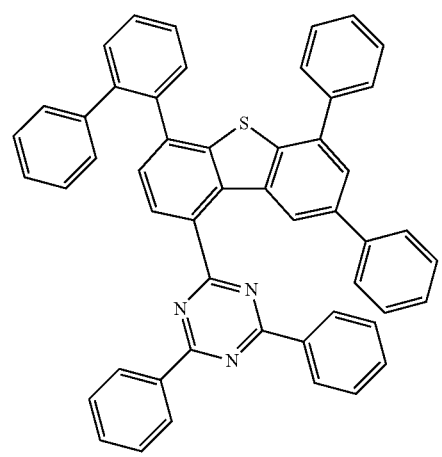
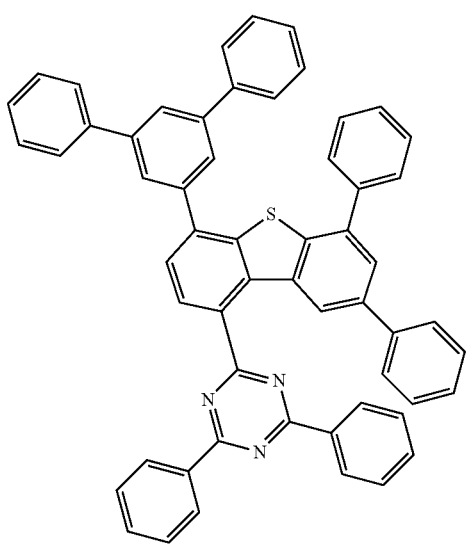
100
-continued
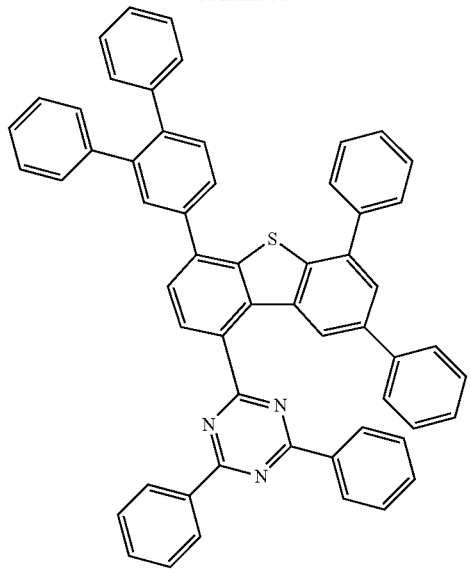
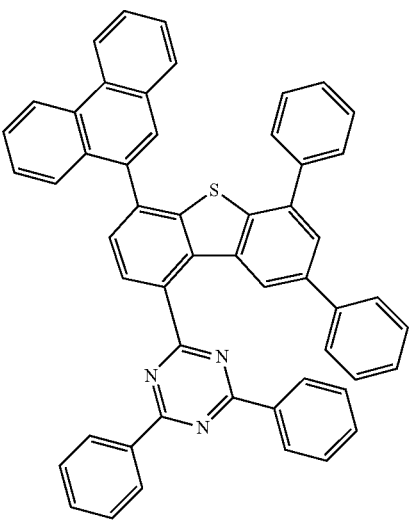

101
-continued

102
-continued

103
-continued
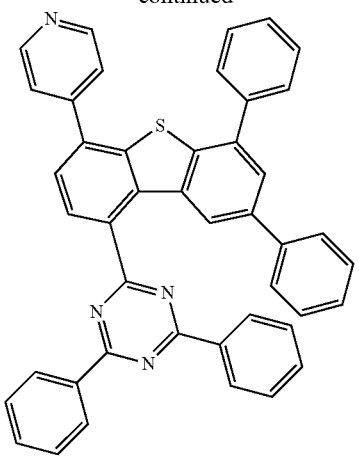
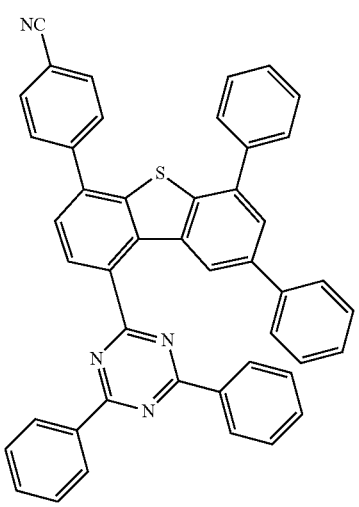
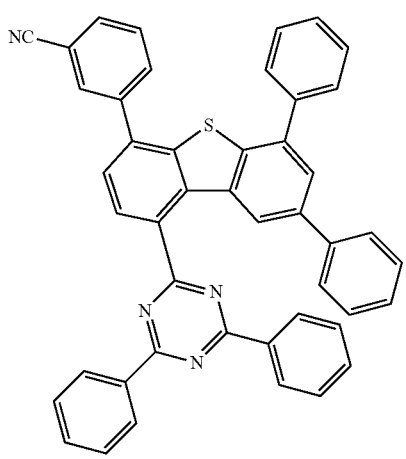
104
-continued
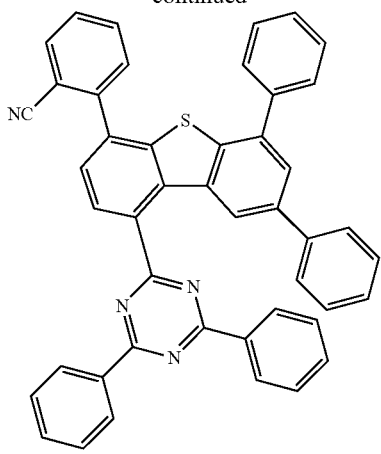
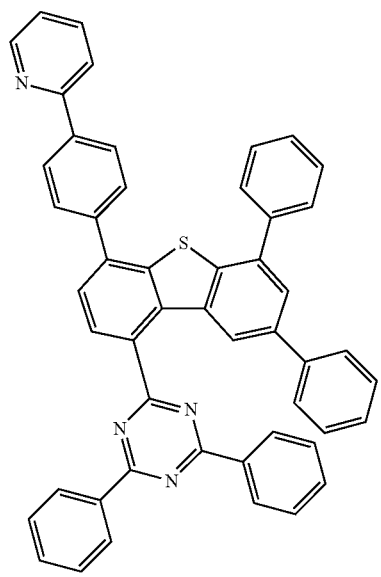
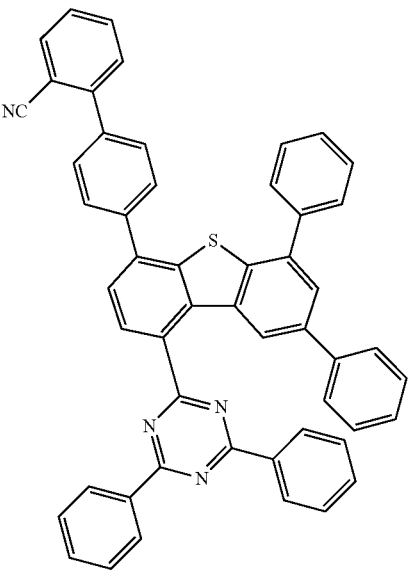

105
-continued
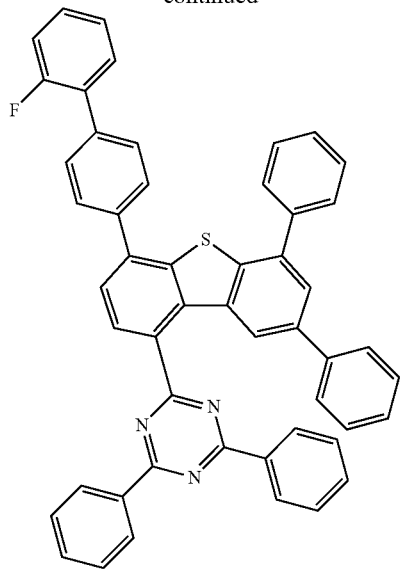
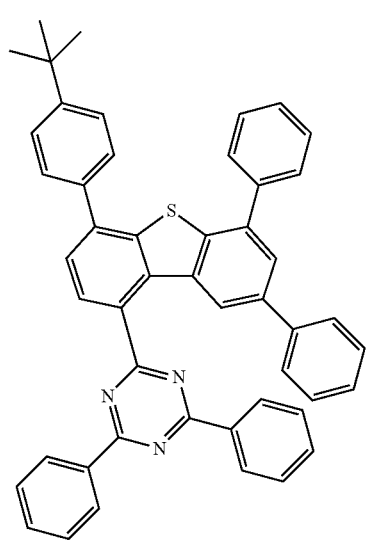
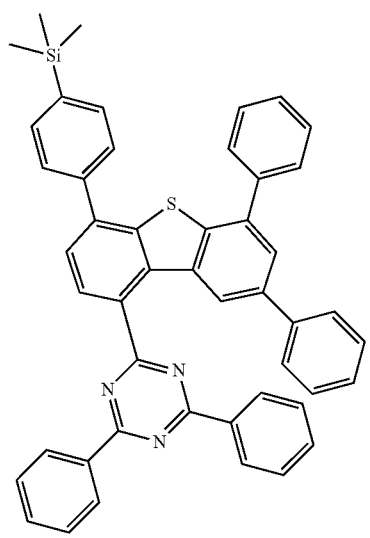
106
-continued
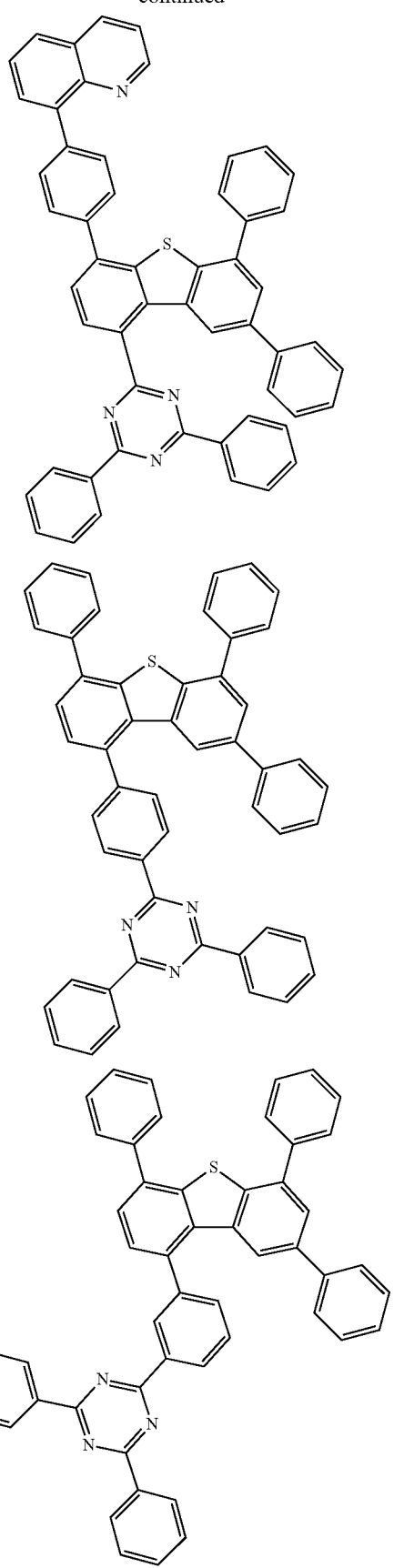

107
-continued
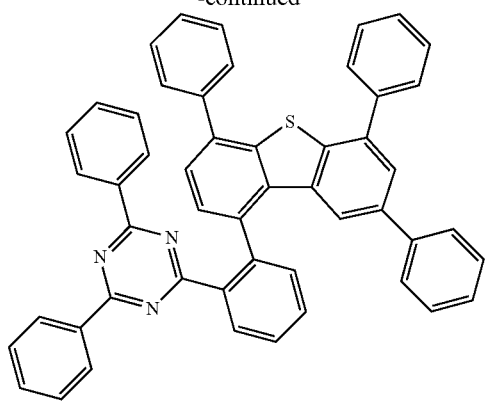
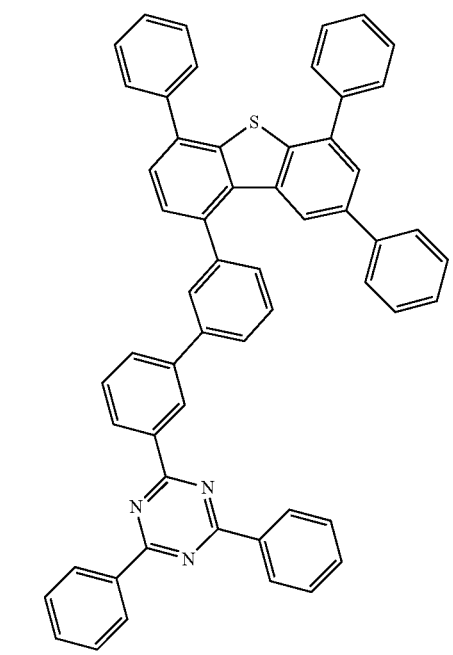
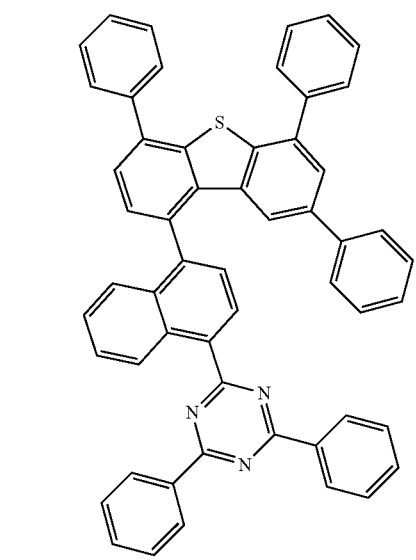
108
-continued
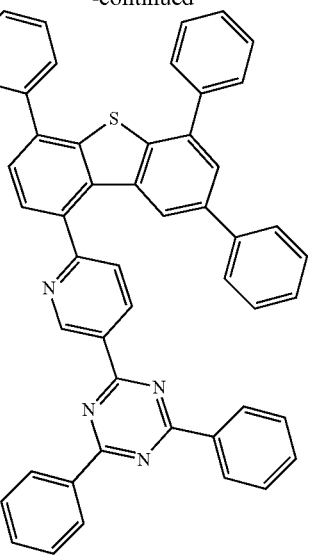
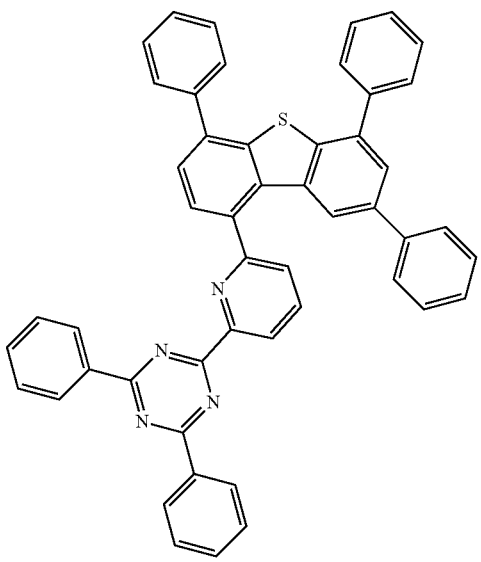
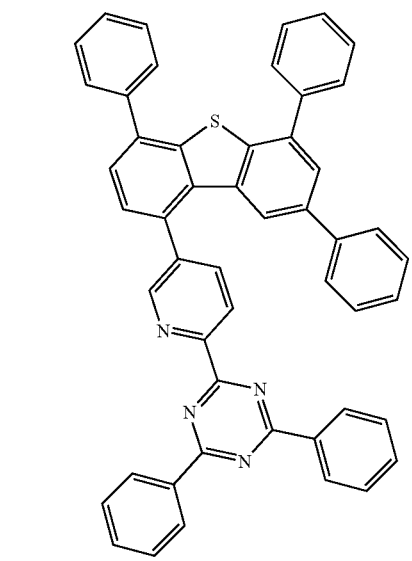

109
-continued
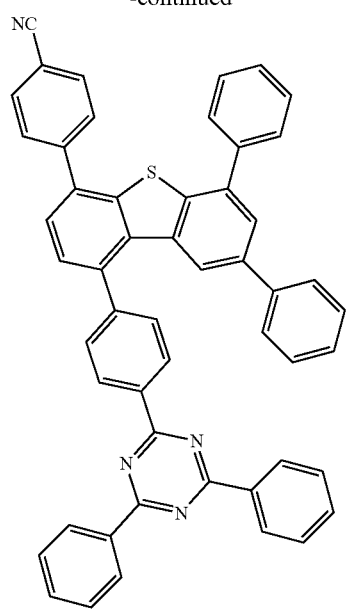
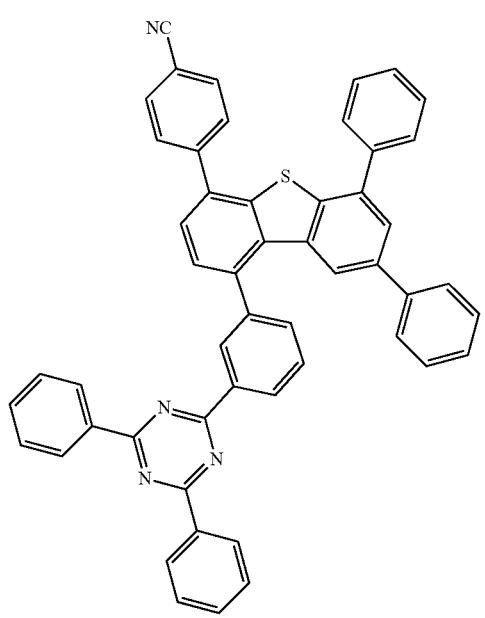
110
-continued
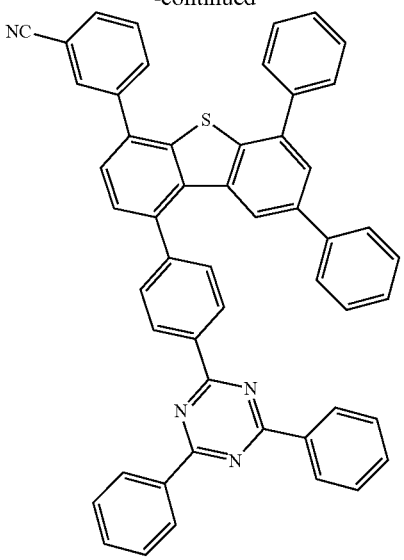
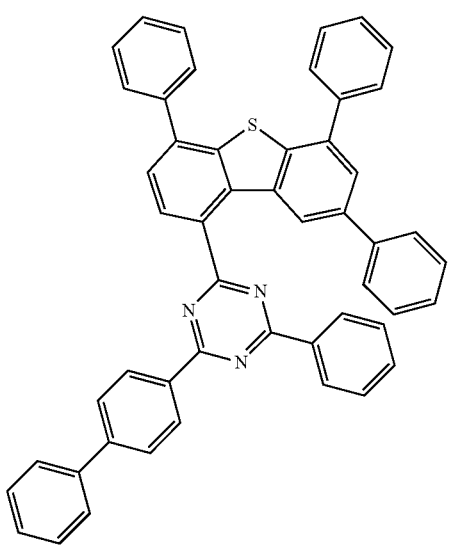
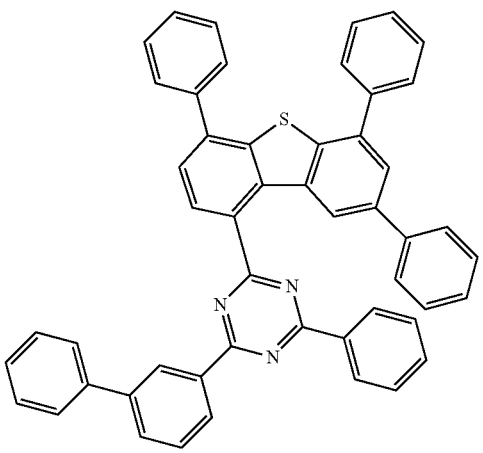

111
-continued
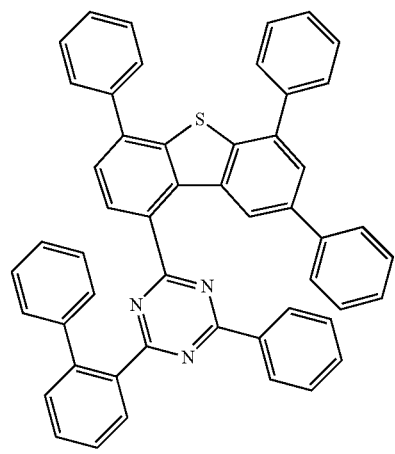
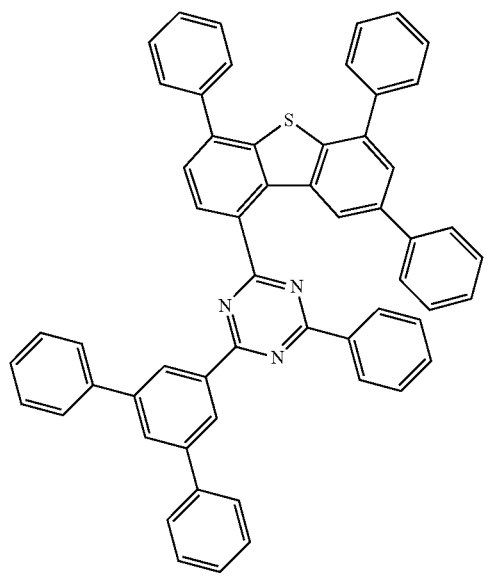
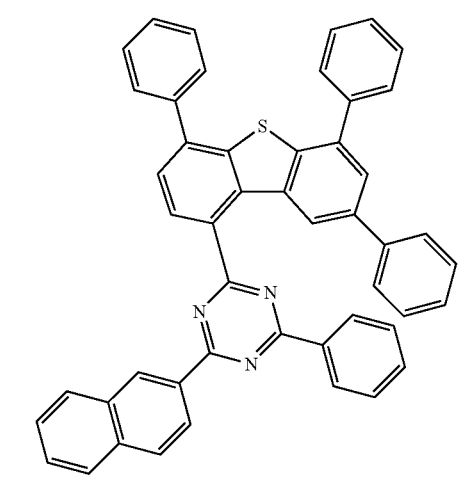
112
-continued
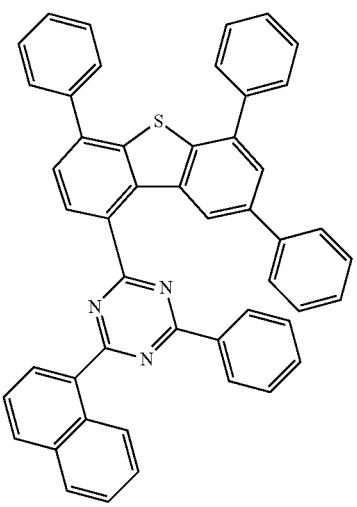
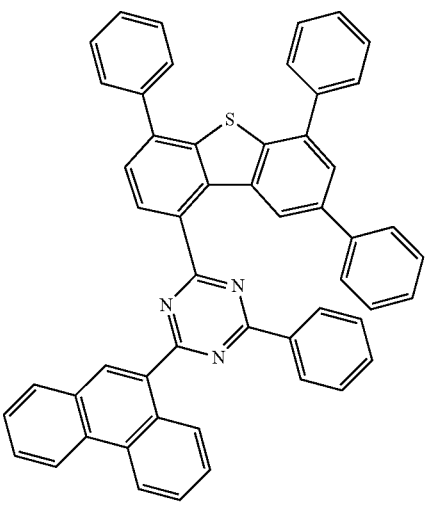
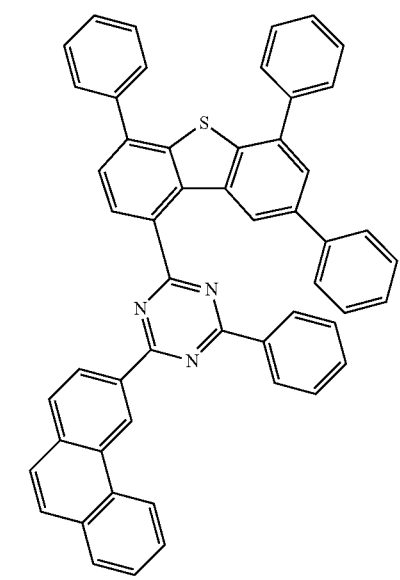

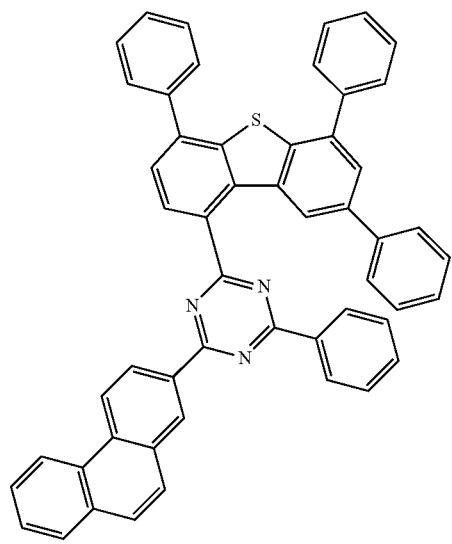
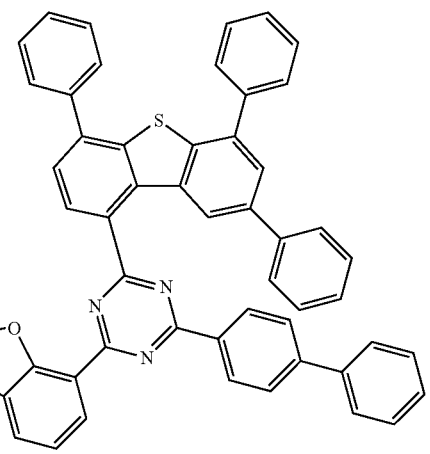
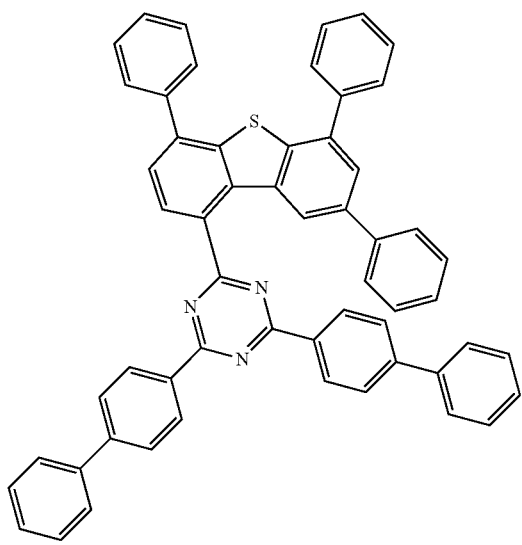
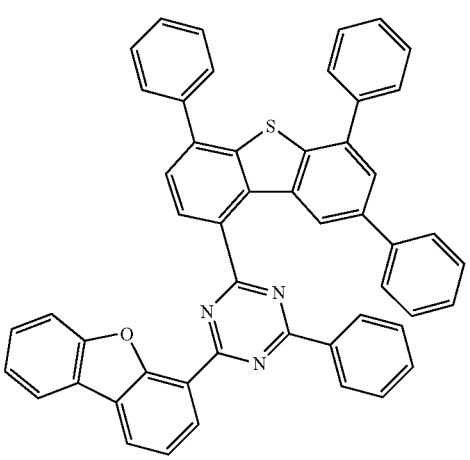
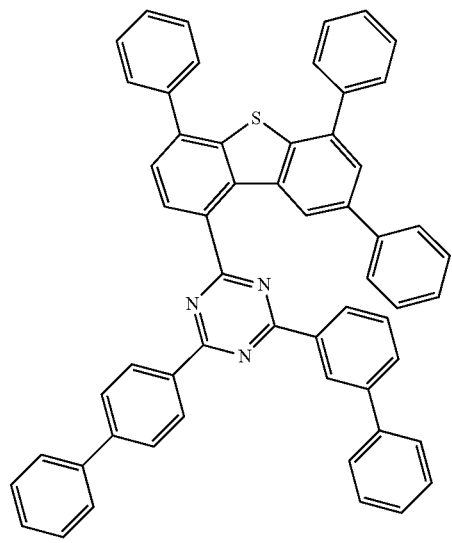
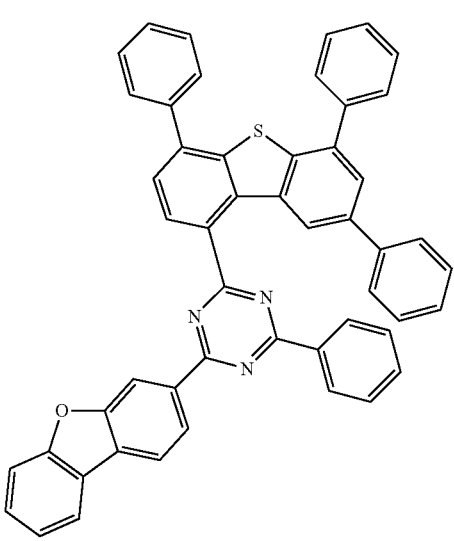

115
-continued
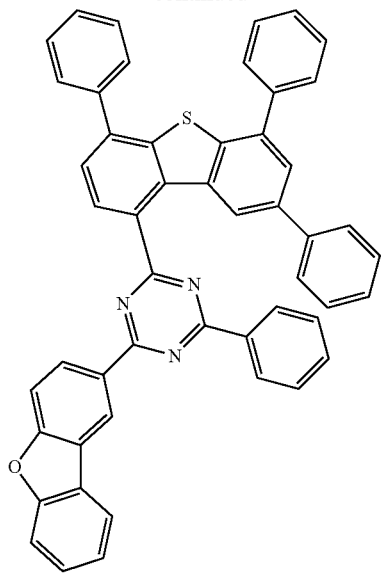
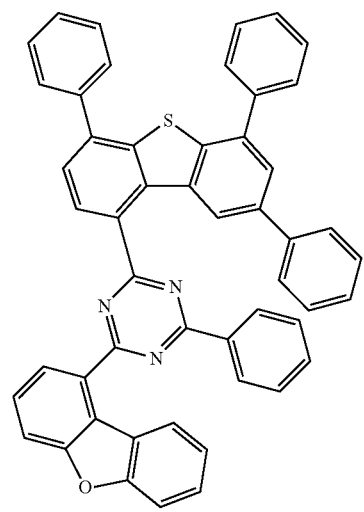
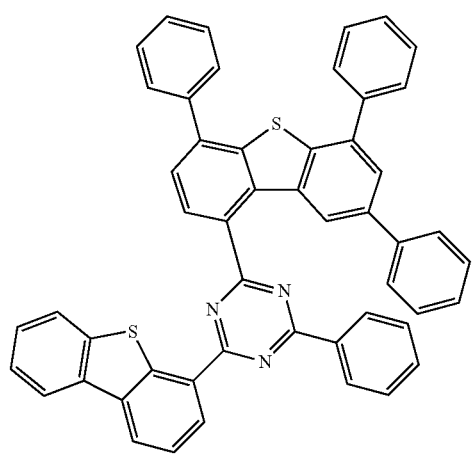
116
-continued
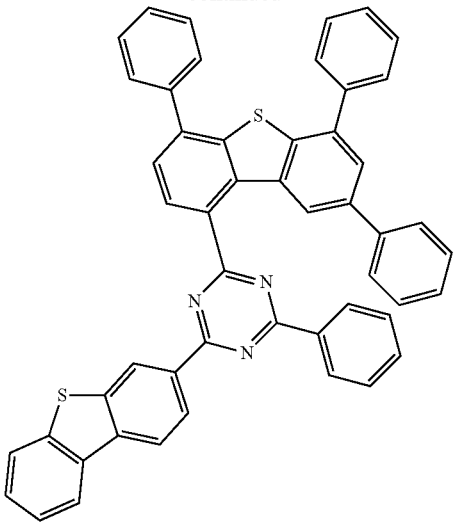
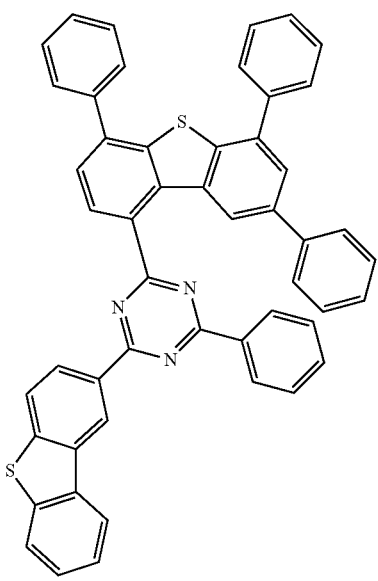
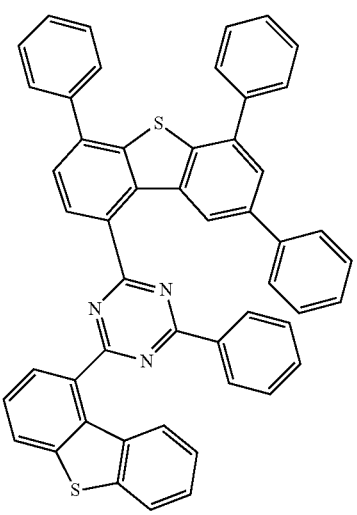

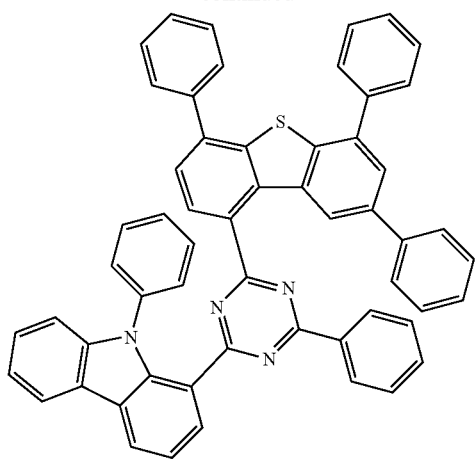
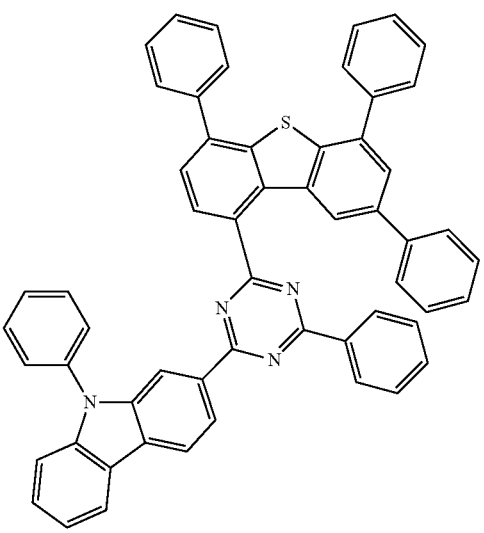
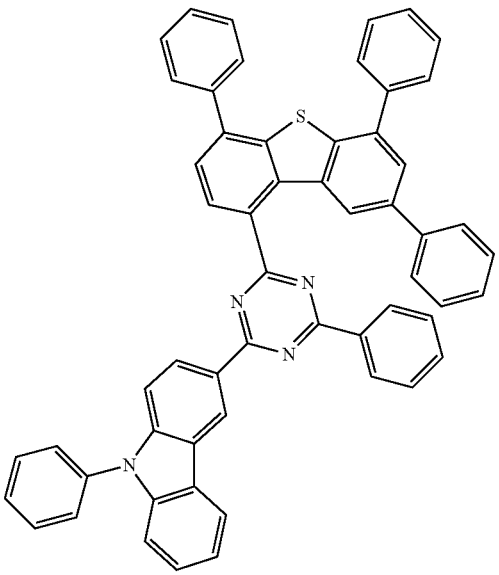
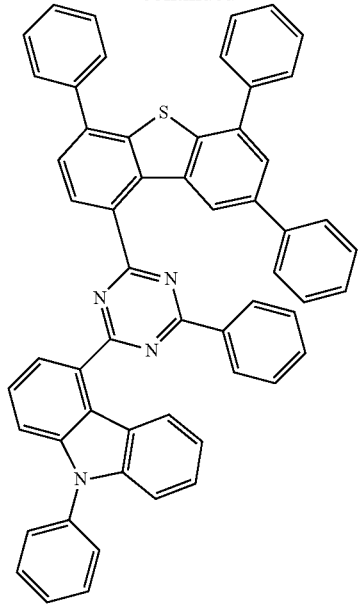
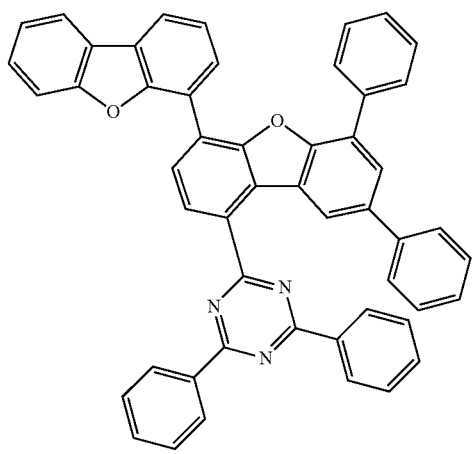
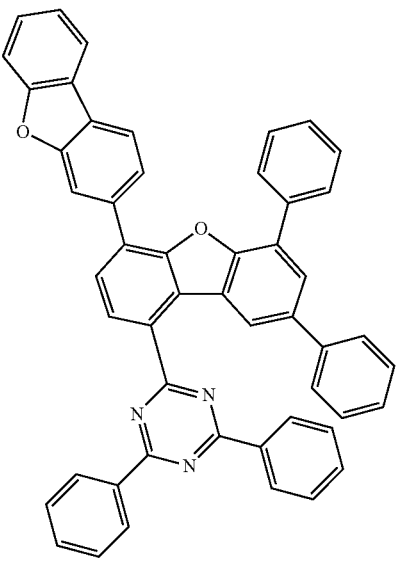

119
-continued
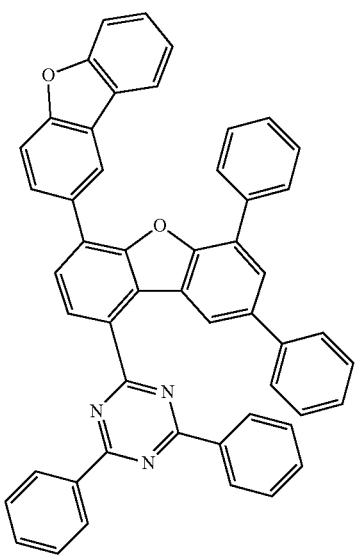
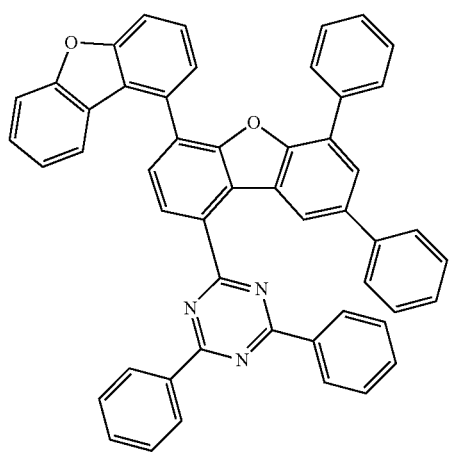
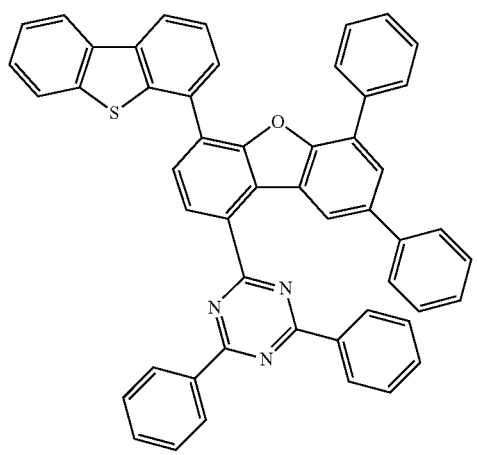
120
-continued
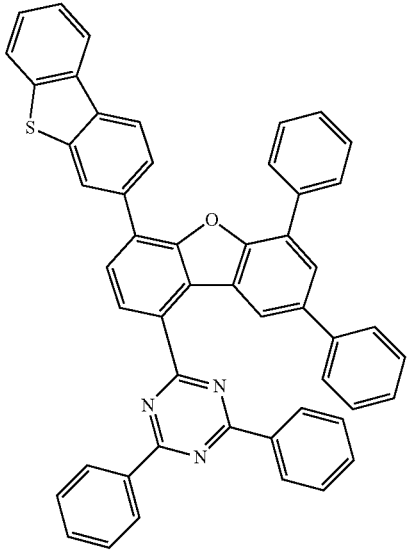
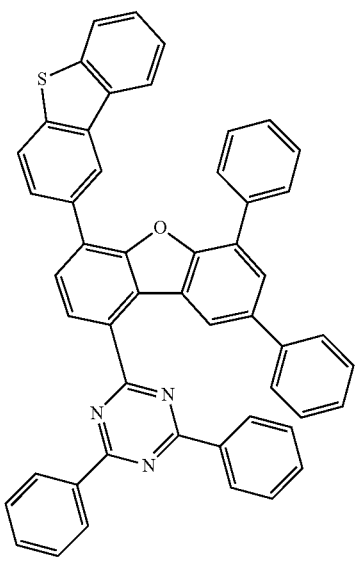
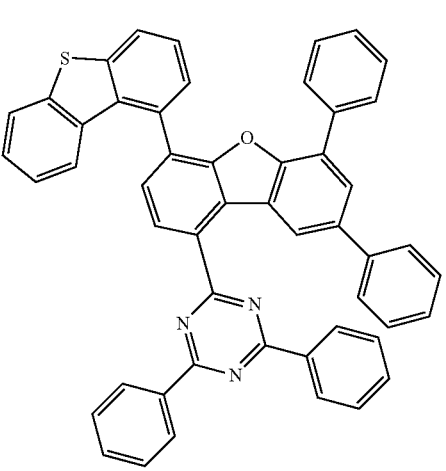

121
-continued
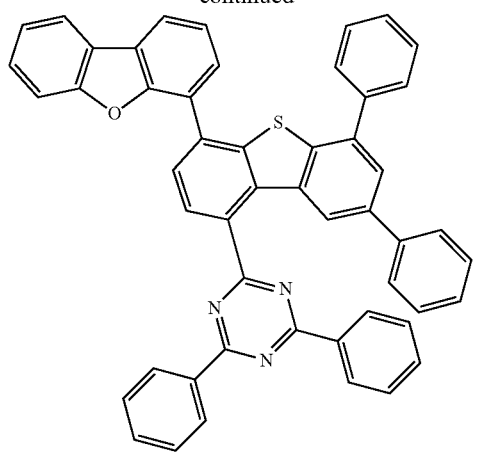
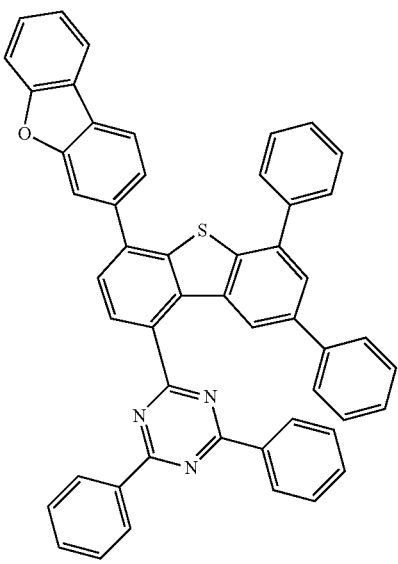
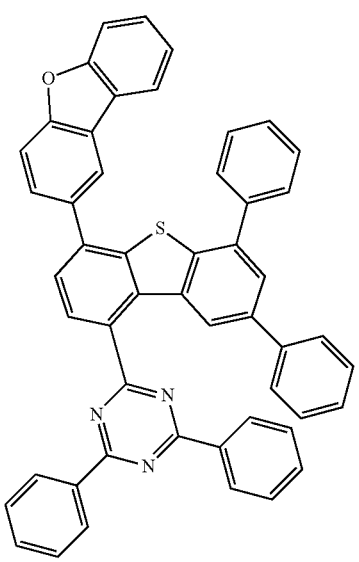
122
-continued
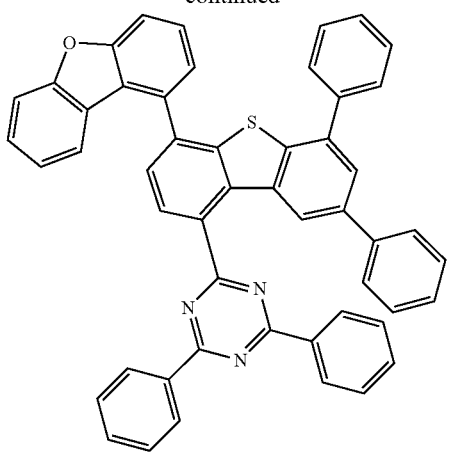
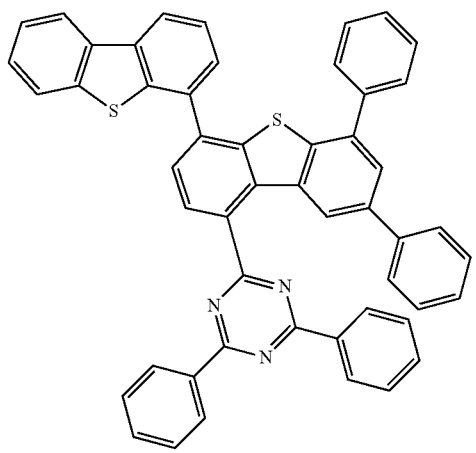
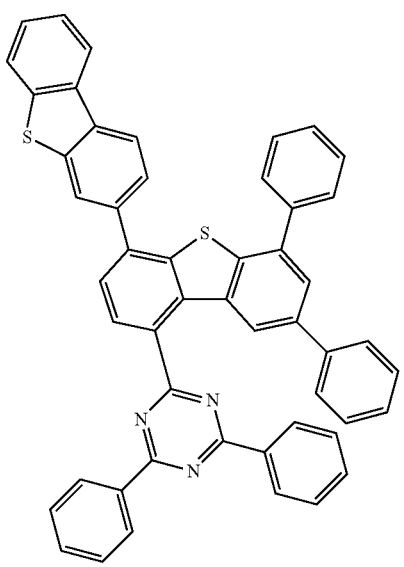

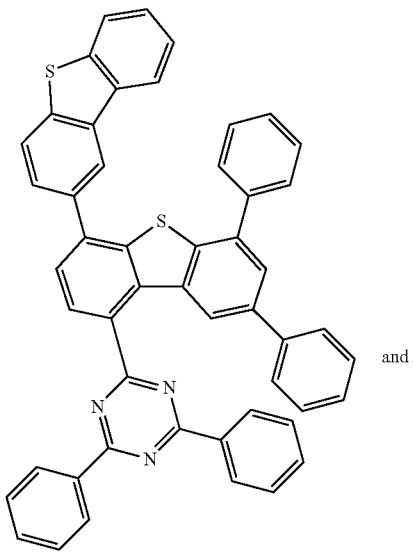
and
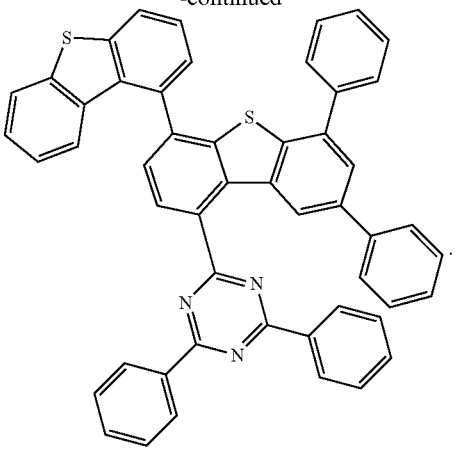
.
9. An organic light emitting device, comprising:
a first electrode;
a second electrode provided opposite to the first electrode; and
one or more organic material layers provided between the first electrode and the second electrode, wherein one or more one layers of the organic material layers comprise the compound according to claim 1.
* * * * *